(12) United States Patent
Buxbaum et al.

(10) Patent No.: US 11,684,306 B2
(45) Date of Patent: Jun. 27, 2023

(54) STABLE WATER ISOTOPE LABELING AND MAGNETIC RESONANCE IMAGING FOR VISUALIZATION OF THE PRESENCE OF AND PREDICTION OF THE LIKELIHOOD OF OCCURENCE OF RAPIDLY DIVIDING CELLS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Nataliya Buxbaum, Bethesda, MD (US); Donald Farthing, Bethesda, MD (US); Martin Lizak, Bethesda, MD (US); Helmut Merkle, Bethesda, MD (US); Natella Maglakelidze, Bethesda, MD (US); Brittany Oliver, Bethesda, MD (US); Ronald Gress, Bethesda, MD (US)

(73) Assignee: THE UNITED STATES OF AMERICA, AS REPRESENTED BY THE SECRETARY, DEPARTMENT OF HEALTH AND HUMAN SERVICES et al., Bethesda, MD (US)

( * ) Notice: Subject to any disclaimer, the term of this patent is extended or adjusted under 35 U.S.C. 154(b) by 939 days.

(21) Appl. No.: 16/345,612

(22) PCT Filed: Oct. 27, 2017

(86) PCT No.: PCT/US2017/058856
§ 371 (c)(1),
(2) Date: Apr. 26, 2019

(87) PCT Pub. No.: WO2018/081626
PCT Pub. Date: May 3, 2018

(65) Prior Publication Data
US 2019/0274616 A1 Sep. 12, 2019

Related U.S. Application Data

(60) Provisional application No. 62/414,554, filed on Oct. 28, 2016.

(51) Int. Cl.
*A61B 5/00* (2006.01)
*A61B 5/055* (2006.01)
(Continued)

(52) U.S. Cl.
CPC ............ *A61B 5/413* (2013.01); *A61B 5/0036* (2018.08); *A61B 5/055* (2013.01);
(Continued)

(58) Field of Classification Search
CPC ....... A61B 5/413; A61B 5/0036; A61B 5/055; A61B 2503/40; G01R 33/34061;
(Continued)

(56) References Cited

U.S. PATENT DOCUMENTS

| 4,665,368 A | 5/1987 | Sugiyama et al. |
| 5,323,113 A | 6/1994 | Cory et al. |

(Continued)

OTHER PUBLICATIONS

Busch, R., "Measurement of cell proliferation by heavy water labeling", Nat Protoc, (20070000), vol. 2, pp. 3045-3057.
(Continued)

*Primary Examiner* — Christopher Koharski
*Assistant Examiner* — Gabriel Victor Popescu
(74) *Attorney, Agent, or Firm* — Calderon Safran & Cole PC

(57) ABSTRACT

This disclosure generally relates to stable water isotope labeling followed by detection via MRI (swiMRI), including
(Continued)

Deuterium CSI spectrum overlaid on anatomical/proton MRI image, obtained on day +28 following AHSCT, after 21 days of $^2H_2O$ labeling to 5% TBW, probe version 4.0, 3 slices, 3-mm each; 5% $^2H_2O$ phantom scanned simultaneously (reference)

deuterium MRI (dMRI) and $^{17}$O MRI, for visualizing rapidly dividing immune cells within target and/or lymphoid organ/s and/or tissues affected by chronic graft-versus-host disease (cGVHD). Using deuterated water labeling, followed by dMRI, a distinction in deuterium signal was detected in a target organ (e.g. liver) of the cGVHD-affected mice compared to unaffected mice, i.e. syngeneic HSCT recipient mice, where the host and donor are matched, and normal (unmanipulated) mice.

14 Claims, 31 Drawing Sheets

(51) Int. Cl.
- *G01R 33/34* (2006.01)
- *G01R 33/36* (2006.01)
- *G01R 33/48* (2006.01)

(52) U.S. Cl.
CPC . *G01R 33/34061* (2013.01); *G01R 33/34069* (2013.01); *G01R 33/34092* (2013.01); *G01R 33/3635* (2013.01); *G01R 33/4828* (2013.01); *A61B 2503/40* (2013.01)

(58) Field of Classification Search
CPC ........ G01R 33/34069; G01R 33/34092; G01R 33/3635; G01R 33/4828
See application file for complete search history.

(56) References Cited

U.S. PATENT DOCUMENTS

| | | | |
|---|---|---|---|
| 5,552,707 A | 9/1996 | Takahashi et al. | |
| 5,929,639 A | 7/1999 | Doty | |
| 7,596,402 B2* | 9/2009 | Duerk | G01R 33/287 600/423 |
| 7,608,248 B2* | 10/2009 | Kainosho | G01R 33/465 424/9.34 |
| 2002/0145427 A1 | 10/2002 | Wong et al. | |
| 2003/0211036 A1* | 11/2003 | Degani | A61B 5/0263 424/1 |
| 2006/0127313 A1* | 6/2006 | Goldman | A61K 49/10 424/9.3 |
| 2008/0051649 A1* | 2/2008 | O'Dell | A61B 5/055 600/410 |
| 2008/0297156 A1 | 12/2008 | Suematsu et al. | |
| 2015/0141804 A1* | 5/2015 | Rooney | G01R 33/4828 600/419 |

OTHER PUBLICATIONS

Farthing, D.E. "Sensitive GC-MS/MS method to measure deuterium labeled deoxyadenosine in DNA from limited mouse cell populations." Analytical chemistry vol. 85,9 (2013): 4613-20. doi:10.1021/ac400309d.

* cited by examiner

Schematic representation of CD4+ T cell distribution and predominant subtype by cohort
day +28, flow cytometry data

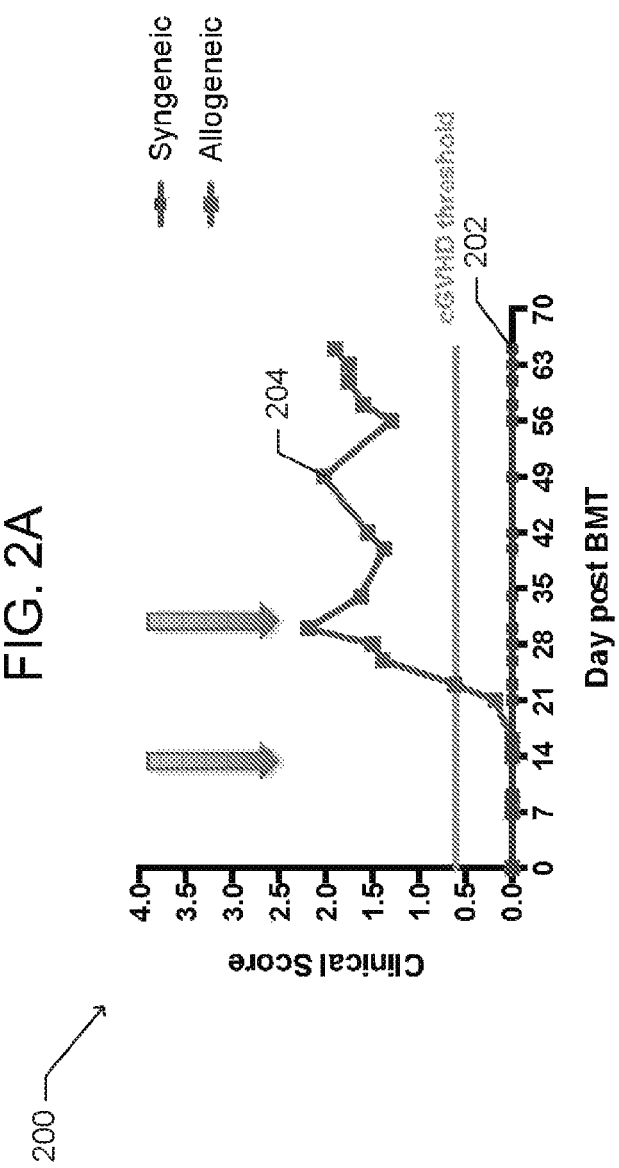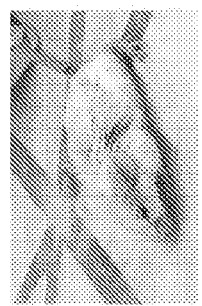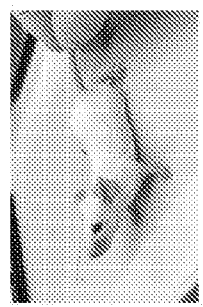

dMRI of syngeneic (A) vs. allogeneic (B) HSCT recipients at day +28, following 21 days of in vivo deuterium labeling to 5% TBW 9.4T, CSI mode, probe version 2.0, 8-mm slice Spectroscopic deuterium signal in mouse tumor cells labeled with deuterated water during culture $^2H_2O$ phantom/solution 0.015% (red) compared to purified DNA extracted from ~3.8 million JRM4 cells (blue). JRM4 cells (mouse tumor cells) were cultured in 20% $^2H_2O$, resulting in ~50% enrichment in dA, purified with Promega Maxwell 16 (no intracellular unbound $^2H_2O$ present)

Schematic of a single saddle coil (1/2 of the quadrature 2-H coil)

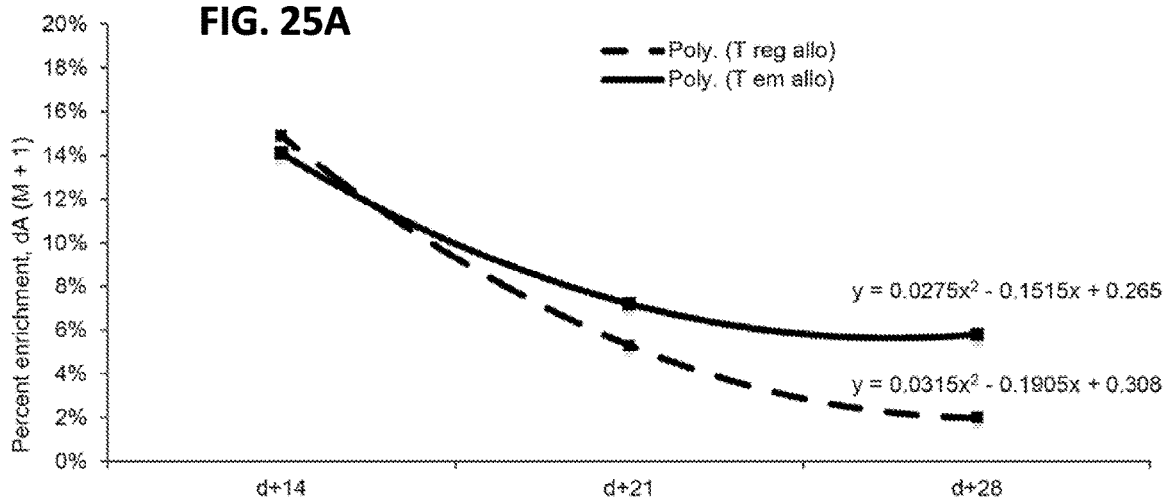
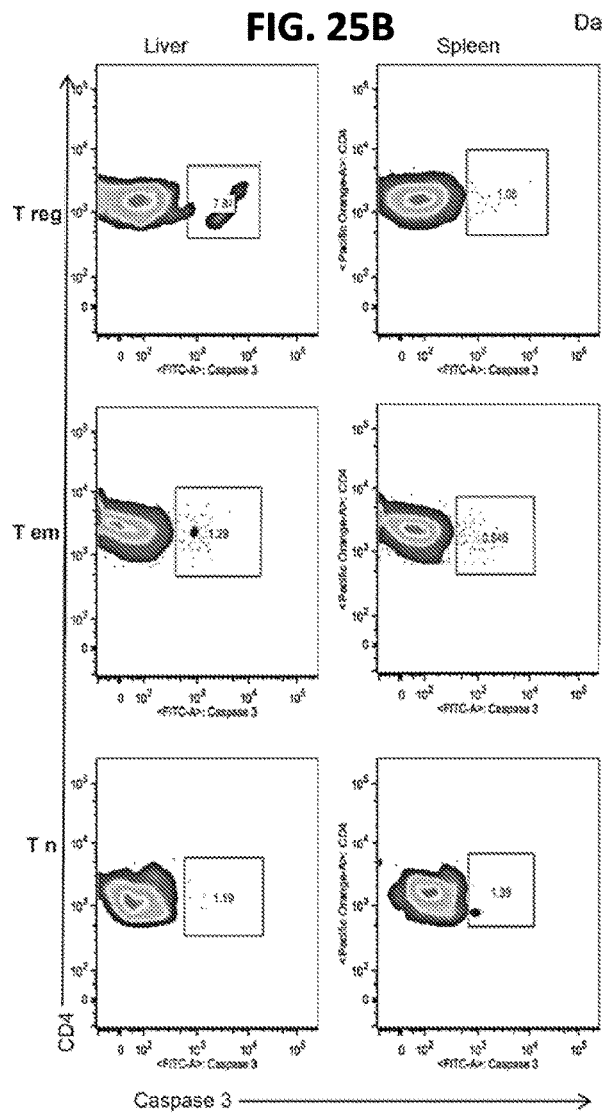
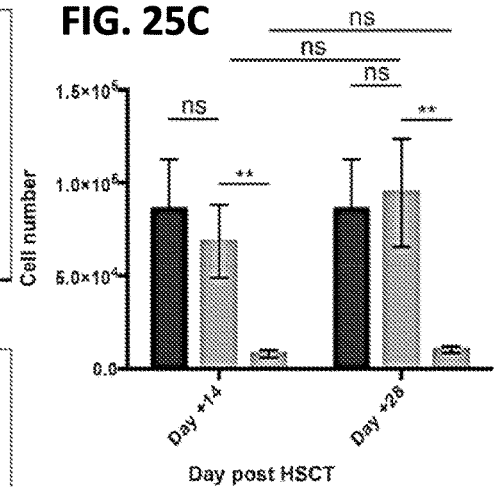
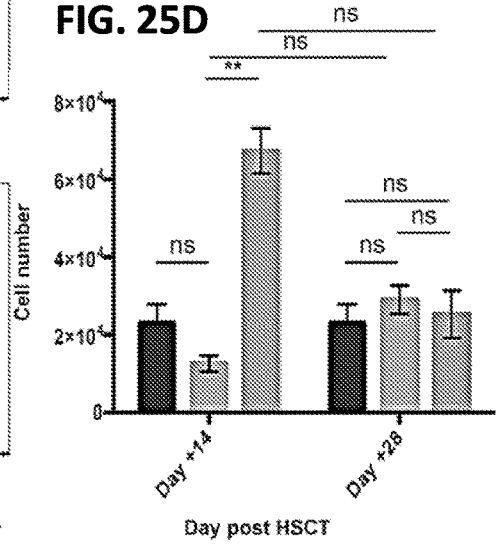

STABLE WATER ISOTOPE LABELING AND MAGNETIC RESONANCE IMAGING FOR VISUALIZATION OF THE PRESENCE OF AND PREDICTION OF THE LIKELIHOOD OF OCCURENCE OF RAPIDLY DIVIDING CELLS

CROSS REFERENCE TO RELATED APPLICATIONS

This application is a national stage application of International Application No. PCT/US2017/058856 filed Oct. 27, 2017, which claims the benefit of U.S. Provisional Application No. 62/414,554, filed Oct. 28, 2016, the applications are herein incorporated by reference in its entirety.

GOVERNMENT INTEREST STATEMENT

The present subject matter was made with U.S. government support. The U.S. government has certain rights in this subject matter.

FIELD

The present disclosure relates to systems, methods, and devices for the non-radioactive visualization of rapidly dividing cells using stable water isotope labeling followed by detection via stable isotope nuclear magnetic resonance imaging.

BACKGROUND

The identification and treatment of diseases and/or conditions characterized by the presence of rapidly dividing cells is often delayed by the need to perform a biopsy before making an initial diagnosis. Performing a biopsy can be an invasive procedure, particularly when tissue must be collected from internal organs. By the time such a diagnosis is made, the disease or condition has progressed. For example, chronic graft-versus-host disease (cGVHD) is a prevalent and highly morbid condition affecting allogeneic hematopoietic stem cell transplant ("allogeneic HSCT" or "AHSCT") recipients. Currently, there are no diagnostic imaging features or validated biomarkers predictive of impending or active cGVHD. It is known that biopsies performed on HSCT recipients are risky and difficult, as these patients are often on systemic immunosuppression.

Early detection of cGVHD and other diseases or conditions characterized by the presence of rapidly dividing cells, such as cancer or infection, would likely improve the long-term prognosis of the patient. Non-invasive methods for such early detection are desirable to limit the need for invasive biopsies only to confirm initial findings and minimize additional physical impact on the patient.

SUMMARY

The systems, methods, and devices of the present disclosure generally relate to the early detection of chronic graft-versus-host disease (cGVHD) and other diseases or conditions characterized by the presence of rapidly dividing cells, such as, but not limited to cancers, infections, and autoimmune diseases. In one aspect, a method for NMR/MRI imaging to predict or detect an occurrence of graft-versus-host disease in a subject includes providing a stable water isotope enriched fluid and administering the stable isotope enriched fluid to the subject. The method also includes allowing the stable water isotope from the enriched fluid to incorporate into rapidly dividing cells of the subject over a period of time and determining the enrichment level of stable water isotope in a total body water of the subject. The enrichment level is determined at at least one of: before, during, or after the period of time.

The method further includes positioning the subject within a magnetic field of an energized NMR/MRI system. The NMR/MRI system includes a probe tuned to measure a resonance frequency of the stable water isotope and a resonance frequency of a proton (H). The method also includes performing magnetic resonance imaging (MRI) to detect a level of stable water isotope enrichment in the rapidly dividing cells contained within one or more organs or tissue of the subject; wherein the level of stable water isotope enrichment in the rapidly dividing cells is greater than a background enrichment of the stable water isotope in the total body water of the subject. The method further involves comparing the concentration of the stable water isotope in the one or more organs or tissue of the subject to a control subject, where the control subject does not have graft-versus-host disease; and, lastly, diagnosing the occurrence or a likelihood of occurrence of graft-versus-host disease prior to or during the clinical presentation of graft-versus-host disease symptoms in the subject.

The present disclosure also relates to an NMR/MRI probe for use in an magnetic resonance imaging system. In one aspect, the NMR/MRI probe includes a first radiofrequency coil including dual parallel rectangular loops. The rectangular loops each have a loop capacitor. The probe also includes a second radiofrequency coil comprising at a pair of double saddle coils; where each pair of the double saddle coils is connected in series with an in-line capacitor.

Additional objectives, advantages, and novel features will be set forth in the description that follows or will become apparent to those skilled in the art upon examination of the drawings and detailed description that follows.

BRIEF DESCRIPTION OF THE DRAWINGS

FIG. 2A is a graph depicting clinical scores relating to cGVHD symptoms for syngeneic HSCT recipients and allogeneic HSCT recipients, according to one embodiment.

FIGS. 2B and C are photographs of mice at different time points post HSCT that correspond to the clinical scores for allogeneic HSCT recipients provided in FIG. 2A, according to one embodiment;

FIGS. 25A-25D include charts and graphs presenting label loss kinetics for $T_{Reg}$ cells in the liver appear to be driven by increased propensity for apoptosis rather than trafficking, according to one embodiment;

Reference characters indicate corresponding elements among the view of the drawings. The headings used in the figures do not limit the scope of the claims.

DETAILED DESCRIPTION

Figure 1A:
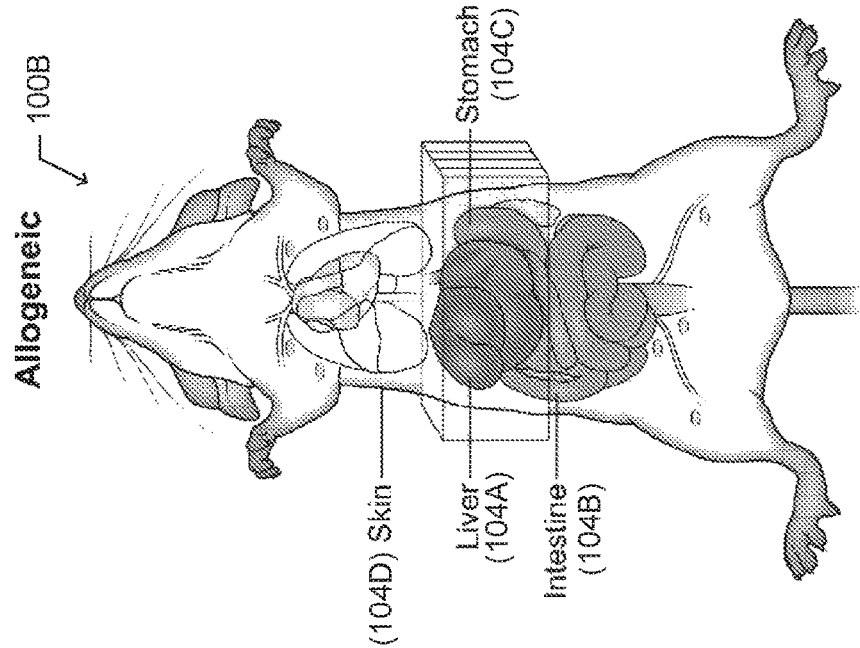
FIGS. 1A and 1B depict anatomical drawings of mice that received hematopoietic stem cell transplantation (HSCT), according to one embodiment.

The present disclosure generally relates to the early detection of chronic graft-versus-host disease (cGVHD) and other diseases or conditions characterized by the presence of rapidly dividing cells, such as, but not limited to cancers, infections, and autoimmune diseases. In particular, the present disclosure describes improved systems and methods for labeling whole organisms, and/or organs, and/or cells with stable water isotopes, including hydrogen and oxygen, (i.e. deuterium ($^2$H) and heavy oxygen ($^{17}$O)) followed by magnetic resonance imaging for the stable water isotope (e.g. deuterium MRI (dMRI) and/or $^{17}$O MRI), for visualization of rapidly dividing cells. The present disclosure also relates to the use of deuterium and oxygen stable water isotopes as labeling agents for imaging patients post allogeneic hematopoietic stem cell transplantation ("allogeneic HSCT" or "AHSCT") for diagnosing of early and/or ongoing cGVHD. While the systems and methods are primarily disclosed and described regarding the use of deuterium ($^2$H), the systems and methods may be configured for use with either deuterium ($^2$H), heavy oxygen ($^{17}$O), or both. Other stable water isotopes may also be used. Stable water isotope MRI (swiMRI), as used herein, encompasses both, dMRI and $^{17}$O MRI. In one aspect, swiMRI may include the simultaneous imaging of deuterium and heavy oxygen. In other aspects, the stable water isotopes may be imaged separately.

Rapidly dividing cells, as used herein, may include, but are not limited to, T cells and other immune cells that infiltrate target organs affected by cGVHD. In the various embodiments disclosed, swiMRI allows early detection of cGVHD in a non-radioactive and inexpensive manner, and allows for the diagnosis and monitoring of active or ongoing cGVHD. Alternatively, as deuterium preferentially incorporates into rapidly dividing cells, swiMRI may be used for non-invasive in vivo tumor imaging, including visualization of neoplastic/cancer cells. The systems and methods of the present disclosure offer inexpensive and non-radioactive alternatives to positron emission tomography (PET).

In another aspect, according to various embodiments disclosed herein, swiMRI may allow visualization and localization of immunotherapeutic products following infusion into an animal or human subject. Examples of such products include chimeric antigen receptor T cells (CAR T cells), tumor infiltrating lymphocytes (TILs), and other adoptive immunotherapies, if such products undergo stable water isotope labeling in culture (during manufacture).

In another aspect, the present disclosure also relates to a specially configured nuclear magnetic resonance (NMR)/magnetic resonance imaging (MRI) coil or probe. In particular, the coil is multi-tuned to detect signals from hydrogen, deuterium, and oxygen isotopes, and combinations thereof simultaneously.

Pre-Clinical Modeling

A pre-clinical mouse model of cGVHD was used to quantitatively measure in vivo kinetics of fluorescence-activated cell sort (FACS) purified T cell subsets extracted from cGVHD-affected organs. Some underlying principles of the model were derived from studies using gas chromatography-tandem mass spectrometry (GC-MS/MS) methods for measuring deuterium-labeled deoxyadenosine in DNA extracted from T cell subsets, published as Sensitive GC-MS/MS method to measure deuterium labeled deoxyadenosine in DNA from limited mouse cell populations; by Farthing, D. E. et al., Anal. Chem. 85, 4613-4620 (2013) which is incorporated herein by reference in its entirety. Additional underlying principles of the models were derived from studies contained in the draft manuscript entitled "Just add water: T cell subset kinetics and deuterium MRI of graft-versus-host disease"; by Buxbaum, N. P. et al., which is and incorporated herein by reference in its entirety from U.S. Provisional Application No. 62/414,554, filed Oct. 28, 2016.

In one aspect, the biology of cGVHD in the pre-clinical model and similarly in patients is mediated by T cells. Specifically, the genetic differences between host and donor drive donor T cells to recognize host tissues as foreign, which results in a multi-organ inflammatory disease in the host organs and tissues—commonly referred to as graft-versus-host disease. While cGVHD is mediated by T cells, the in vivo cell processes of T cell division, death, and trafficking are not well characterized. In clinical studies, peripheral blood is amenable to investigation, but T cell populations found in the blood may not accurately reflect T cell composition in target and/or lymphoid organs and tissues. Therefore, the disclosed mouse model was useful in evaluating T cells in blood, lymphoid, and target organs at sequential biologically relevant time points following transplantation. The relevant time points include pre-symptomatic early events in cGVHD pathogenesis (day +14) to clinically apparent cGVHD (day +28). A differential distribution of T cell subsets in cGVHD (AHSCT, where the host and donor are purposefully mismatched at minor immune antigens) versus immune reconstitution without cGVHD (syngeneic hematopoietic stem cell transplant (HSCT), where the host and donor are genetically identical) was identified.

Figure 1B:
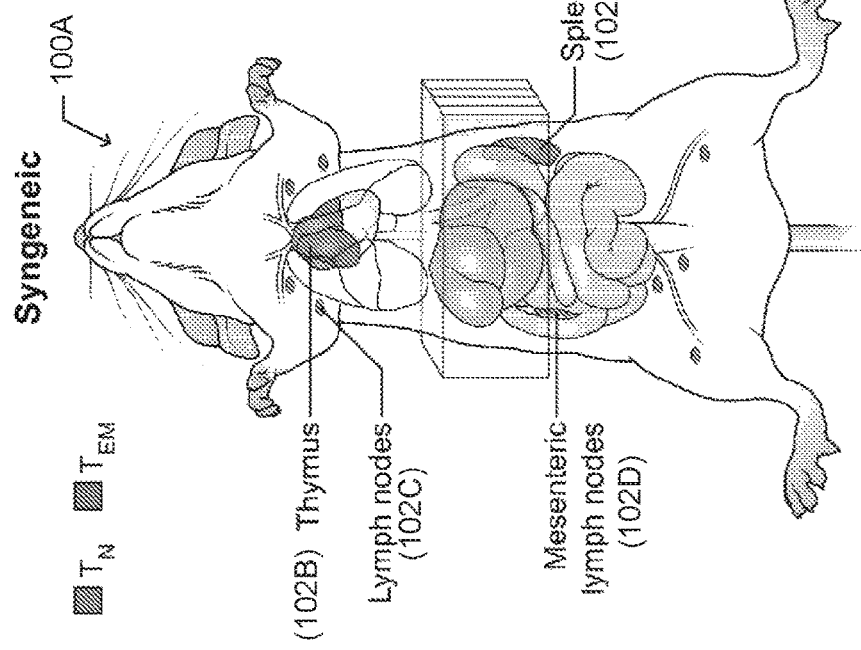

FIGS. 1A-B are graphic representations of CD4+ T cell distributions in the syngeneic HSCT setting (control) and allogeneic HSCT (cGVHD affected) mice at day +28 following HSCT. In particular, FIG. 1A depicts a mouse 100A that underwent syngeneic (matched) HSCT, while FIG. 1B is a depiction of a mouse 100B that underwent allogeneic (mismatched) HSCT and developed cGVHD. The representations identify the organs and tissues that have the highest number of CD4+ T cells in each cohort and the most prevalent CD4+ T cell subset found in those organs and tissues. In the syngeneic HSCT recipients (FIG. 1A), CD4+ T cells are primarily of the naïve phenotype and are found in lymphoid organs and tissues, including but not limited to the spleen 102A, thymus 102B, and lymph nodes 102C and 102D. In contrast, in the allogeneic HSCT recipients (FIG. 1B), CD4+ T cells are primarily of the effector memory phenotype and are found in the target organs and tissues, including but not limited to the liver 104A, gastrointestinal tract 104B and 104C, and the skin 104D, but not in the lymphoid ones. Of note, the CD4+$T_{EM}$ cells found in the target organs and tissues 104A-D of allogeneic HSCT recipients were found to have high DNA deuterium enrichment levels (15-20%), when labeled to 5% total body water (TBW) for days and up to weeks following infusion of an HSCT graft.

Besides localization differences between syngeneic and allogeneic HSCT recipients, the types of CD4+ T cells differ between two cohorts. Specifically, the predominant phenotype of CD4+T cells in the syngeneic recipient mice is T naïve ($T_N$); while in the allogeneic recipient, the phenotype is primarily T effector memory ($T_{EM}$).

Data from the pre-clinical model of cGVHD to study T cell populations in vivo is provided in FIGS. 1A-B and FIGS. 2A-C. FIG. 2A is a graph 200 depicting clinical scores relating to cGVHD symptoms for syngeneic HSCT recipients 202 and allogeneic HSCT recipients 204, according to one embodiment. The clinical scores are determined based on presence of erythema (redness) and scaling on the ears, tails, and paws, and surface area of skin affected by alopecia (hair loss). The mice in the allogeneic group were driven to cGVHD by minor deliberate mismatching between the donor and host, while the mice in the syngeneic cohort were matched to the donor. Each group was subject to a total body irradiation (TBI) conditioning regimen performed one day before the infusion of the transplant graft. FIGS. 2B and 2C are photographs of mice at different time points post HSCT that correspond to the clinical scores 204 in FIG. 2A.

The organs and compartments affected by cGVHD in the pre-clinical mouse model were studied using flow cytometry, immunohistochemistry (IHC), in vivo kinetics, or combinations thereof, as described more fully below in the section under the heading: An Analysis of T-cell kinetics and a Working Example of T-cell Labeling and deuterium MRI imaging of cGVHD. In particular, flow cytometry and IHC were used to observe cGVHD in the skin, small intestine (i.e. duodenum, jejunum, ileum, and cecum), liver, spleen, thymus, and lymph nodes. Peripheral blood was assessed by flow cytometry. In vivo kinetics studies were performed on purified CD4+ T cell subsets extracted from the spleen (lymphoid organ) and liver (cGVHD target organ) of syngeneic and allogeneic HSCT recipient mice.

Figure 3:
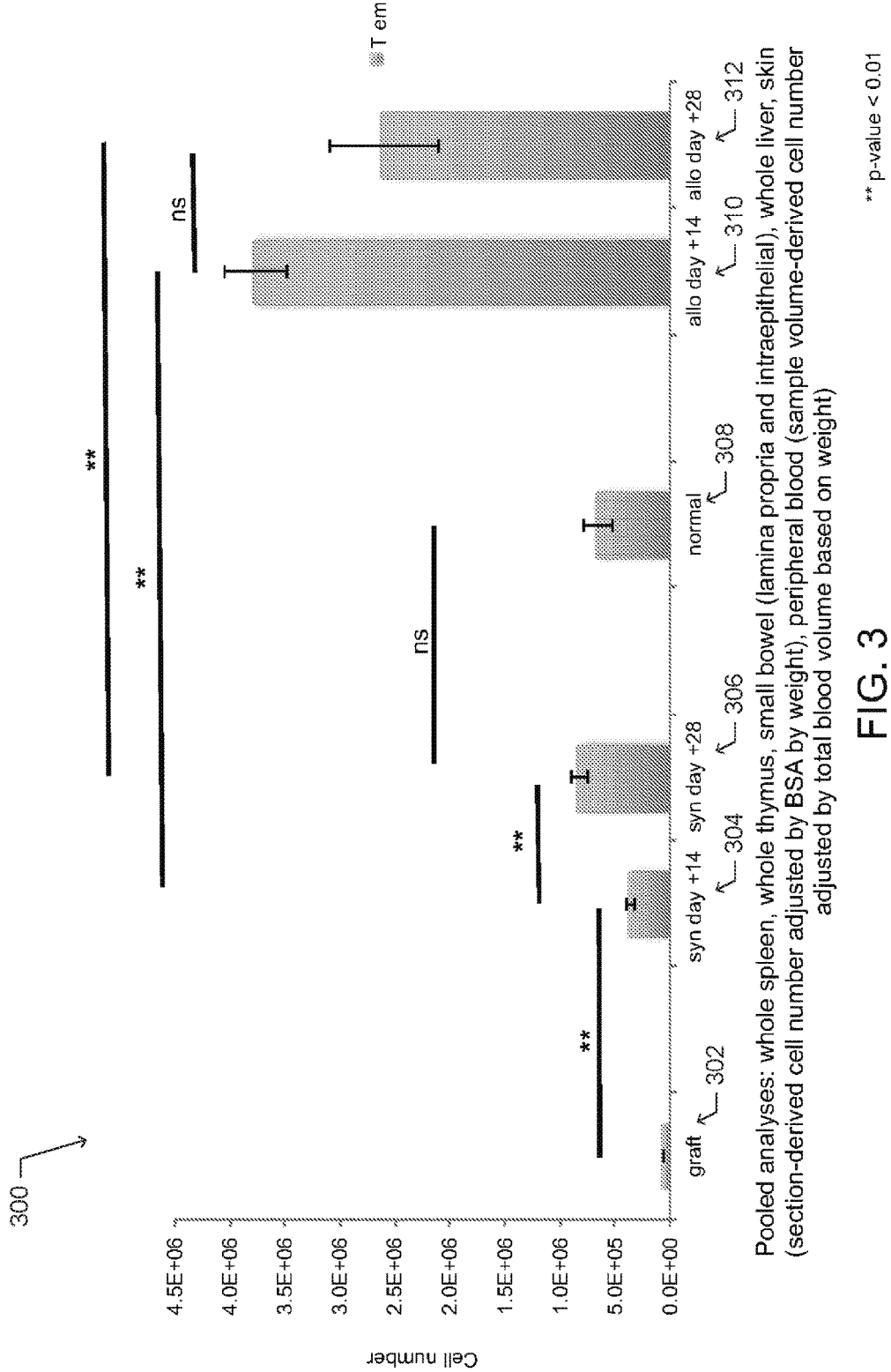
FIG. 3 is a bar graph depicting the collective number of CD4+ T effector memory ($T_{EM}$) cells extracted from mouse organs and tissues from each described cohort (graft, syngeneic HSCT recipient, normal mouse, allogeneic HSCT recipient), according to one embodiment.
Figure 4:
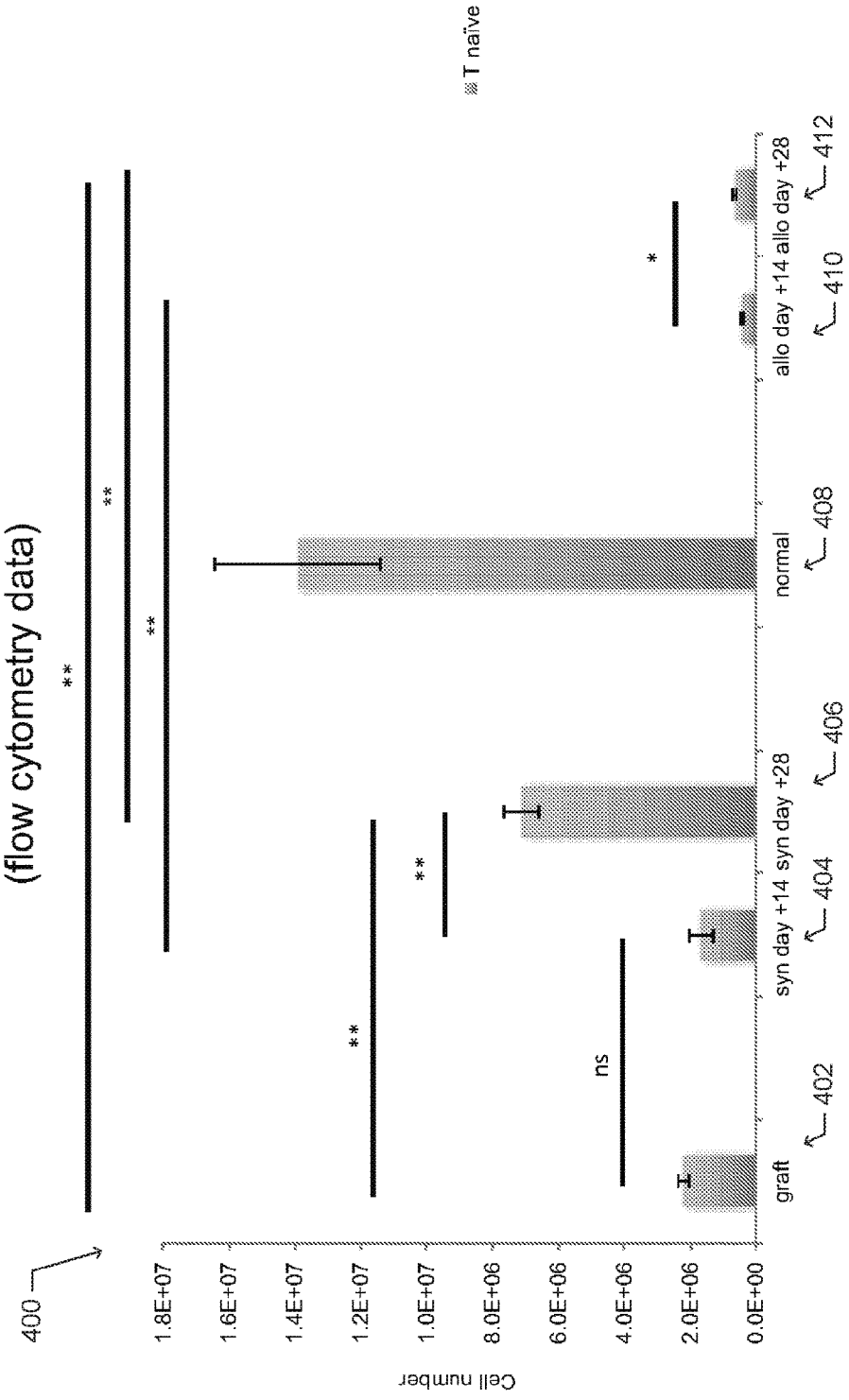
FIG. 4 is a bar graph depicting the collective number of CD4+ T naïve ($T_N$) cells extracted from mouse organs and tissues from each described cohort (graft, syngeneic HSCT recipient, normal mouse, allogeneic HSCT recipient), according to one embodiment.

Additional observations are shown in FIGS. 3 and 4. The graph 300 of FIG. 3 depicts the collective number of CD4+ T effector memory ($T_{EM}$) cells extracted from mouse organs and tissues from each described cohort (graft 302, syngeneic HSCT recipient 304-306, normal mouse 308, and allogeneic HSCT recipient 310-312. In one aspect, the graft 302 is made from bone marrow and spleen of the donor and the number of CD4+$T_{EM}$ cells in the graft was determined by flow cytometry.

For the normal (untransplanted) mice, syngeneic HSCT recipients, and allogeneic HSCT recipients, CD4+$T_{EM}$ cells were extracted from the whole spleen, the whole thymus, the small bowel (lamina propria and intraepithelial layer), the whole liver, the skin and peripheral blood. The total number of skin-resident CD4+$T_{EM}$ cells was determined in by counting the number of CD4+$T_{EM}$ cells in a 1 cm² sample and determining the total body surface area based on weight. Similarly, the number of CD4+$T_{EM}$ cells in a blood sample volume and the total blood volume based on weight were used to calculate the total number of CD4+$T_{EM}$ cells in circulation.

The graph 400 of FIG. 4 depicts the collective number of CD4+ T naïve ($T_N$) cells extracted from mouse organs and tissues from each described cohort (graft 402, syngeneic HSCT recipient 404-406, normal mouse 408, allogeneic HSCT recipient 410-412). In one aspect, the graft 402 is made from bone marrow and spleen of the donor and the number of CD4+ $T_N$ cells in the graft was determined by flow cytometry. For the normal (untransplanted) mice, syngeneic HSCT recipients, and allogeneic HSCT recipients, CD4+ $T_N$ cells were extracted from whole spleen, whole thymus, small bowel (lamina propria and intraepithelial layer), whole liver, skin and peripheral blood. The total number of skin-resident CD4+ $T_N$ cells was determined in by counting the number of CD4+ $T_N$ cells in a 1 cm² sample and determining the total body surface area based on weight. Similarly, the number of CD4+ $T_N$ cells in a blood sample volume and the total blood volume based on weight were used to calculate the total number of CD4+ $T_N$ cells in circulation.

As shown, the number of CD4+$T_{EM}$ cells is higher in the allogeneic HSCT cohort compared to the other cohorts, as shown FIG. 3. The number of CD4+ T naïve ($T_N$) cells increases over the course of syngeneic immune reconstitution, while the number of $T_N$ cells in the allogeneic HSCT remains low, as shown in FIG. 4. Concurrently, a differential distribution of CD4+ T cell subsets in cGVHD-affected animals compared to unaffected mice is observed, as shown in FIGS. 1A-B.

Deuterated Water Labeling

According to various embodiments, deuterium was provided for uptake into rapidly dividing cells for subsequent detection via deuterium chemical shift imaging (CSI), a type of magnetic resonance imaging, also referred to herein as dMRI. Quantitative measurements of in vivo T cell kinetics in lymphoid and target organs were obtained by applying deuterated water labeling and de-labeling post HSCT, followed by extraction and purification of T cell subsets from target and lymphoid organs, then quantitatively measuring deuterium labeled and unlabeled fractions of deoxyadenosine (DNA base pair). Fraction of newly divided cells was then mathematically determined.

In one aspect, deuterium labeling was achieved by intraperitoneal injection of 100% $^2H_2O$ with NaCl added to make this fluid isotonic, then maintaining the achieved 5% $^2H$ enrichment in total body water (TBW) by providing 8% $^2H_2O$ in drinking water to mice. Deuterium within total body water diffuses rapidly into all tissues and is excreted unchanged by the kidneys. Therefore, according to various embodiments, deuterium labeled fluids may be provided to an animal or human subject via injected and/or ingested fluid yielding a deuterium concentration of about 5% TBW. In various other embodiments, higher enrichments of the deuterium labeling up to and including approximately 20% TBW have been safely achieved. Higher TBW enrichments (up to 20% TBW $^2H$) may improve sensitivity of dMRI detection. Such enrichments should be safe, as deuterium is non-radioactive, tasteless, colorless and without known side effects at these doses.

The provided deuterium incorporates into the DNA of dividing cells constitutively through the de novo nucleoside synthesis pathway, as described in *Measurement of cell proliferation by heavy water labeling*; by Busch, R. et. al., Nat Protoc 2, 3045-3057 (2007). High enrichment of deuterium (15-20%) in cellular DNA of rapidly diving cells, i.e. CD4+ T effector memory cells (Tem) in cGVHD target organ (liver), was measured in the disclosed cGVHD mouse model following TBW labeling to 5% for 7 days by measuring $^2H$ labeled and unlabeled dA in cellular DNA using gas chromatography and tandem mass spectrometry (GC-MS/MS), as shown in FIG. 5.

Figure 5:
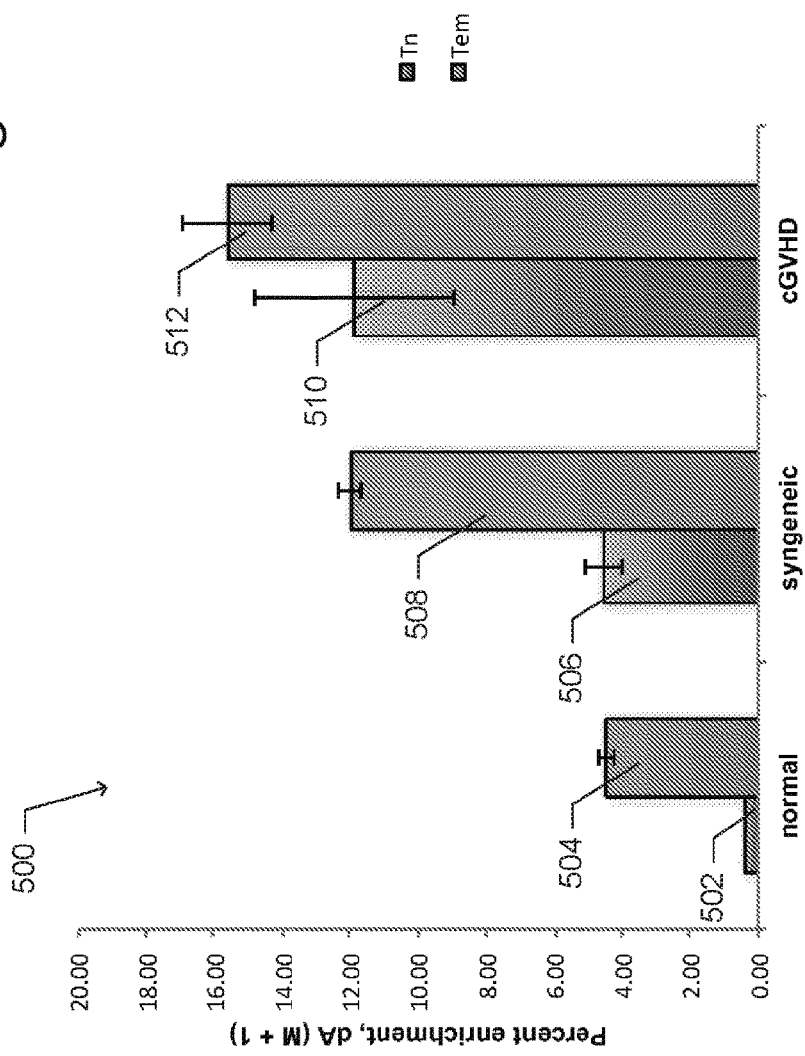
FIG. 5 is a graph depicting deuterium enrichment in normal (unmanipulated) mice, syngeneic HSCT recipients, and allogeneic HSCT recipients that developed cGVHD, according to one embodiment.

FIG. 5 is a graph 500 depicting deuterium enrichment in deoxyadenosine (dA), a DNA base pair, of CD4+ T cells, either $T_N$ 502, 506, and 510 or $T_{EM}$ 504, 508, 512, extracted from liver parenchyma of normal (unmanipulated) mice, syngeneic HSCT recipients, and allogeneic HSCT recipients that developed cGVHD, respectively. For each cohort, the enrichment in dA was measured via GC-MS/MS following 1 week of in vivo deuterium labeling to 5% in total body water. In one aspect, varied labeling and de-labeling periods may measure deuterium gain and loss from cellular DNA via GC-MS/MS.

Figure 13:
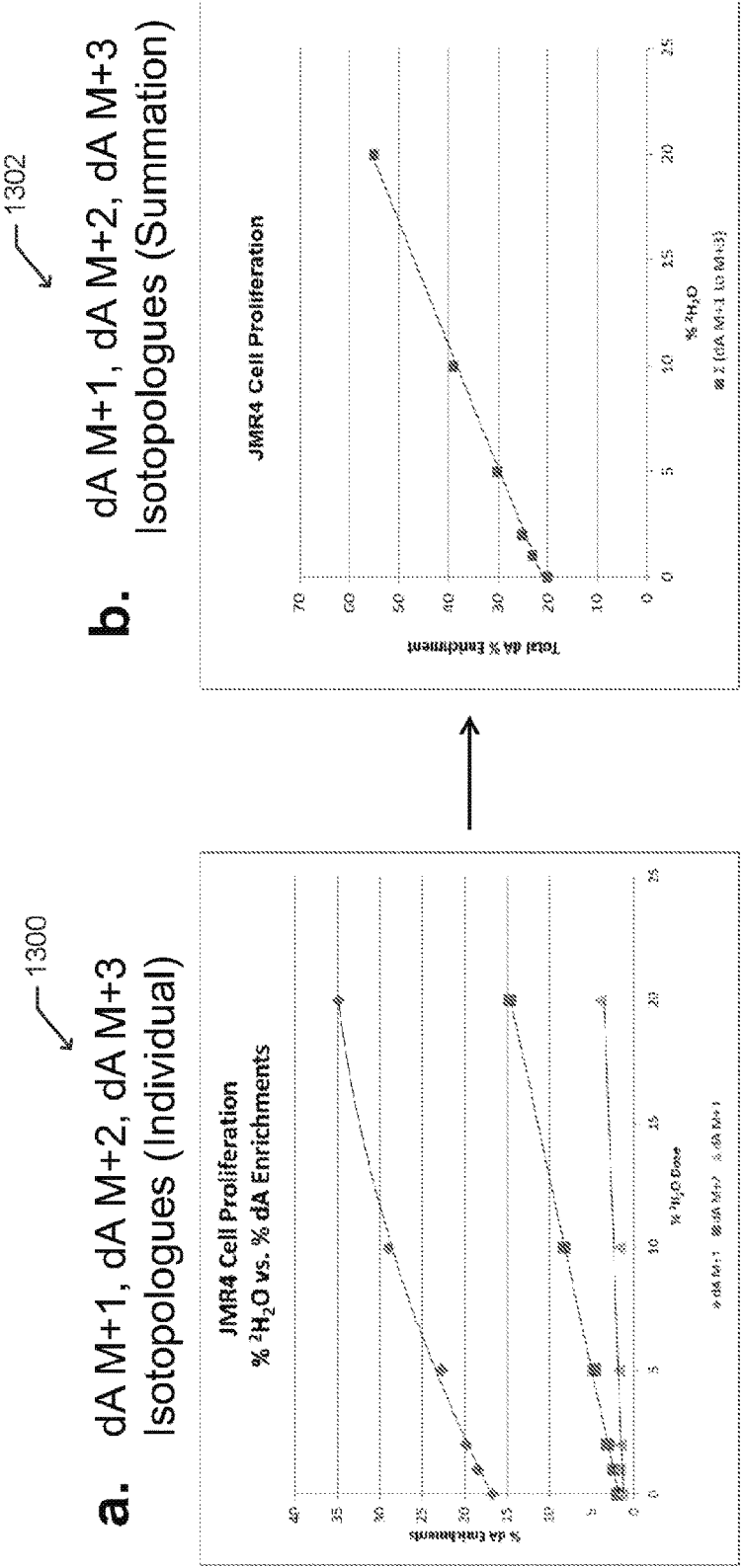
FIGS. 13A-13B includes graphs illustrating deuterium dosing with resultant isotopic enrichment in DNA base pairs (isotopologues), according to one embodiment.

FIG. 13 includes graphs 1300 and 1302 of $^2H_2O$ dose and isotopic enrichments in DNA base pairs, such as dA isotopologues. As shown, increasing the $^2H_2O$ level in TBW (or culture media) results in nearly linear increases in deuterium incorporation into DNA base pairs.

In one aspect, an advantage of using stable water isotopes, such as deuterated water ($^2H_2O$), over other methods of cell division measurements, such bromodeoxyuridine (BrdU), tritiated thymidine, or carboxyfluorescein succinimidyl ester (CFSE), is that deuterium is non-radioactive, safe, and non-toxic at doses up to 20% in total body water. Deuterium does not affect rates of DNA synthesis and no ex vivo labeling is required.

Figure 6:
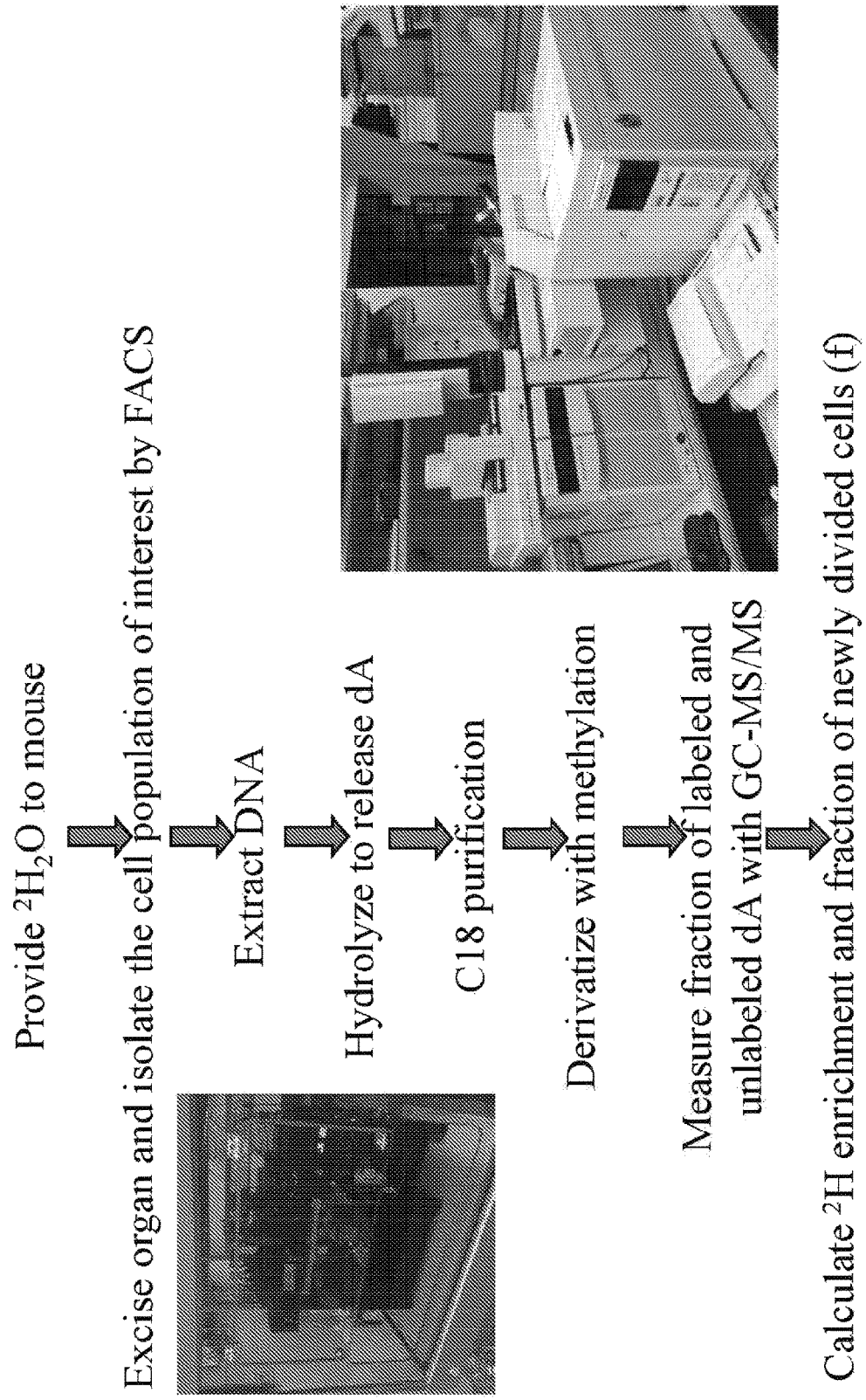
FIG. 6 is a flow diagram depicting a method for labeling mice with deuterium and determining the deuterium enrichment in rapidly dividing cells in such mice, according to one embodiment.

FIG. 6 is a flow chart depicting one embodiment of a method for determining the deuterium enrichment in DNA of rapidly dividing cells in mice after labeling. As shown, the method includes the steps of providing $^2H_2O$ to a mouse via intraperitoneal injection, then in the drinking water, followed by excision of the organ of interest to isolate the desired cell population by fluorescence-activated cell sorting (FACS). Next, DNA is extracted, hydrolyzed to release deoxyadenosine (dA), and then purified using a C-18 column. The purified DNA is derivatized by methylation. Fractions of the labeled and unlabeled dA are then measured using GC-MS/MS, an example of such enrichment in dA is shown in FIG. 5. Lastly, once the level of deuterium enrichment is measured, the fraction of the newly divided cells is calculated.

Deuterium Magnetic Resonance Imaging Probe

In various embodiments, a specially configured multi-tuned deuterium probe or coil is used to gather a signal from the deuterium labeled cells, an organ (e.g. liver), or an organism, after in vivo labeling with deuterium. In one particular embodiment, the probe is a quadrature (orthogonal) deuterium probe that provides an improved signal to noise ratio over earlier deuterium probes.

Figure 7:
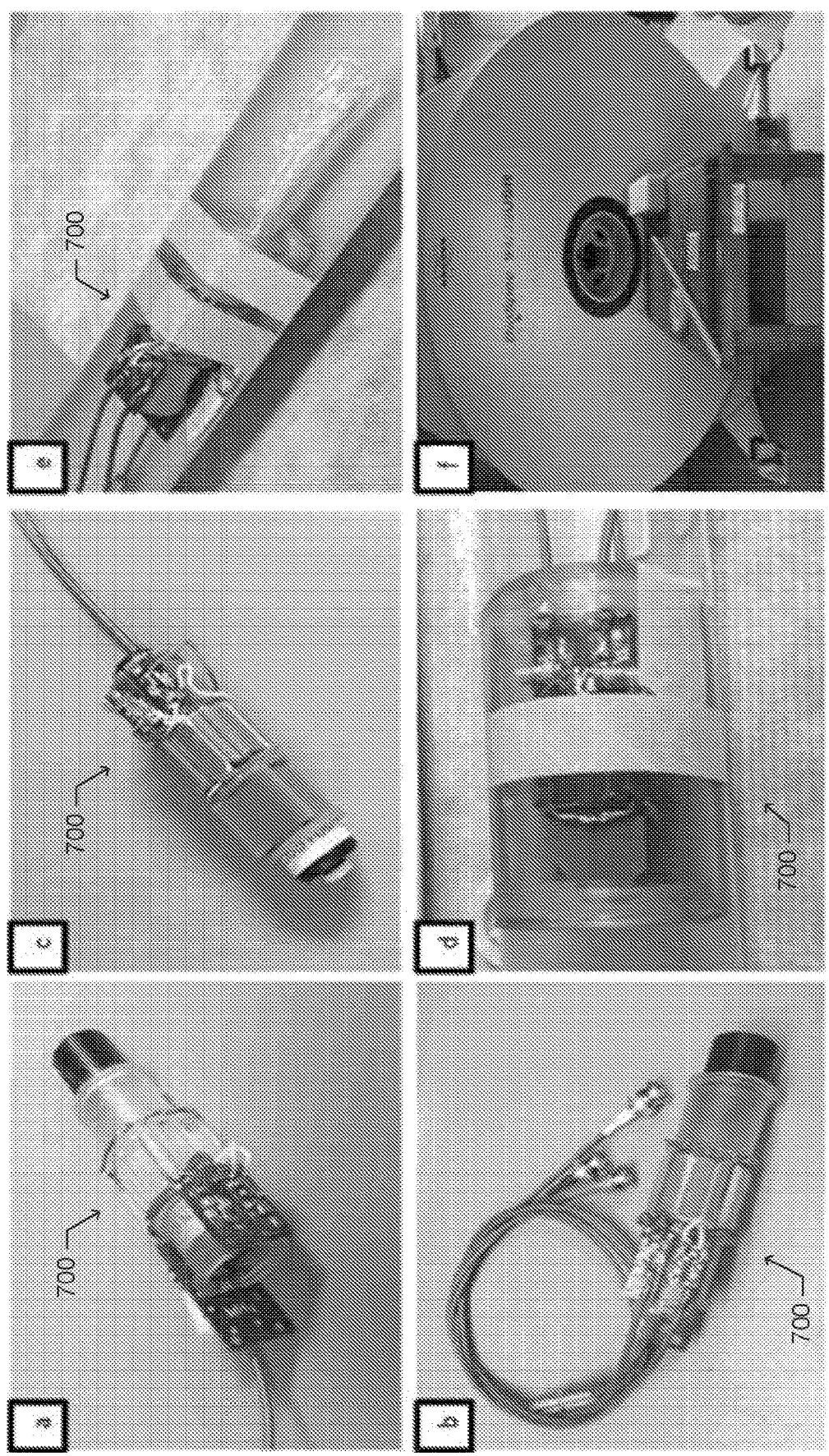
FIGS. 7A-7F include photographs of several prototypes of deuterium probes, and a magnetic resonance imaging (MRI) machine, according to embodiments disclosed herein.

The disclosed deuterium probe has high sensitivity in the deuterium channel and can also obtain images in the hydrogen (proton) channel. Preferably, the proton coil and the deuterium coil create homogeneous radiofrequency fields (B1) within the target volume. FIG. 7 includes photographs (A)-(E) of various embodiments of the multi-tunable dMRI deuterium probe 700 for use with a suitable magnet, including but not limited to the 9.4 Tesla Bruker magnet, shown in FIG. 7(F).

Figure 15:
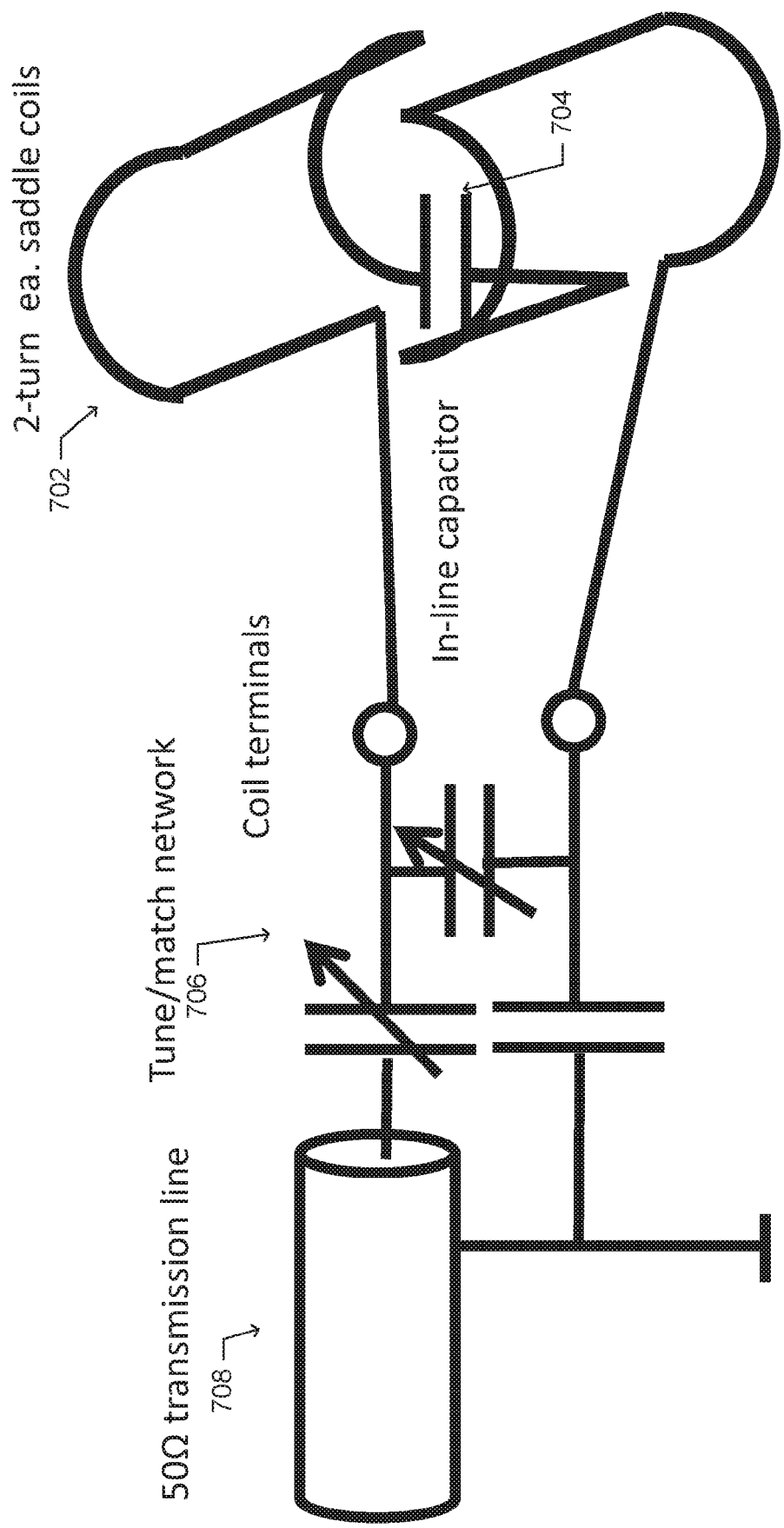
FIG. 15 is a schematic drawing of a single saddle coil of a dual coil dMRI probe, according to one embodiment.

One embodiment of the probe 700 is partially shown in FIG. 15. The probe 800 includes a quadrature deuterium coil 702 and a linear proton coil (not shown) rotated by 45 degrees. The proton coil structure is a "quasi Helmholtz pair" of two parallel rectangular loops with integrated capacitors. The loops are connected in parallel and terminated at the transmission line with an impedance of 50Ω using a balanced tune/match network.

The deuterium coil is composed of two crossed pairs of double saddle coils 702 of 120-degree arc, with each pair connected in series with a single in-line capacitor 704 each. The saddles 702 of the (i) channel and the (q) channel are arranged orthogonally and are isolated to typically less than 0.2% residual coupling. The deuterium coil is also matched and tuned, using a tune/match network 706 and is terminated at a 50Ω impedance transmission line 708.

In various other embodiments, the deuterium probe is substantially similar to the coil disclosed in U.S. Pat. No. 5,323,113, issued on Jun. 21, 1994 to Cory, et al., which is incorporated herein by reference in its entirety. The present probe, however, differs over the probe of U.S. Pat. No. 5,323,113, in that the deuterium probe may be tuned to detect signals from proton, deuterium, and other stable isotopes simultaneously.

Figure 29A:
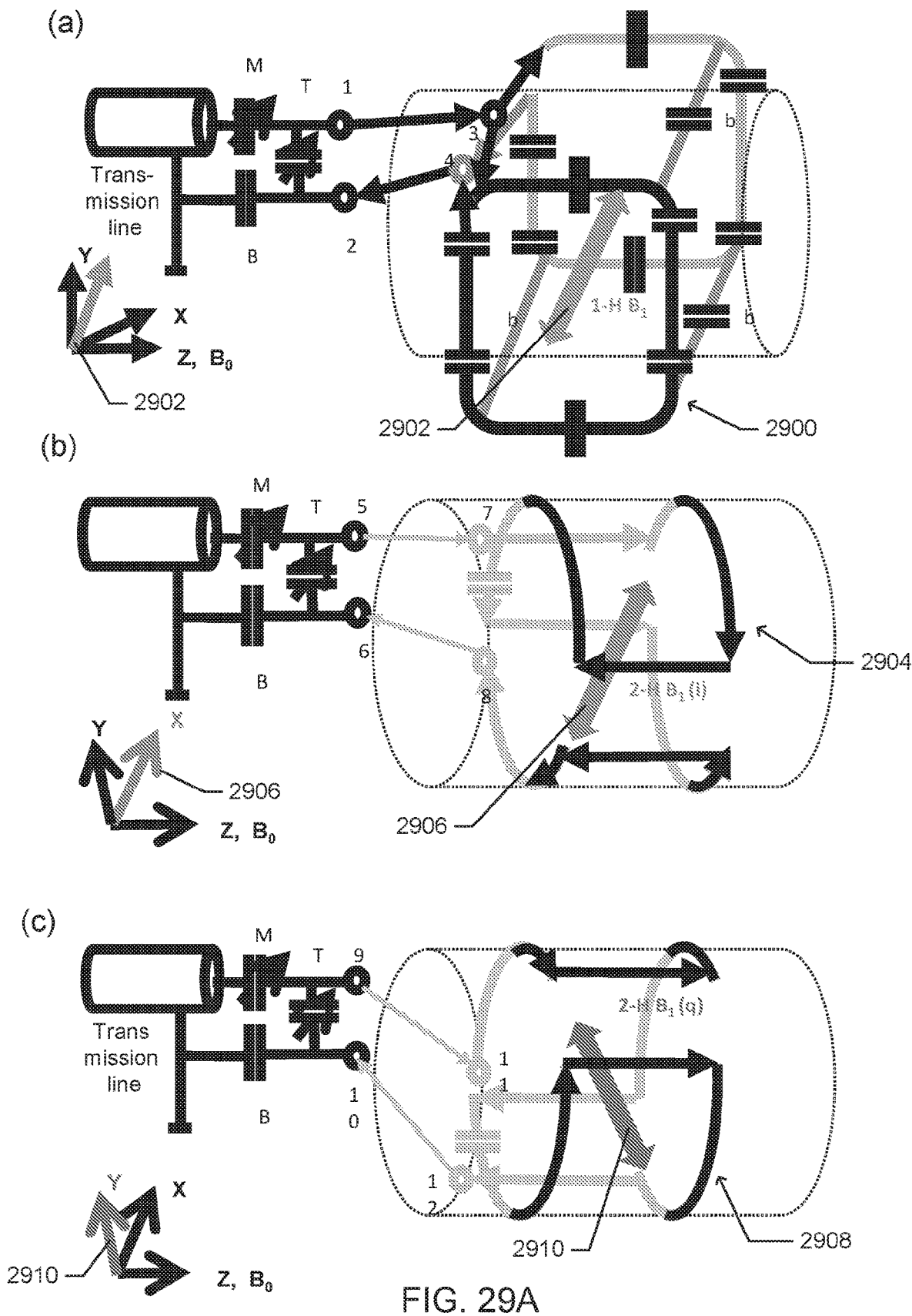
FIGS. 29A-29B includes schematic representations of components of a ($^1$H-$^2$H) proton-deuterium coil, according to one embodiment.
Figure 29B:
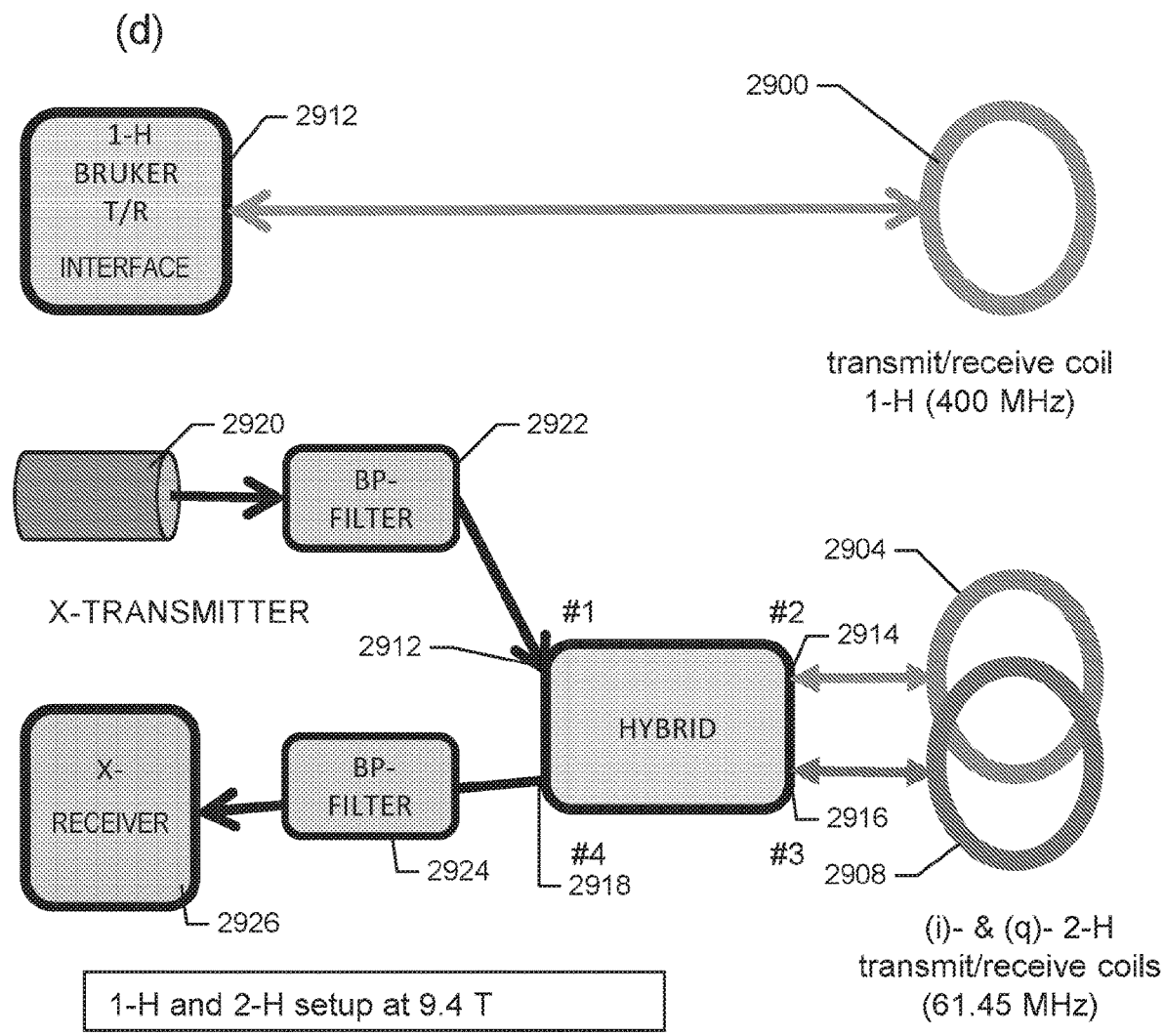

Various other embodiments, or portions thereof, for the multi-tuned probe 700, are shown in FIGS. 29A-B. FIG. 29A (a) is a schematic of the "quasi Helmholtz" $^1$H (proton) transmit/receive coil 2900 for scout (anatomical) imaging. The arrow 2902 indicates the $B_1$ direction in regard to the magnet Cartesian coordinates ($B_0$=Z=horizontal). FIG. 29A (b) is a schematic of the (q)-channel of the "quasi Helmholtz" saddle-type $^2$H transmit/receive coil 2904 for chemical shift imaging (CSI). The double arrow 2906 indicates the $B_1$ direction in regard to the magnet Cartesian coordinates ($B_0$=Z=horizontal). FIG. 29A (c) is a schematic of the (i)-channel of the "quasi Helmholtz" saddle-type $^2$H transmit/receive coil 2908 for CSI. The double arrow 2910 indicates the $B_1$ direction in regard to the magnet Cartesian coordinates ($B_0$=Z=horizontal). FIG. 29B is a schematic of the setup for $^1$H and $^2$H imaging at 9.4 Tesla magnetic flux density. All coils are mounted on a cylindrical former. The 1H (proton) transmit/receive coil 2900, is connected to the MRI system, including the transmit/receive switch 2912. As shown in FIG. 29B, the deuterium coil pairs 2904 and coil 2908 are positioned at a 90° angle. The orthogonal arrangement and 90° phase delayed feeding of the radio frequency ("RF") current reduces the power requirement for a well-defined flip angle to ½, compared to that needed for a single-saddle coil. In addition, the signal-to-noise ratio is increased by a factor of √2. A power transmitter 2920 at $^2$H frequency is connected at port #1 2912 of the hybrid via a band pass filter 2922 to a quadrature hybrid for power splitting and phase creating. Ports #2 2914 and #3 2916 of the hybrid are connected to the two $^2$H coils 2904 and 2908 using identical length cables. The combined signal is received at port #4 2918 of the hybrid that acts as a transmit/receive switch. The signal is passed to another band pass filter 2924 to the x-receiver port 2926.

Using dMRI in CSI mode and a single sagittal 8-mm slice covering the thoracic and abdominal cavities, a significant difference in in vivo liver deuterium signal in the cGVHD-affected mouse compared to control mice, syngeneic HSCT recipient and normal (unmanipulated) mouse, was detected. In one embodiment, the probe 700, such as the probe pictured in FIG. 7(D) provided greater sensitivity for deuterium detection, and allowed acquisition of chemical shift images (CSI) with improved spacial resolution and/or shorter imaging times. In this embodiment, the slice thickness was reduced to approximately 3 mm Higher levels of deuterium CSI were measured using dMRI in the livers of mice affected by cGVHD at day 28 as compared to control syngeneic HSCT livers at day 28 post transplant. Besides CSI deuterium imaging, the current probe shown in FIG. 7(D), allows for regular proton imaging. Anatomical images may be captured, onto which deuterium CSI signals can be overlaid. This enables the calculation of deuterium CSI signal coming specifically from liver and spleen and not from the surrounding tissues/spaces. The probe pictured in FIG. 7(D) is being used for cGVHD imaging of mice.

Figures 8A, 8B:
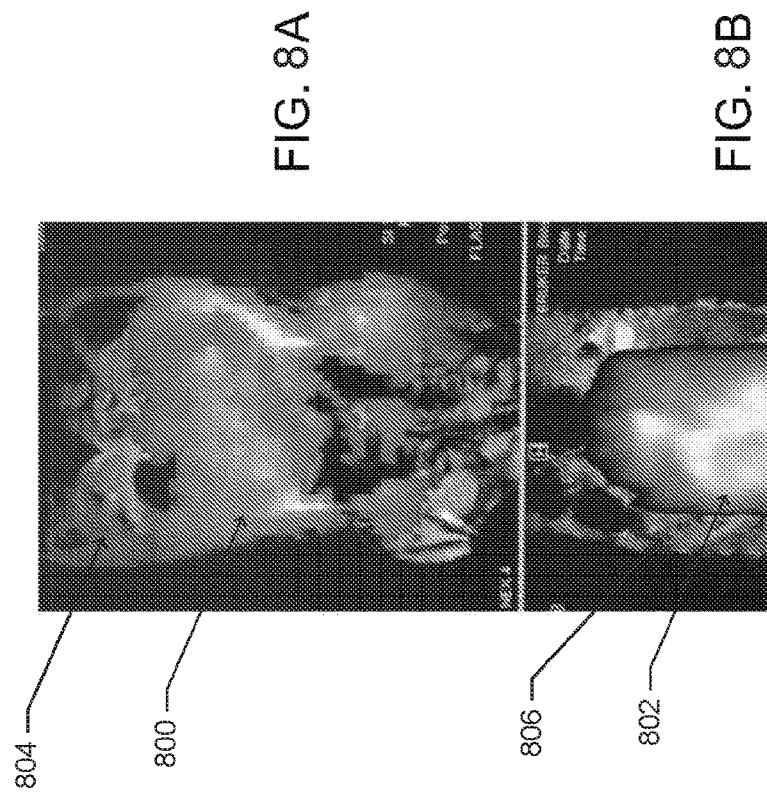
FIGS. 8A and B are deuterium MRI (dMRI) images overlaid on anatomical/proton MRI images, according to one embodiment.

FIGS. 8A-D illustrate example data obtained using a dMRI probe, such as those shown in FIGS. 7A-D and FIG. 15 to perform in vivo dMRI imaging of a syngeneic HSCT recipient and an allogeneic HSCT recipient (cGVHD-affected mouse), following deuterated water labeling for 21 days (day +7 to +28 post HSCT). FIGS. 8A and 8B shows dMRI images 800 and 802 overlaid on anatomical/proton MRI images 804 and 806. The images were obtained at day +28 from mice following syngeneic (A) and allogeneic (B) HSCT and deuterated water labeling to approximately 5% total body water for 21 days (i.e., day +7 to +28). It was observed at day +28, that the allogeneic HSCT recipient mice have clinical signs and symptoms of cGVHD. FIG. 8A is an image of a syngeneic HSCT recipient mouse, while FIG. 8B is an image of a cGVHD-affected mouse. Both mice were imaged with a 9.4 T Bruker magnet, similar to that shown in shown in FIG. 7(F). The images of FIGS. 8A and 8B were generated as 8-mm sagittal slices covering the lower thoracic and peritoneal cavities.

Figure 8C:
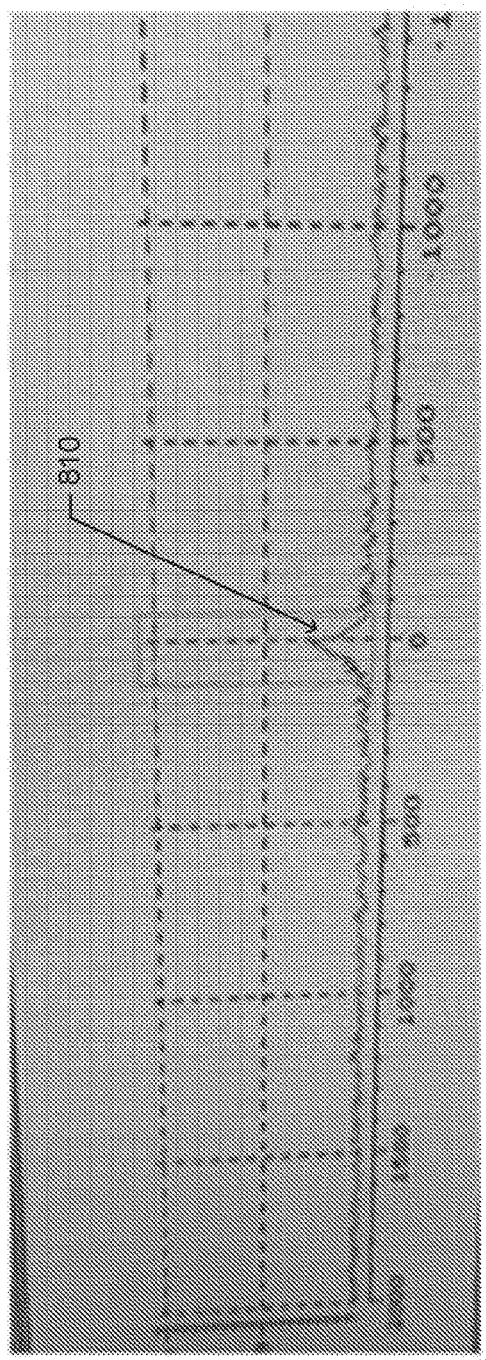
FIGS. 8C and D are images of the deuterium spectroscopy peaks that correspond to the regions of maximal signal intensity in the dMRI images in FIGS. 8A and 8B, respectively, according to one embodiment.
Figure 8D:
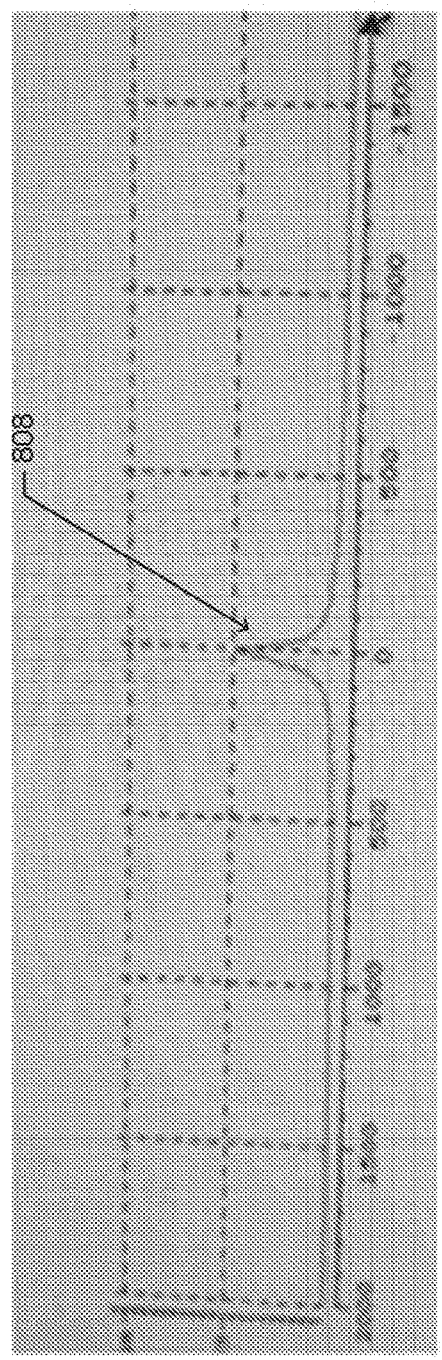

FIGS. 8C and 8D are images of the deuterium spectroscopy peaks that correspond to the regions of maximal signal intensity in the liver depicted on the dMRI images in FIGS. 8A and 8B, respectively. The deuterium peak 808 from the liver of allogeneic HSCT recipient mouse, as shown in FIG. 8D, is higher than the peak 810 of the syngeneic HSCT recipient mouse, as shown in FIG. 8C.

Figure 9:
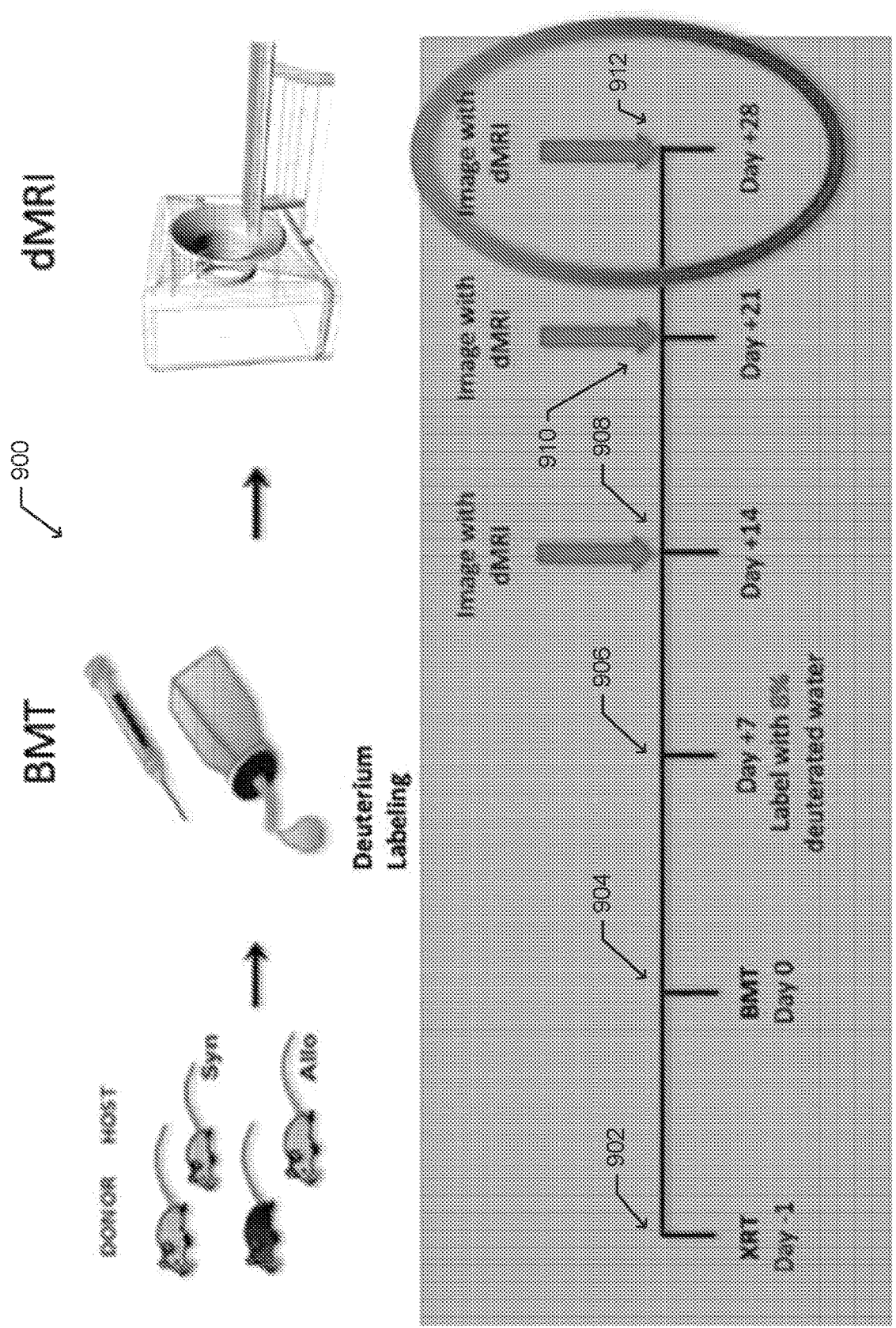
FIG. 9 is an illustration of an experimental schema for in vivo deuterated water labeling followed by dMRI imaging of rapidly dividing cells following HSCT, according to one embodiment.

FIG. 9 is an illustration for one embodiment of a scheme 900 for labeling and imaging rapidly dividing cells. As shown, the method begins with total body irradiation (TBI) conditioning performed one day prior to the infusion of a transplant graft (day −1), indicated as 902. In the embodiment shown, the bone marrow transplant (BMT) graft, containing bone marrow stem cells and T cells from the donor spleen, is infused on day 0, indicated as 904. One week after the transplant, indicated as 906, the subjects receive an intraperitoneal (IP) bolus of normal saline made in 100% $^2$H$_2$O, and thereafter receive drinking water containing 8% ($^2$H$_2$O) deuterated water. In one embodiment, the labeling schema resulted in approximately 5% TBW enrichment in the subjects.

Figure 14:
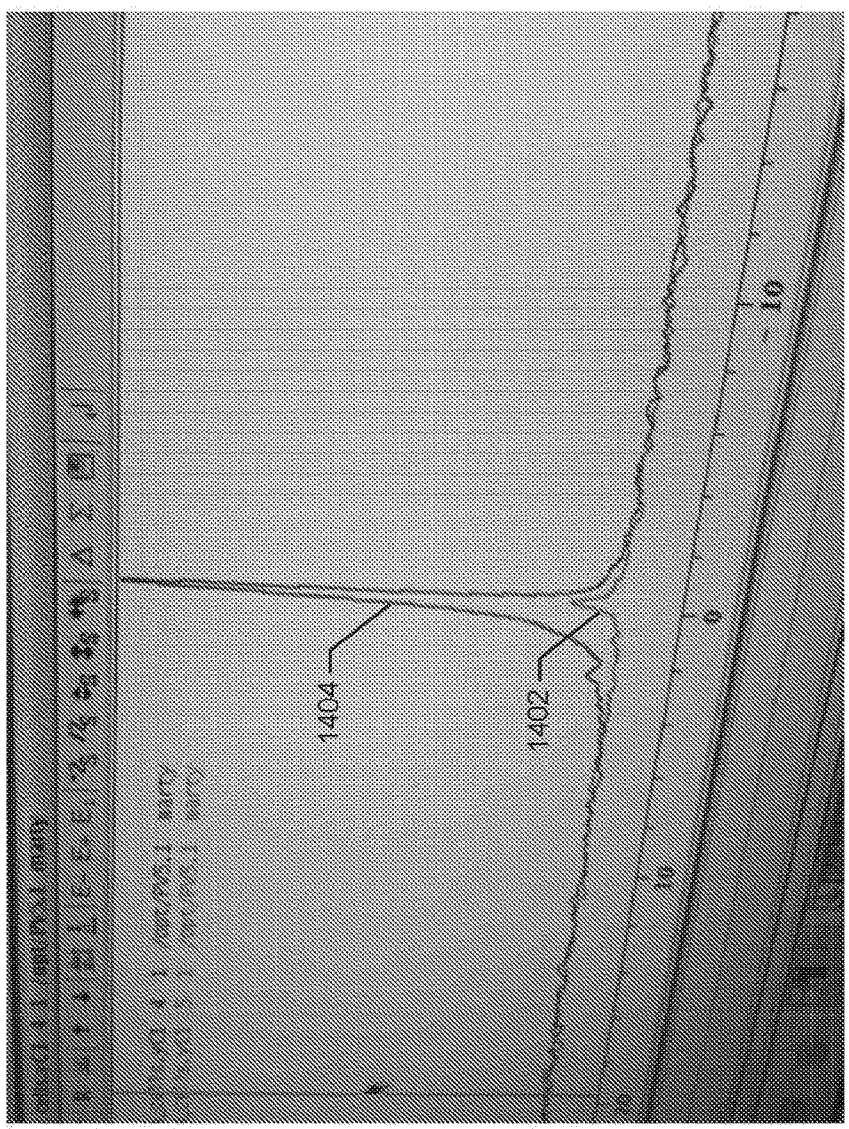
FIG. 14 is a photograph of a spectroscopic deuterium signal comparing signals from deuterium labeled mouse tumor cells and a phantom solution containing un-enriched water, according to one embodiment.

At various intervals after the labeling, chemical shift dMRI, $^{17}$O MRI, or swiMRI images of the subjects are captured. In one embodiment, the chemical shift dMRI images are gathered at weekly intervals, day +14, day +21, and day +28, as indicated by 908, 910, and 912 respectively. In various other embodiments, different intervals for imaging after labeling may be used. According to one aspect, a 5% $^2$H$_2$O phantom is also scanned simultaneously with the subject to provide reference data. The phantom may be included in one or more scans 908-912. FIG. 14 is a photograph of a spectroscopic deuterium signal 1402 from cultured mouse tumor cells having a dA deuterium enrichment of ~50%, and a signal 1404 from a phantom solution containing un-enriched water (0.015% $^2$H$_2$O in H$_2$O (v/v)).

In various embodiments, the slice thickness of the captured dMRI images may be varied. In one preferred aspect, thinner slices (e.g. less than or equal to 3-mm are captured to improve image resolution), as illustrated in FIGS. 10-11, but a summation of data from several slices may be necessary to better estimate total organ deuterium and/or $^{17}$O CSI signal.

Figure 10:
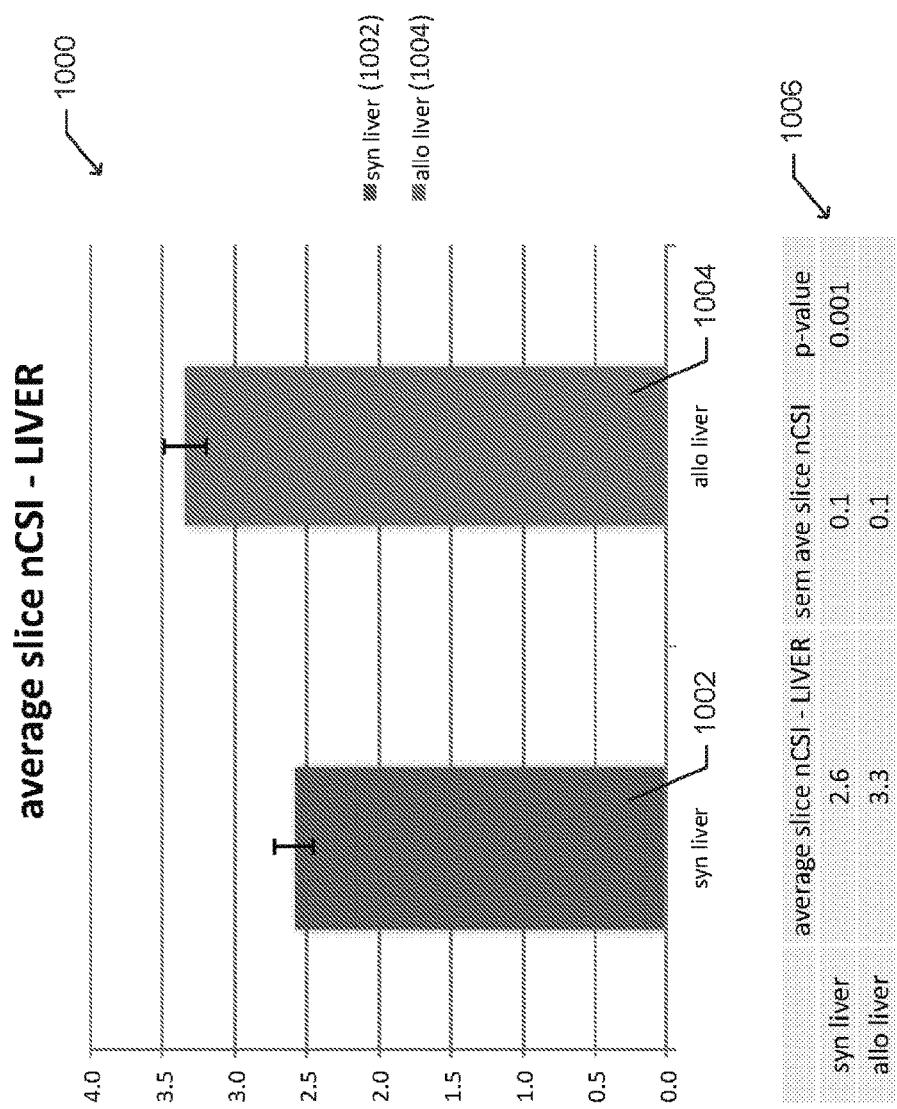
FIG. 10 is a bar graph depicting averages of normalized deuterium chemical shift imaging (CSI) signals detected in the liver of multiple mice following syngeneic and allogeneic HSCT according to one embodiment.

FIG. 10 is a bar graph 1000 presenting averages of normalized deuterium chemical shift imaging (CSI) signals detected in liver (target organ of cGVHD) of multiple mice following syngeneic 1002 and allogeneic 1004 HSCT, with error bars representing standard error, and p-values 1006. Three syngeneic and four allogeneic HSCT recipients were imaged and three 3-mm slices were obtained per animal. The liver deuterium CSI signals for each mouse were normalized to a deuterium CSI signal detected from a phantom of 5% $^2$H$_2$O in H$_2$O (v/v), that was imaged concurrently with each animal. All signals were measured on day +28 following HSCT and after 21 days of deuterated water labeling (day +7 to +28) to 5% total body water.

Figure 11:
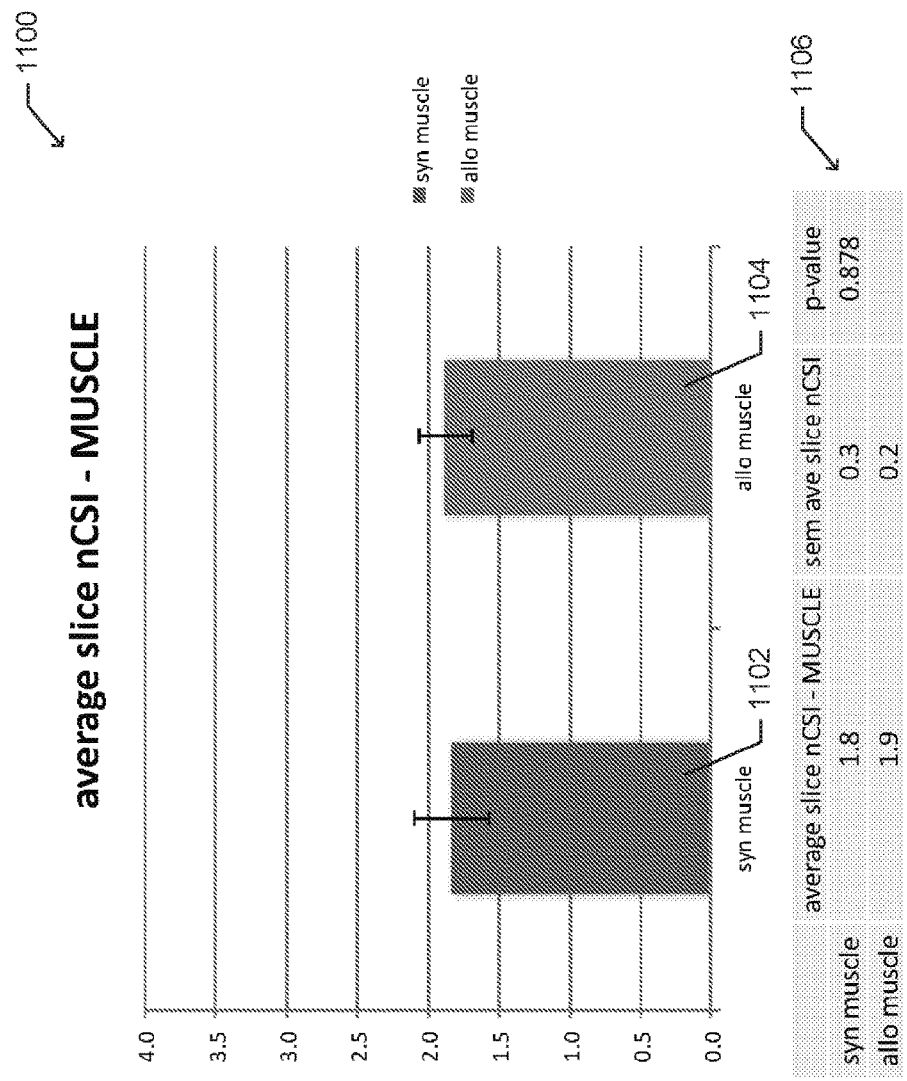
FIG. 11 is a bar graph depicting averages of normalized deuterium chemical shift imaging (CSI) signals detected in quadriceps muscle tissue, of multiple mice following syngeneic and allogeneic HSCT, according to one embodiment.

FIG. 11 is bar graph 1100 presenting averages of normalized deuterium chemical shift imaging (CSI) signals detected in quadriceps muscle tissue, which is not affected by cGVHD. The signals were gathered from multiple mice following syngeneic 1102 and allogeneic 1104 HSCT, with error bars representing standard error, and p-values 1106. Three syngeneic and four allogeneic HSCT recipients were imaged and three 3-mm slices were obtained per animal. The muscle deuterium CSI signals for each mouse were normalized to a deuterium CSI signal detected from a phantom of 5% $^2$H$_2$O in H$_2$O (v/v), that was imaged concurrently with each animal. The signals were measured on day +28 following HSCT and after 21 days of deuterated water labeling (day +7 to +28) to 5% total body water.

After capturing data using any of the embodiments for labeling and imaging disclosed, a cGVHD-affected liver was readily distinguishable from a syngeneic control liver, in vivo, after an average of 21 days of continuous labeling to maintain deuterium enrichment of 5% in TBW. In various aspects, a distinction between a cGVHD-afflicted affected liver and a syngeneic control liver may be observed in as little as 14 days.

Figure 12:
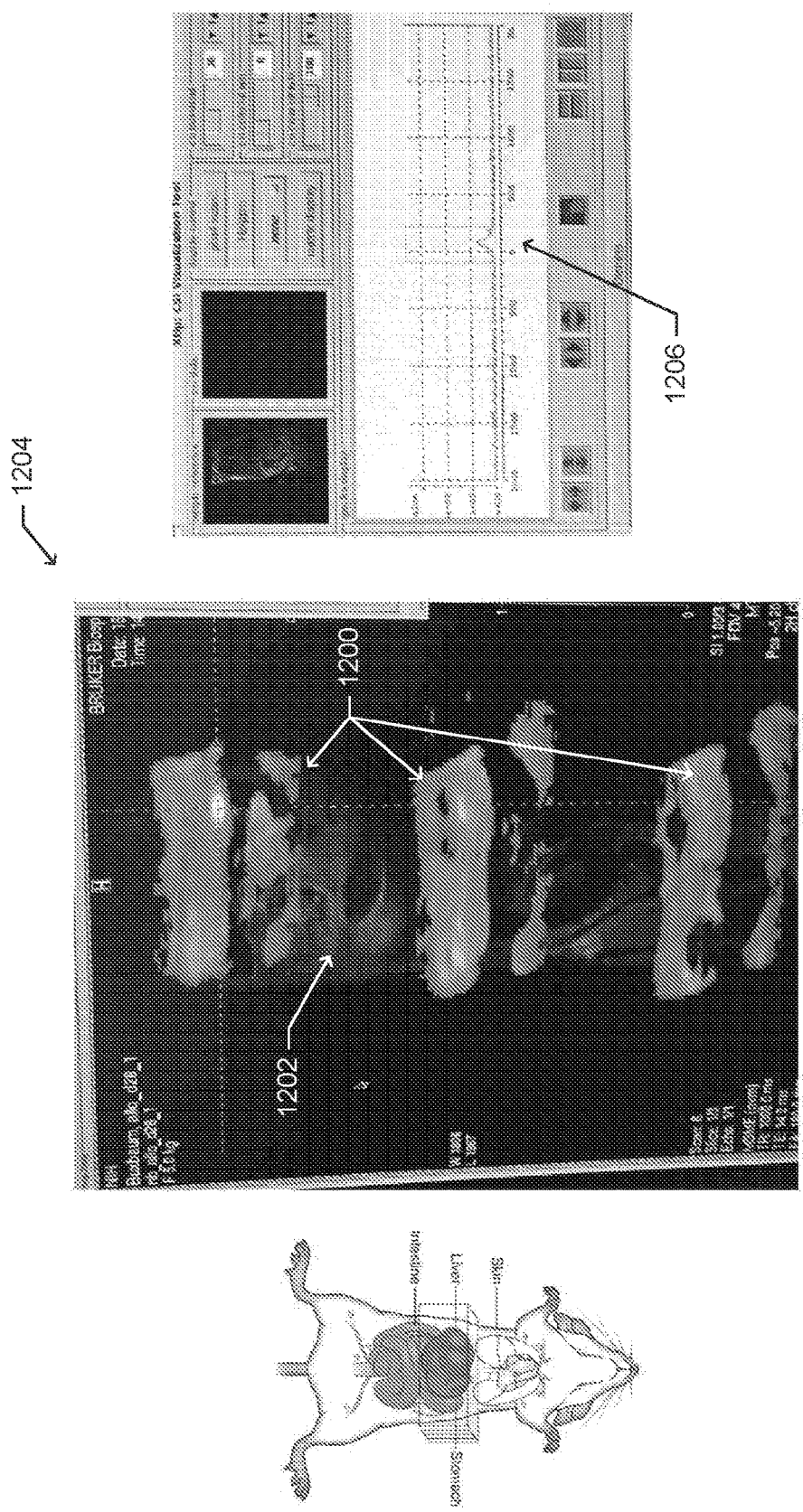
FIG. 12 depicts an MRI scan and a spectroscopic deuterium peak for a single mouse with the deuterium CSI signal overlaid on an anatomical/proton MRI, according to one embodiment.

For example, FIG. 12 shows captured deuterium chemical shift ionization (CSI) data 1200 overlaid on an anatomical/proton MRI image 1202. The MRI scan 1204, which includes the CSI data 1200 and the anatomical image 1202, is shown with a spectroscopic deuterium peak 1206. The data were gathered on day +28 post allogeneic HSCT, for a single mouse. The deuterium CSI signal and anatomical/proton MRI image were obtained simultaneously on a Bruker 9.4 T magnet, such as that shown in FIG. 7(E), using a multi-tuned probe, such as that shown in FIG. 7(D). The mouse was labeled according to the methods disclosed with deuterated water to approximately 5% $^2$H$_2$O in total body water for 21 days (day +7 to +28). Three approximately 3-mm thick coronal slices through the mid-abdomen were captured. The liver and spleen were identified through anatomical imaging, and the deuterium CSI signals for each slice through the liver and spleen are shown.

In various aspects, the supplementation of deuterium and other stable water isotopes can range from days to months, to maintain the desired TBW enrichment. Once deuterium supplementation is discontinued, TBW deuterium enrichment will return to baseline (0.015%) in approximately 7 to 14 days in mice and people, respectively.

In Vivo Imaging with $^{17}$O

In various embodiments, systems and methods to visualize rapidly dividing cells in vivo may use $^{17}$O as a non-radioactive label. $^{17}$O is a stable isotope having gyromagnetic properties amenable to MRI. As a gas, $^{17}$O has been used clinically to label autologous red blood cells (RBCs) for vascular MRI imaging. In this aspect, red blood cells may be extracted from a patient and passed through a chamber of gaseous $^{17}$O. $^{17}$O is loaded onto hemoglobin molecules inside RBCs, which then are returned to the patient's circulation and function as a contrast agent allowing visualization of blood vessels. Alternatively, concentrations of gaseous $^{17}$O may be used to measure oxygen metabolism to detect ischemia.

Various embodiments of the systems and methods disclosed may use $^{17}$O in a liquid form as isotopic water having the formula H$_2$$^{17}$O. Similar to deuterium contained in $^2$H$_2$O, the $^{17}$O isotopic water would be injected and/or ingested and would incorporate into the DNA of rapidly dividing cells as a labeling agent. The de-labeling kinetics of $^{17}$O are substantially similar to those of deuterium enrichment as previously described.

Stable isotopic water containing deuterium and $^{17}$O (i.e. $^2$H$_2$$^{17}$O) may be used to "double" label rapidly dividing cells and enhance swiMRI signal for the early detection and monitoring of cGVHD, and other conditions characterized by rapidly dividing cells. In embodiments using H$_2$$^{17}$O or $^2$H$_2$$^{17}$O, one or more swiMRI probes similar to those shown in FIG. 7 may be used. Similarly, the MRI probes would be multi-tuned to capture signals from protons for anatomical imaging, and deuterium ($^2$H), and isotopic oxygen (s.a. $^{17}$O) for spectroscopic imaging, simultaneously.

Besides using stable isotopes of hydrogen and/or oxygen in water as labels for detecting cGVHD, $^2$H and $^{17}$O may also be used for non-invasive and non-radioactive in vivo imaging of tumors as an alternative to positron emission tomography (PET). As shown in FIG. 14, a clear spectroscopic deuterium signal is obtained from mouse tumor cells labeled in vitro with deuterated water during culture.

Besides in vivo labeling followed by imaging, various other embodiments of the systems and methods disclosed may be used for ex vivo labeling followed by in vivo or in vitro dMRI imaging. By way of example and not limitation, immunotherapy products may be labeled ex vivo during production. Subsequent deuterium ($^2$H), and isotopic oxygen (s.a. $^{17}$O) swiMRI can visualize the in vivo localization of the infused cells.

Total body water (TBW) enrichment with stable water isotopes of hydrogen and/or oxygen ($^2$H$_2$O, H$_2$$^{17}$O, or $^2$H$_2$$^{17}$O) can be measured in small volumes of body fluid, such as saliva, urine or blood. A novel method for testing TBW is described in a draft manuscript by Farthing, D F, et al. "Uncharted Waters—Comparing stable isotopic forms of heavy water incorporation into DNA of proliferating cells," which is found in U.S. Provisional Application No. 62/414,554, filed Oct. 28, 2016 and which is incorporated herein by reference in its entirety. Such measurements may be useful to monitor animal and human subject compliance with label intake, some of which may occur in the outpatient setting (unmonitored). Total body water (background) stable water isotope enrichment has and would be measured prior to swiMRI scan and/or various intervals before, during, and after the labeling period. Measurement of TBW enrichment with stable water isotopes is important because higher than 0.015% deuterium concentration and 0.04% $^{17}$O concentration found in regular water are necessary to generate high enrichment of label into rapidly dividing cells facilitating subsequent detection with swiMRI.

An Analysis of T-Cell Kinetics and a Working Example of T-Cell Labeling and Deuterium MRI Imaging of cGVHD T cells are central to the biology of chronic graft-versus-host disease (cGVHD), a morbid and prevalent allo-immune complication of hematopoietic stem cell transplantation (HSCT). Using in vivo deuterated water labeling in a mouse model of GVHD, we measured kinetics of CD4+ T cell subsets, i.e. T regulatory ($T_{Reg}$), T effector memory ($T_{EM}$), and T naïve ($T_N$), in lymphoid and target organs. We found that a low (<<1) $T_{Reg}$ to CD4+ $T_{EM}$ ratio rather than $T_{Reg}$ to $T_{CON}$, both in circulation and systemically, is predictive of impending GVHD and established disease. Despite high proliferation in lymphoid and target organs, the systemic $T_{Reg}$ number is low due to reduced $T_{Reg}$ survival in target organs. These findings, in part, underlie the limited efficacy of treatment regimens for GVHD that inhibit general T cell proliferation, without targeting particular subsets. By identifying contrasting distribution of CD4+ T cell subsets in a target organ (e.g. liver) of diseased animals with their differential deuterium DNA enrichment, we developed a novel deuterium magnetic resonance imaging (dMRI) approach to discern GVHD-affected animals from the control HSCT recipients. We show that deuterated water labeling as used for kinetics studies followed by dMRI can facilitate a non-invasive and non-radioactive in vivo diagnosis of GVHD.

While T cells are at the biological forefront of diseases across disciplines, such as autoimmunity, infectious disease, inherited and acquired immunodeficiency, malignancy, and transplantation, their in vivo behavior, encompassing generation of new cells, cell survival, and trafficking, is difficult to measure and interpret. Further complexity arises from T cells comprising of subsets, which differ not only by phenotype, but also by function. Allogeneic hematopoietic stem cell transplantation (AHSCT) is a treatment strategy widely used to cure malignant and non-malignant diseases. Chronic GVHD (cGVHD) is a morbid, prevalent, and refractory AHSCT barrier, characterized by systemic immune dysregulation driven by allo-reactive donor T cells. T regulatory ($T_{Reg}$) cells play a critical role in cGVHD, with several animal and clinical studies demonstrating the potential of $T_{Reg}$ cells to treat this disease. The origin of the imbalance between regulatory and allo-reactive T cells in cGVHD should be explored further, and understanding of in vivo T cell subset kinetics should illuminate the biology that underlies the imbalance.

Deuterium labeling (via water or glucose) for measuring in vivo cell kinetics has been extensively used for over a decade. It provides an alternative to other nucleoside analogs, such as bromodeoxyuridine (BrdU) and tritiated thymidine ($^3$HTdR) that are typically not applicable to clinical studies due to toxicity, and incorporate into the DNA of dividing cells via the salvage pathway of nucleotide synthesis, which is unpredictable and varies by cell type. Indeed, T cell subsets differ in their dependence on this pathway based on their stage of maturation (i.e. naïve versus memory). In contrast, deuterium is incorporated into cellular DNA through the constitutive de novo nucleotide synthesis pathway, which is not subject to regulation. Since stable isotopes are not radioactive, deuterium labeling lends itself to clinical translation with relatively small amounts of deuterium enrichment (~5%) in total body water required for kinetics measurements. Pioneering in vivo kinetics studies were conducted in patients with HIV, which measured T cells (CD4+ and CD8+), then many other cell types and conditions. To date, studies involving stable isotopes measured T cell kinetics in circulation, a dynamic cellular compartment, while systemic cell half-lives were mathematically estimated. The logistical complication of extracting cells from organs and tissues in patients precluded measurement of systemic cellular dynamics, but egress from circulation and migration into tissue is key to T cell function. These limitations are abrogated in small animal studies since cells of interest can be extracted from a number of organs. However, to our knowledge, no previous studies have employed deuterium labeling to measure kinetics of T cells or other cell types in multiple compartments. We show that the same CD4+ T cell subset (i.e. $T_{Reg}$) can have vastly different kinetics in lymphoid versus target organs. It is desirable to evaluate biologically distinct subsets of T cells (not simply CD4+ versus CD8+ T cells), because we found that CD4+ naïve, memory, and regulatory cells have differential in vivo kinetics.

GVHD has been defined by an imbalance between immunoregulatory and pathogenic CD4+ T cells. While our work confirms these findings, we provide further insight and detailed understanding of the immune imbalance by defining it as a low $T_{Reg}$ to CD4+ $T_{EM}$ ratio (<<1), and provide measurements of T cell subset behaviors that underlie the low ratio. The $T_{Reg}$ to T conventional ($T_{CON}$) or $T_{Reg}$ to CD4+ $T_{CON}$ ratios prominently figure in discussions of post-HSCT immunity and $T_{Reg}$ studies, but, in our model, may not distinguish cGVHD-affected from unaffected cohorts, in circulation, lymphoid or target organs. These ratios are not currently used to predict ongoing or impending cGVHD in patients. In contrast, the ratio we focus on, $T_{Reg}$ to CD4+ $T_{EM}$, not only defines which animals are affected by cGVHD, but also predicts cGVHD in advance of disease manifestations. The $T_{Reg}$ to CD4+ $T_{EM}$ ratio may be altered in patients with GVHD, and should be explored further. Finally, our novel use of deuterium labeling to facilitate non-invasive and non-radioactive magnetic resonance imaging (MRI) of cGVHD may introduce an objective criterion for cGVHD diagnosis, which is currently challenging and primarily subjective.

Results

CD4+ T cell immune reconstitution in cGVHD is skewed toward distribution to target rather than lymphoid organs, with a predominance of the $T_{EM}$ phenotype. As previously described, allogeneic graft recipients consistently developed cGVHD by post-transplant day 28; while at day +14 clinical scores were not consistent with cGVHD. (FIG. 16).

Figure 17A:
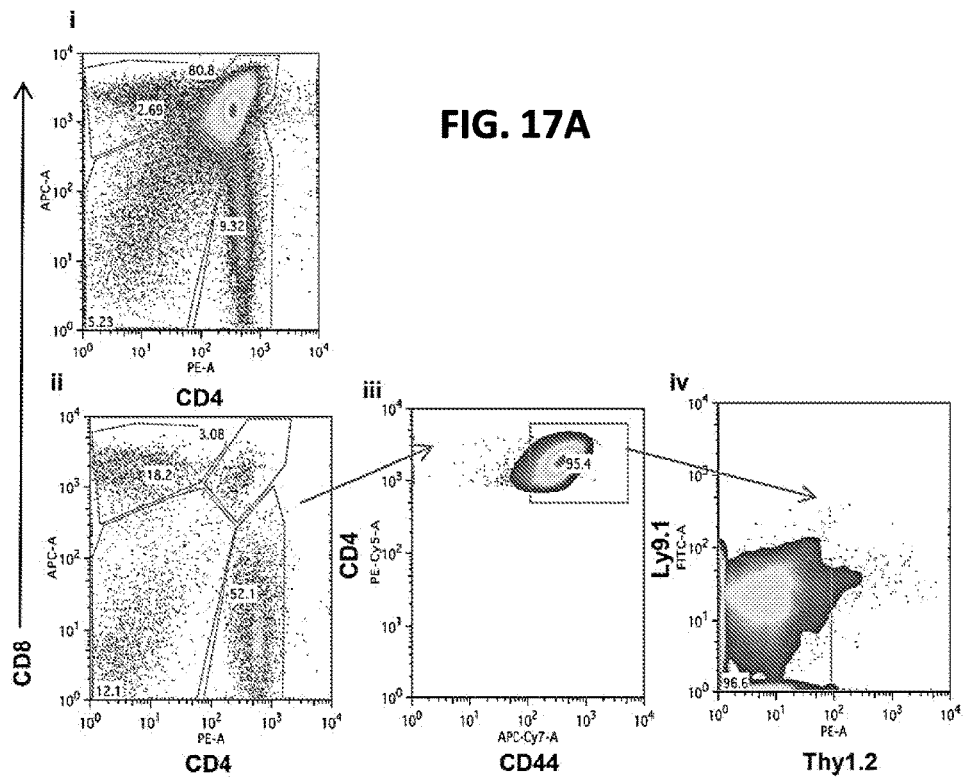
FIGS. 17A-17B include flow cytometry data illustrating lymphoid immune reconstitution (thymus and spleen) in allogeneic recipients according to one embodiment.
Figure 17B:
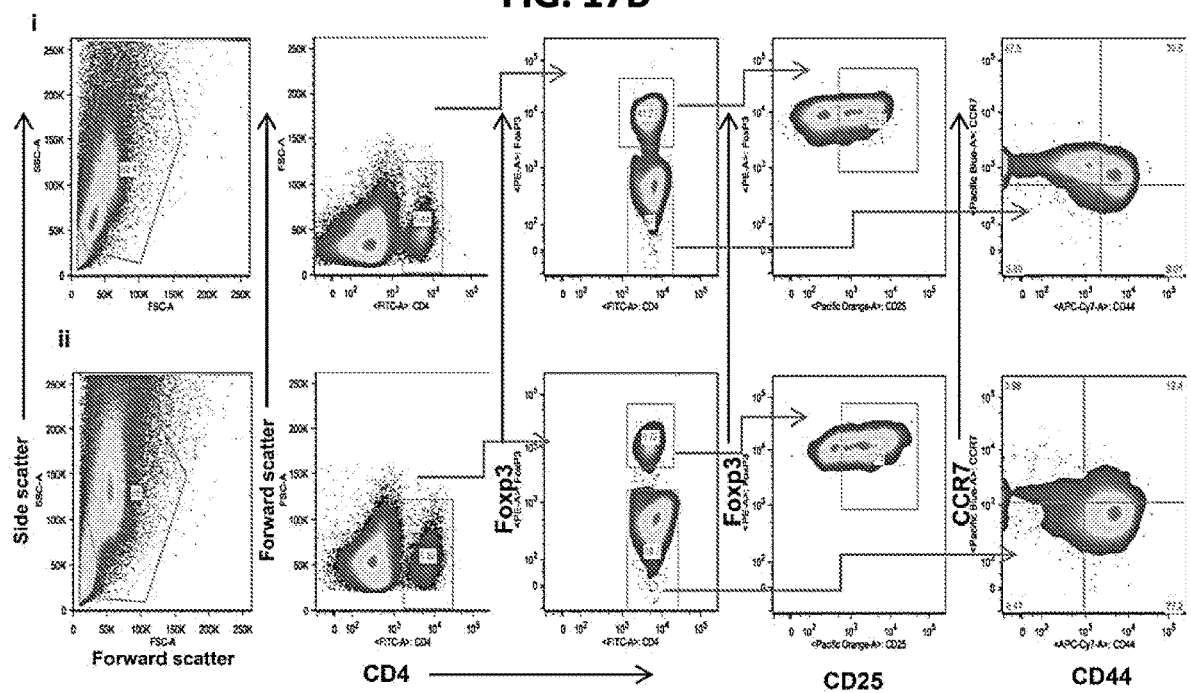

Lymphoid atrophy and low absolute CD4+ T cell numbers in the thymi and lymph nodes were observed in allogeneic recipients at day +14 and persisted through day +28. In addition, thymi of allogeneic recipients contained a mature (CD44 high) CD4+ T cell infiltrate with a marked reduction in T cell precursors (FIG. 17A). At day +14, splenomegaly was seen in allogeneic recipients. It was characterized by mild extra medullary hematopoiesis and a high number of CD4+T cells, primarily of the $T_{EM}$ (CD4+ FoxP3- CD44 high CCR7-) phenotype (FIGS. 18A-E). Following initial size increase, the spleen underwent atrophy with a near absence of CD4+ T cells in the spleen at day+28 (FIGS. 18A-D). In congenic allogeneic HSCT experiments, CD4+ T cells harvested from the host thymus and spleen at various times following transplantation, day +7 through +35, were of a donor-derived peripherally expanded mature phenotype (Thy1.1 Ly 9.2 CD44 high) (FIG. 17B).

Figure 16:
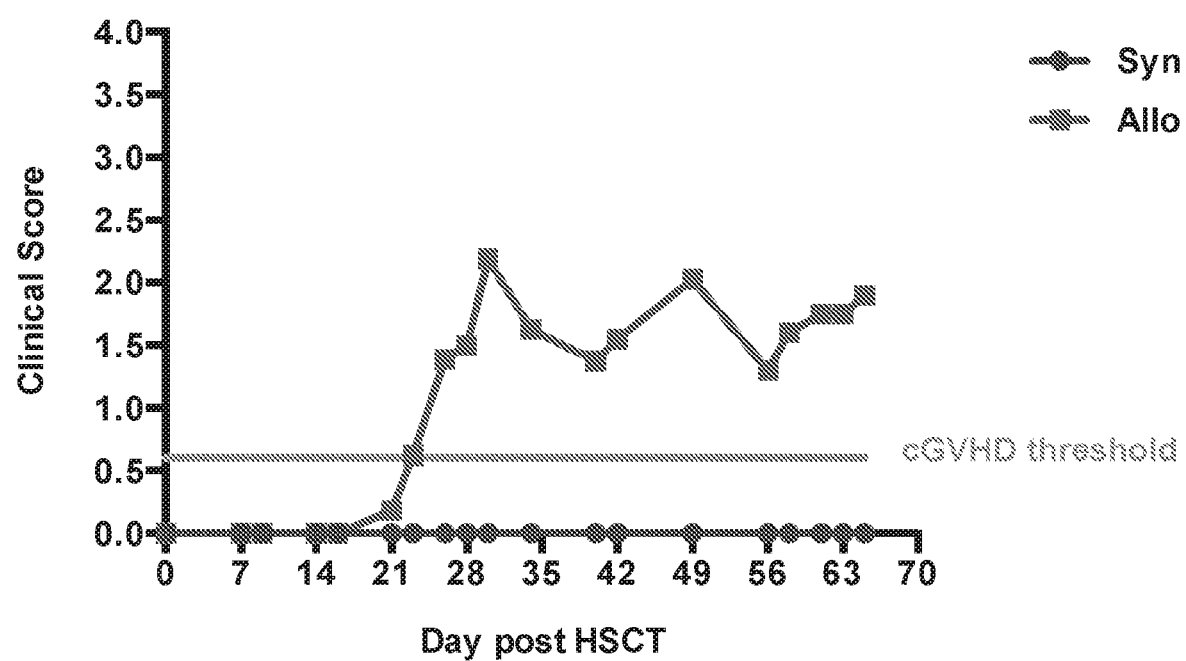
FIG. 16 is another depiction of the graph of 2A depicting clinical scores relating to cGVHD symptoms for syngeneic HSCT recipients and allogeneic HSCT recipients, according to one embodiment.

The following caption applies to FIG. 16: "Clinical scoring data for mice undergoing HSCT." (a) Typical clinical score curve for mice in syngeneic and allogeneic cohorts at specified post HSCT time points. The Green threshold line represents a clinical score of 0.6, minimum score for considering mice as having clinical evidence of cGVHD. Data for day 0 through +35 are representative of more than ten independent experiments.

The following caption applies to FIG. 17: "Lymphoid immune reconstitution in allogeneic recipients is characterized by donor peripherally-expanded mature CD4+ T cell predominance" (a) Thymic immune-reconstitution following HSCT evaluated by flow cytometry at day +30. (i) Syngeneic recipients show a predominance of double positive thymocytes (CD4$^+$CD8$^+$). (ii) Allogeneic recipients show a predominance of single positive CD4$^+$, and near absence of double positive and double negative thymocytes (CD4$^-$CD8$^-$). (iii) These single positive CD4$^+$ cells are primarily of memory (CD44$^+$) phenotype. (iv) Congenic markers showed that CD4$^+$CD44$^+$ cells were of donor-derived peripherally expanded phenotype (Ly9.1$^-$Thy1.2$^-$). Data are representative of three independent experiments (i, ii) and two independent experiments (iii, iv). (b) Flow cytometry gating strategy for spleen samples, with (i) syngeneic and (ii) allogeneic cohort representative data for day +14.

Figure 18:
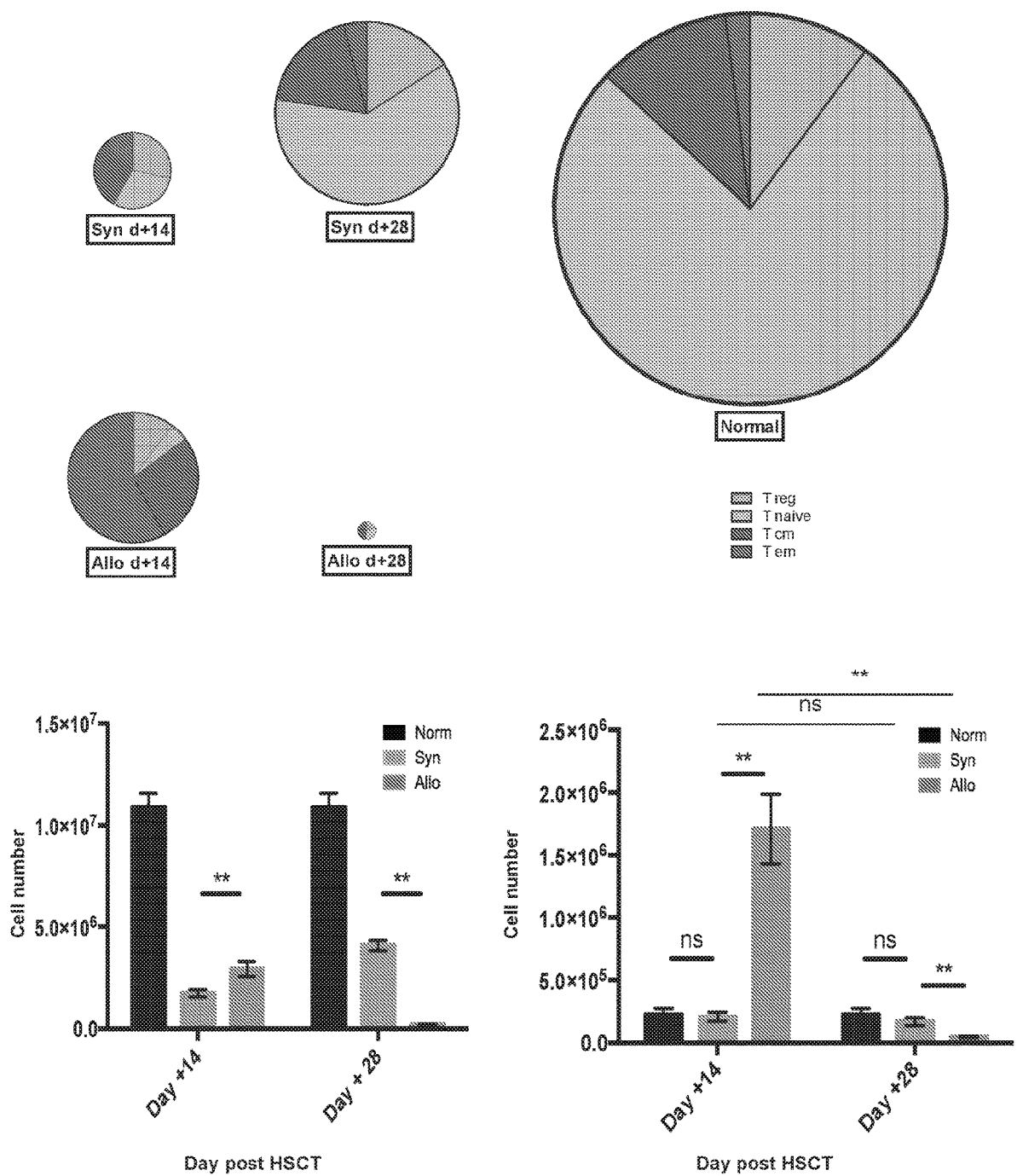
FIG. 18 includes charts and graphs presenting spleen CD4+ T cell numbers and compositions for normal mice, syngeneic, and allogeneic HSCT recipients, according to one embodiment.

The following caption applies to FIG. 18: "Spleen CD4+ T cell number and composition for normal mice, syngeneic, and allogeneic HSCT recipients." (a and b) The mean total CD4$^+$ T cell number for syngeneic day +14=1.7×10$^6$, syngeneic day +28=4.1×10$^6$, allogeneic day +14=2.9×10$^6$, allogeneic day +28=0.2×10$^6$, normal=10.9×10$^6$. The size of each pie was normalized to one. Data shown in (b) represent the mean, with SEM error bars. (c) The mean spleen $T_{EM}$ cell number in allogeneic versus syngeneic recipients measured at day +14 and +28, with SEM error bars. Data for four independent experiments were pooled for these analyses (n=2 to 7 mice per cohort per time point) and are representative of more than ten independent experiments. **, P<0.01."

Figure 21A:
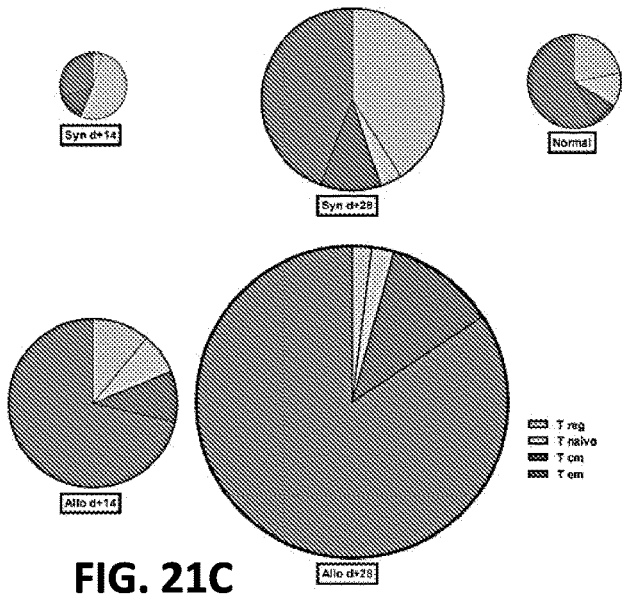
FIGS. 21A-21D include charts and graphs presenting dermal T cell numbers and compositions for normal mice, syngeneic, and allogeneic HSCT recipients, according to one embodiment.
Figure 21B:
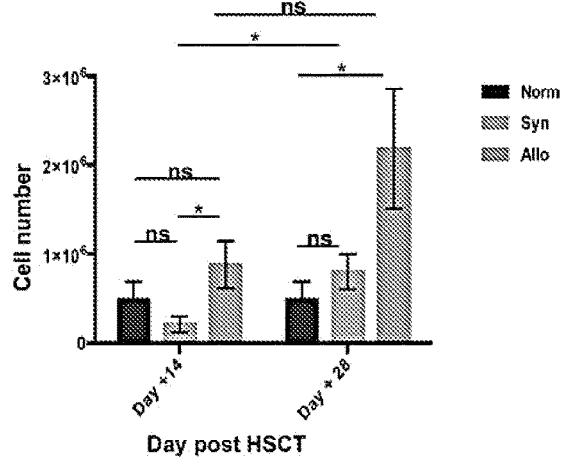
Figure 21C:
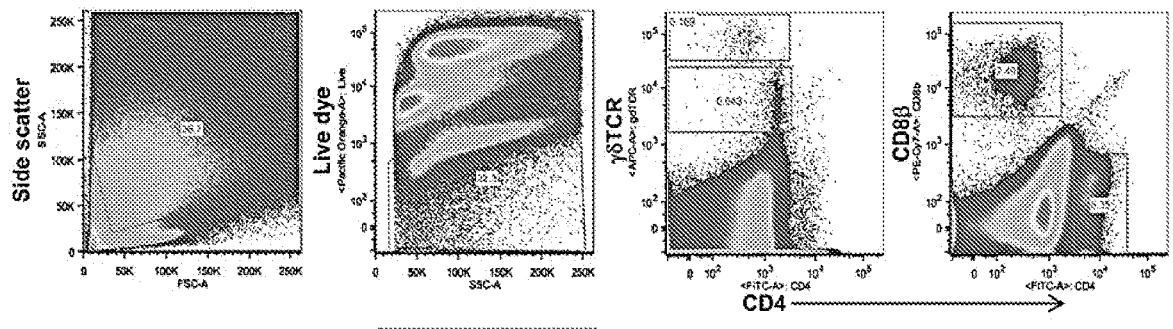
Figure 21D:
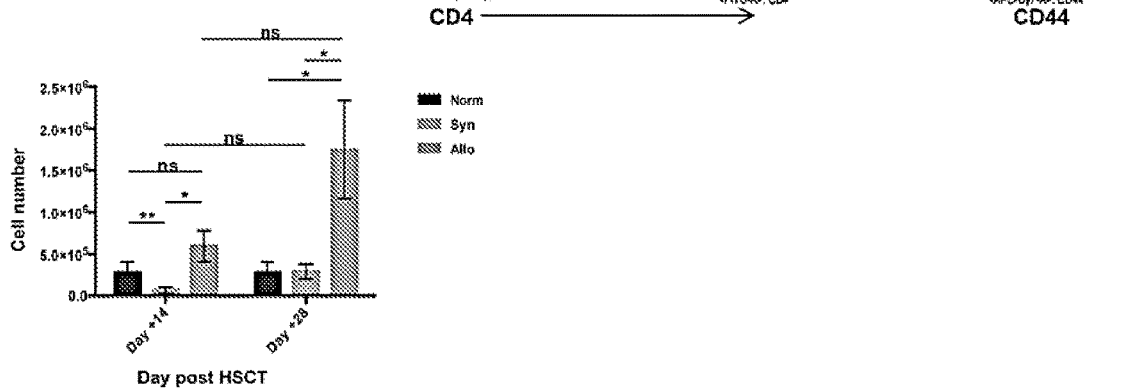
Figure 22A:
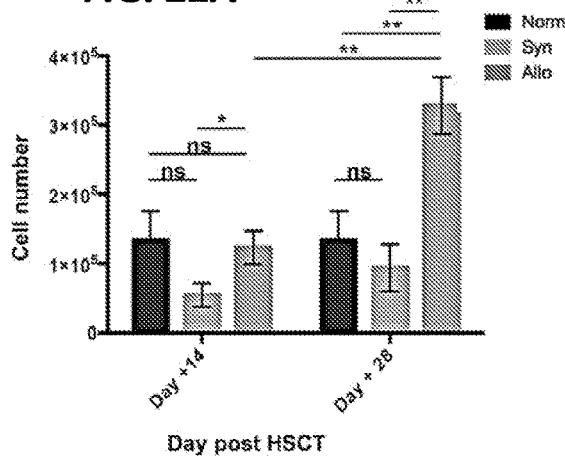
FIGS. 22A-22E include charts and graphs presenting small intestine lamina propria (LP) and intraepithelial (IE) CD4+ T cell numbers and compositions for normal mice, syngeneic, and allogeneic HSCT recipients, according to one embodiment.
Figure 22B:
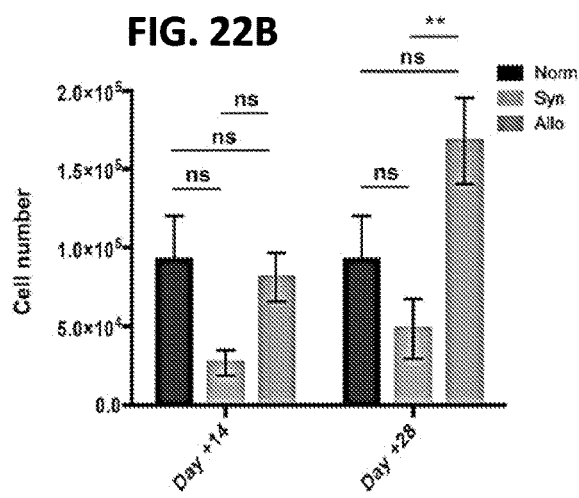
Figure 22C:
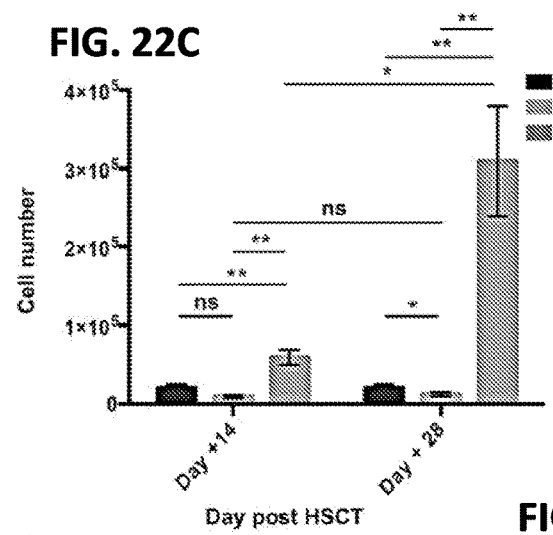
Figure 22D:
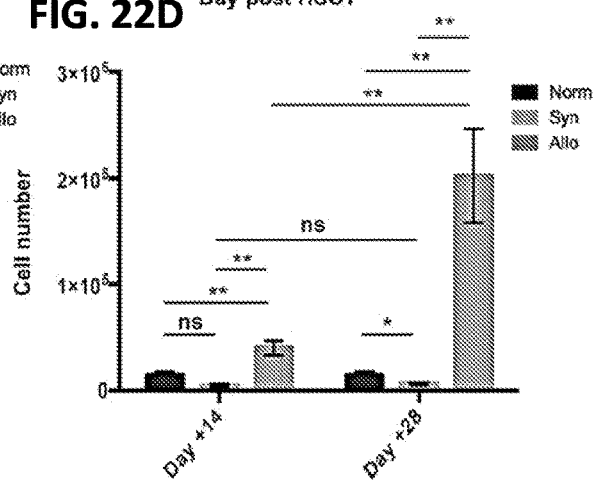
Figure 22E:
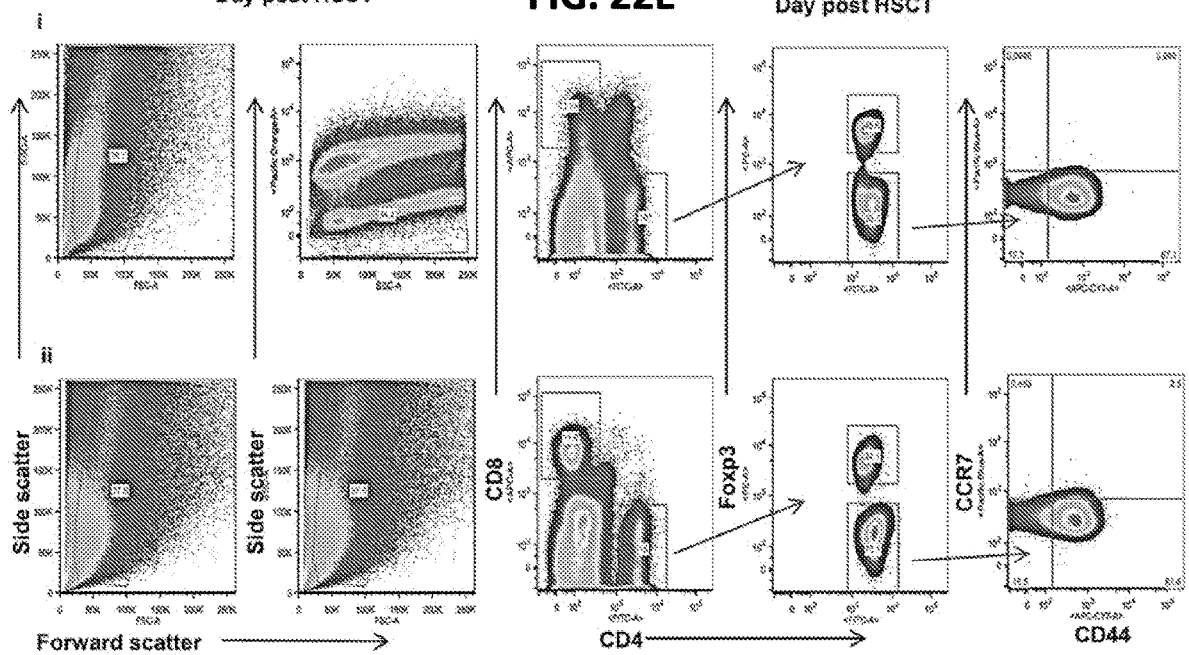

The target organs affected by cGVHD, i.e. integument, liver, and small intestine were characterized by lymphocytic infiltrates (FIGS. 19A-J). Liver parenchyma of allogeneic recipients contained approximately a log higher absolute number of CD4+ T cells by day +14 compared to the syngeneic counterparts (FIGS. 20A-C). Similar to other target organs affected by cGVHD, the predominant CD4+ T cell subset was $T_{EM}$, and a decreased $T_{Reg}$ (CD4+FoxP3+ CD25+): $T_{EM}$ ratio was observed (FIG. 20A, C) Dermal parenchyma sections of the allogeneic cohort had higher CD4+ absolute counts than syngeneic counterparts (FIGS. 21A-B). Furthermore, $T_{EM}$ phenotype predominated in the dermal CD4+ T cell pool in the allogeneic setting both at day +14 and day +28 (FIG. 21D). In the small intestine, CD4+ T cell number was increased in the lamina propria (LP) and intraepithelial (IE) compartment of allogeneic compared to syngeneic recipients (FIGS. 22A, C). Furthermore, the $T_{EM}$ proportion and total number were significantly higher in allogeneic LP than syngeneic and normal LP by day +28, and in the IE compartment at both time points (FIGS. 22B, D).

Figure 19:
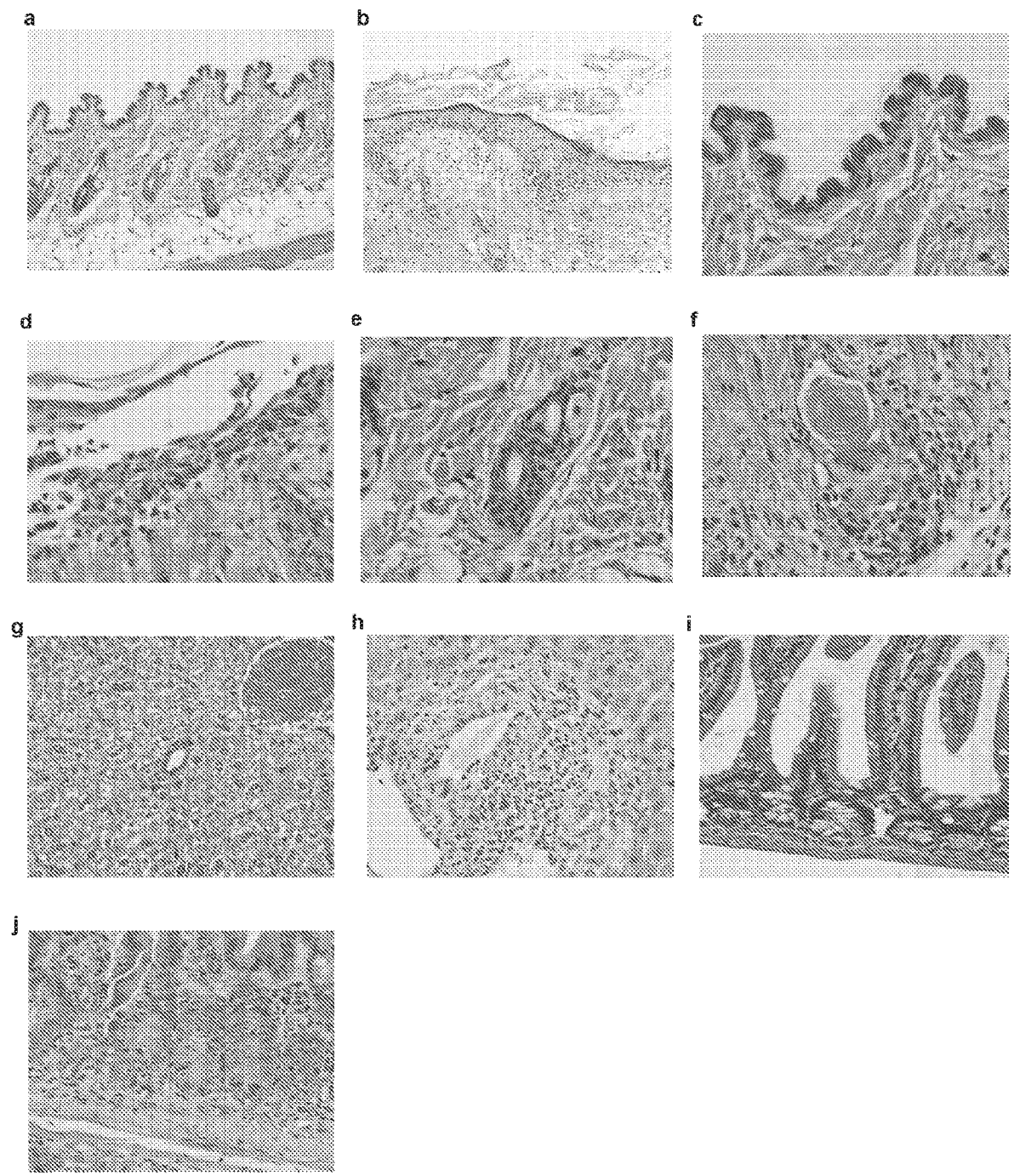
FIGS. 19A-19J depict histology slides of target organs for syngeneic and allogeneic recipients, according to one embodiment.

The following caption applies to FIG. 19: "Mouse target organ histology and flow cytometry characteristics for syngeneic and allogeneic HSCT recipients." Target organ histology for syngeneic and allogeneic recipients. (a) Representative syngeneic HSCT recipient skin section, 200×; normal skin histology is observed at day +14 and day +28. (b) Allogeneic HSCT recipient skin section, 200×, day +28. Prominent hyperkeratosis and acanthosis are observed. While the magnification and orientation of the section are similar for (a) and (b), in (b) hyperkeratosis precludes visualization of additional skin layers (subcutis and muscularis not visualized). (c) Syngeneic skin epithelial section, 600×; normal histological appearance. (d) Allogeneic skin epithelial section, 600×, day +28; intraepithelial lymphocytes evident with dyskeratotic epithelial cells. (e) Syngeneic skin hair follicle section, 600×; normal histological appearance. (f) Allogeneic skin hair follicle section, 600×, day +28; intraepithelial peri-follicular lymphocytes and dyskeratotic epithelial cells are evident. (g) Syngeneic liver section, 400×, day +14; normal histologic appearance. (h) Allogeneic liver section, 400×, day +14; moderate lymphocytic periductal infiltrate is present. (i) Syngeneic small intestine section, 400×, day +14; normal intestinal crypt and villi histology is observed. (j) Allogeneic section, 400×, day +14; crypt hyperplasia, increased number of epithelial cells, and a lymphocytic infiltrate are observed. Histology findings are representative of two independent experiments (n=5 mice per cohort per time point).

Figure 20:
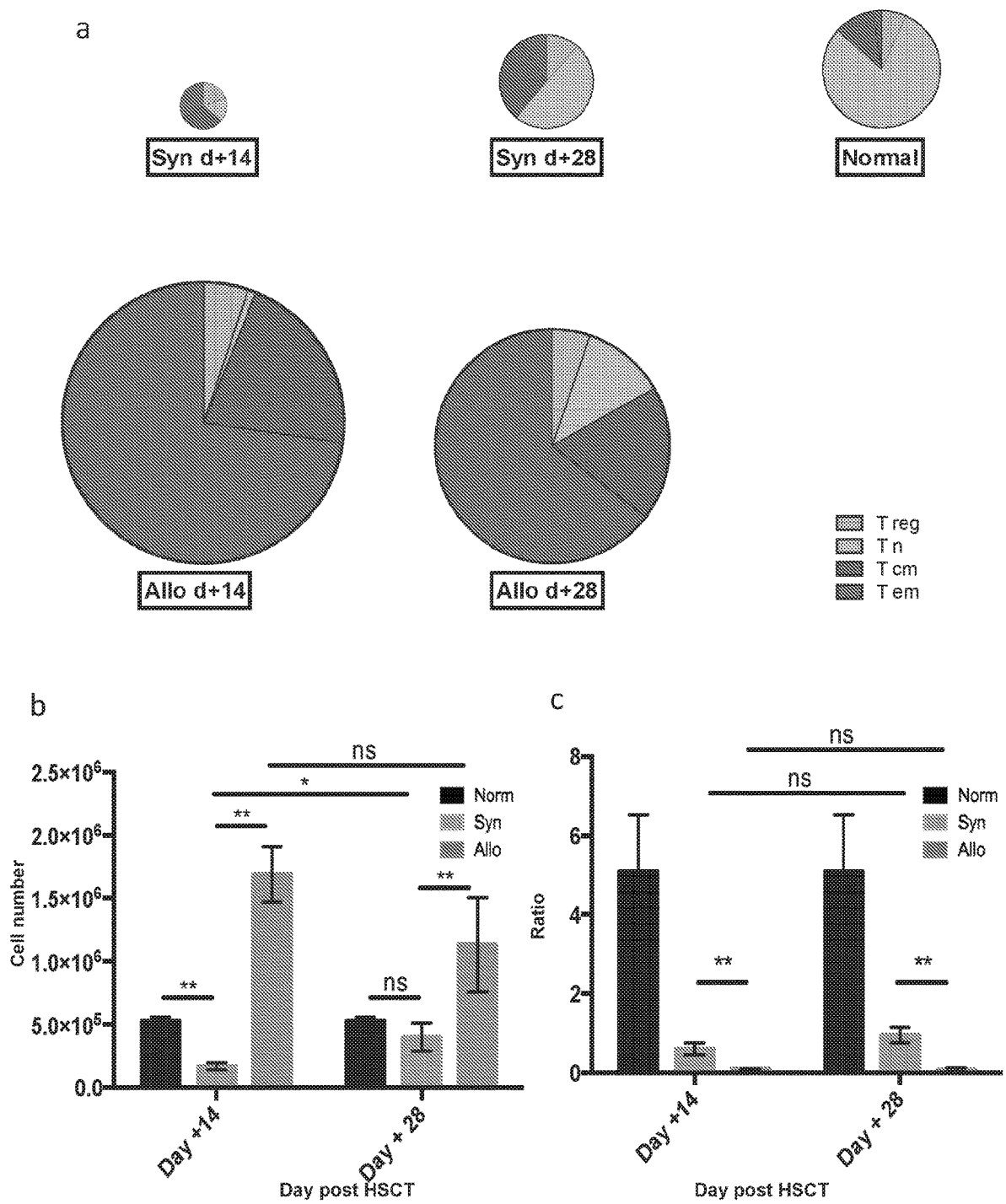
FIGS. 20A-20C include charts and graphs presenting liver CD4+ T cell numbers and compositions for normal mice, syngeneic, and allogeneic HSCT recipients, according to one embodiment.

The following caption applies to FIG. 20: "Parenchymal liver CD4$^+$ T cell number and composition for normal mice, syngeneic, and allogeneic HSCT recipients." (a and b) The mean total CD4$^+$ T cell number for syngeneic day +14=0.2× 10$^6$, syngeneic day +28=0.4×10$^6$, allogeneic day +14=1.7× 10$^6$, allogeneic day +28=1.1×10$^6$, normal=0.5×10$^6$. The size of each pie was normalized to one. Data shown in (b) represent the mean, with SEM error bars. (c) $T_{Reg}$: $T_{EM}$ ratio is consistently lower in the allogeneic setting compared to that of syngeneic and normal cohorts. Data shown represent the mean, with SEM error bars. Data for two independent experiments were pooled for this analysis (n=5 to 8 mice per cohort per time point), and are representative of three independent experiments for day +14. *, P<0.05; **, P<0.01.

The following caption applies to FIG. 21: "Dermal T cell number and composition for normal mice, syngeneic and allogeneic HSCT recipients." (a) The average total number of dermal T cells for syngeneic day +14=0.6×10$^6$, syngeneic day +28=1.6×10$^6$, allogeneic day +14=1.5×10$^6$, allogeneic day +28=3.7×10$^6$, normal=2.4×10$^6$. The size of each pie was normalized to one. (b) Dermal CD4+ T cell number for each experimental cohort measured at day +14 and +28. (c) Representative flank dermal flow cytometry data for the allogeneic cohort at day +28. Data for two independent experiments were pooled, and are representative of three independent experiments. (d) Dermal CD4$^+$ $T_{EM}$ cell number for each experimental cohort measured at day +14 and +28. * P=0.02, 0.04, 0.04, left to right; ** P=0.007.

The following caption applies to FIG. 22: "Small intestine lamina propria (LP) and intraepithelial (IE) T cell number and composition for normal mice, syngeneic and allogeneic HSCT recipients." (a) Total number of small intestine LP CD4$^+$ T cells for each experimental cohort measured at day +14 and +28. * P=0.04;  P=0.002, 0.006, 0.002, left to right (b) Total number of small intestine LP CD4$^+$ $T_{EM}$ cells for each experimental cohort measured at day +14 and +28.  P=0.006. (c) Total number of small intestine IE CD4$_+$ T cells for each experimental cohort measured at day +14 and +28. (d) Total number of small intestine IE CD4$^+$ $T_{EM}$ cells for each experimental cohort measured at day +14 and +28. (e) Flow cytometry gating strategy for small intestine LP samples is displayed, with the upper panels representative of syngeneic data for day +14, and the lower panels representative of allogeneic cohort data for day +14. Data for three independent experiments were pooled for the analysis.

Figure 23:
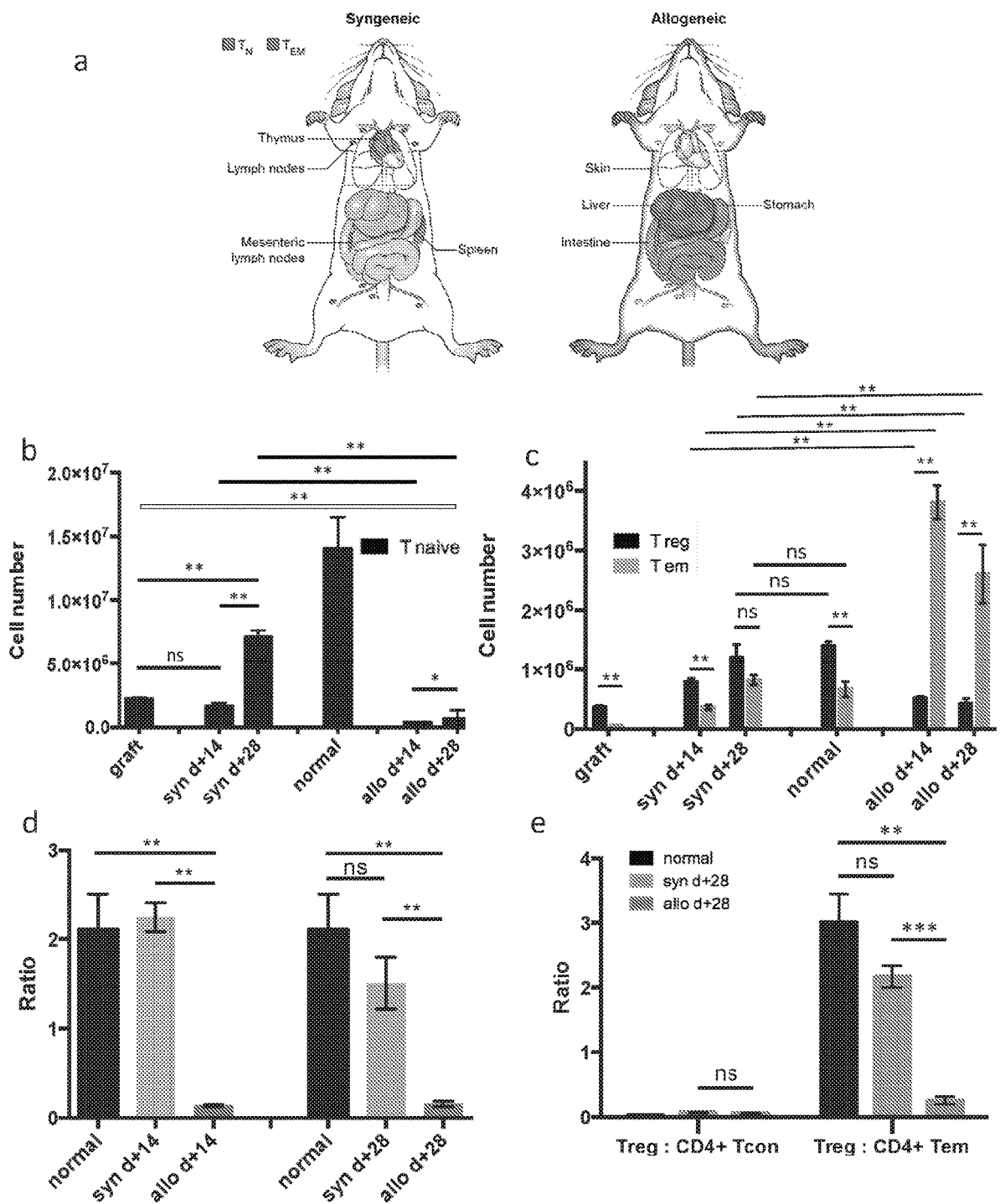
FIGS. 23A-23E include anatomical drawings and charts presenting CD4+ T cell pool sizes, compositions and distributions for normal mice, syngeneic and allogeneic HSCT recipients, according to one embodiment.

Overall, CD4+ T cell immune reconstitution in the syngeneic transplant setting mirrored distribution and composition of T cells in normal mice, i.e. lymphoid organs (FIG. 23A). The predominant phenotype for CD4+ T cells in normal mice and syngeneic recipients was naïve ($T_N$, Foxp3− CD44 low CCR7+) (FIGS. 23A-B). In the syngeneic cohort, few CD4+ T cells were found outside of the lymphoid tissues. In contrast, lymphoid organs in the allogeneic setting underwent atrophy with few CD4+ T cells present in these anatomic locations. Additionally, in the allogeneic cohort CD4+ T cells were primarily localized to the target tissues, such as the integument, liver, and gastro-intestinal tract, and were mostly of the $T_{EM}$ phenotype (FIGS. 23A, C). This resulted in a very low (<<1) target organ, systemic, and peripheral blood $T_{Reg}$ to $T_{EM}$) ratio in the allogeneic setting (FIG. 20C and FIGS. 23(D-E). In contrast, the $T_{Reg}$ to $T_{EM}$ ratio was significantly higher (>1) in the syngeneic and normal cohorts in all the same sites (FIG. 20C and FIGS. 23D-E). To elucidate why $T_{Reg}$ cells were diminished while $T_{EM}$ cells were expanded in the allogeneic setting we obtained measurements of in vivo cell kinetics for CD4+ T cell subsets.

The following caption applies to FIG. 23: "The CD4+ T cell pool size, composition and distribution for normal mice, syngeneic and allogeneic HSCT recipients." Cell numbers on display in this set of figures were generated by adding CD4+ T cell subset numbers extracted from whole spleen, whole parenchymal liver, small intestine (intra-epithelial and lamina propria layers), flank skin (calculated by adjusting excised section numbers for calculated body surface area), and peripheral blood (collected volume adjusted for calculated total blood volume. (e) $T_R$). (a) Graphic representation of the predominant CD4+ T cell subset distribution in the syngeneic and allogeneic HSCT recipients at day +28. CD4+ T cells were primarily found in lymphoid organs and were of $T_N$ phenotype in the syngeneic cohort. Pattern of CD4+ T cell distribution for the normal and syngeneic cohorts was identical. In contrast, CD4+ T cells were primarily found in target tissues (skin, liver, gut) with predominance of $T_{EM}$ phenotype in allogeneic setting. (b) The mean total T naïve cell number measured within the graft, normal mice, and syngeneic and allogeneic recipients at day +14 and +28, with SEM error bars. (c) The mean total $T_{EM}$ and $T_{Reg}$ cell numbers measured within the graft, normal mice, and syngeneic and allogeneic recipients at day +14 and +28, with SEM error bars. (d) $T_{Reg}$: $T_{EM}$ ratio was >1 in the graft, syngeneic HSCT recipients and normal mice, while it was <1 in cGVHD setting. (e) $T_{Reg}$: CD4+ $T_{con}$ ratio vs. $T_{Reg}$: CD4+ $T_{EM}$ ratio for normal mice, and syngeneic and allogeneic recipients at d+28 in peripheral blood. Data shown represent the mean, with SEM error bars. Data are representative of more than three independent experiments. *, $P<0.05$; **, $P<0.01$.

In Vivo $T_{Reg}$ Kinetics Indicate Marked Proliferation in Lymphoid and Target Organs and Diminished Survival in Target Organs $T_{Reg}$ number did not increase substantially over the course of allogeneic immune reconstitution, while there was a significant net increase following syngeneic transplantation (FIG. 23C). Meanwhile, cell gain kinetics for $T_{Reg}$ cells extracted from the spleen and liver parenchyma showed high rates of label gain for allogeneic and syngeneic cohorts (FIGS. 24A-B). Furthermore, in the allogeneic setting $T_{Reg}$ cells experienced label gain rates similar to those of $T_{EM}$ cells (FIGS. 24C-D). While both subsets had similarly high rates of label gain in lymphoid and target organs this did not result in an increased systemic $T_{Reg}$ cell number, while the $T_{EM}$ cells were abundant (FIG. 23D). This difference in absolute numbers despite similar label gain kinetics could be driven by differential cell loss kinetics. Indeed, our kinetics data suggest that $T_{Reg}$ cell loss from the liver exceeds that of $T_{EM}$ subset (FIG. 25A). Furthermore, the key difference between the allogeneic liver $T_{Reg}$ and the other CD4+ subsets was the presence of Caspase 3 staining (FIG. 25B), which indicated greater propensity for apoptosis. When first-order elimination kinetics were applied to the observed label loss rates, $T_{Reg}$ subset half-life in liver was estimated to be roughly one-half of the $T_{EM}$ half-life. Increased loss of $T_{Reg}$ cells in the target tissues may explain why $T_{Reg}$ cells as a subset did not expand following HSCT in the allogeneic recipients despite their high rates of label gain. $T_{Reg}$ cells were not observed in target organs nor in circulation in an appreciable number throughout the course of allogeneic immune reconstitution, while $T_{EM}$ cells were circulating and predominated in the target organs (FIGS. 23A, C and FIGS. 25C-D).

Figure 24:
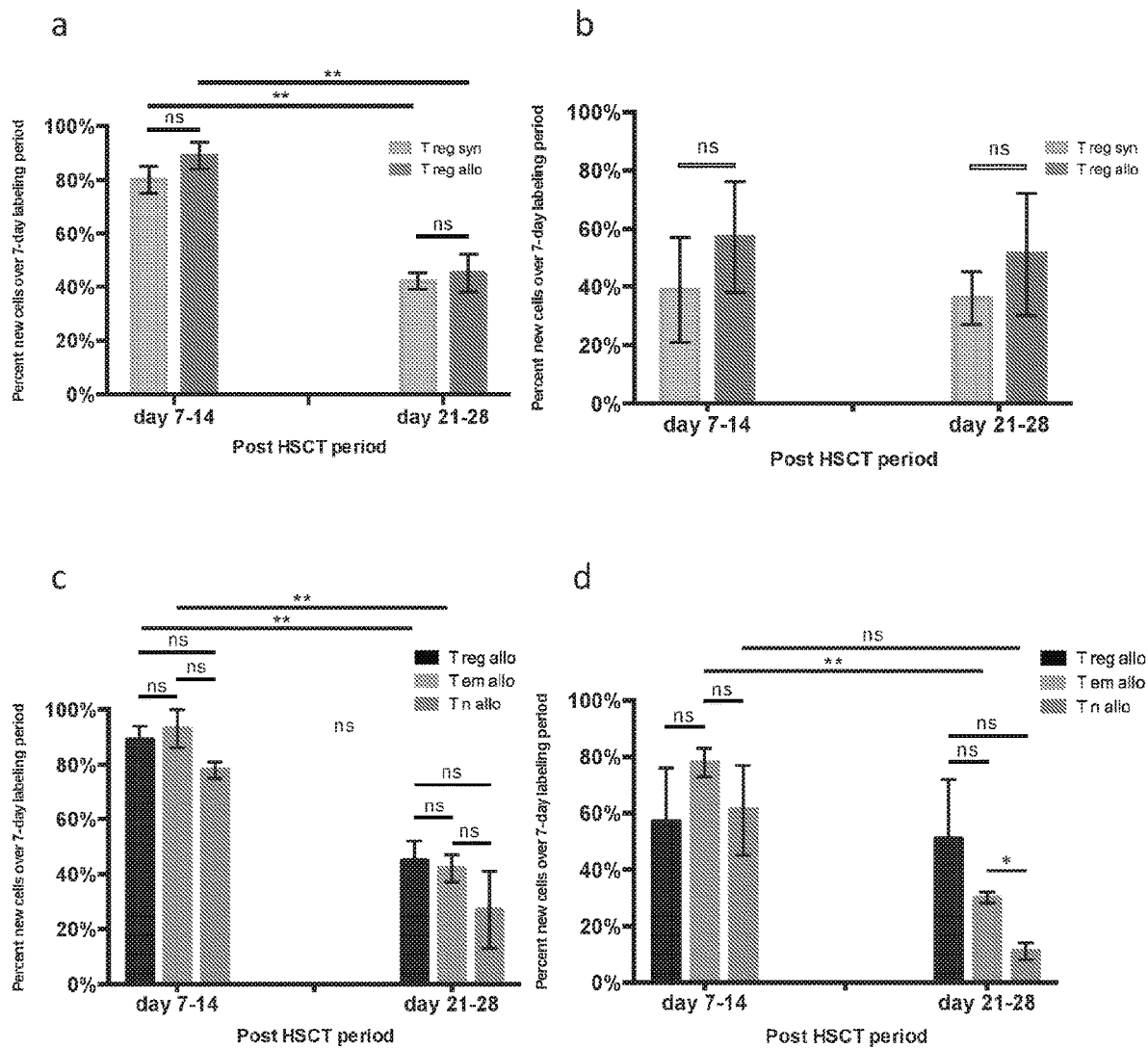
FIGS. 24A-24D include charts presenting cell gain kinetics for $T_{Reg}$ cells in the spleen and liver, according to one embodiment.

The following caption applies to FIG. 24: "Cell gain kinetics for $T_{Reg}$ cells in the spleen and liver." (a) Percentage of new cells within the spleen-derived $T_{Reg}$ subset for each experimental cohort measured at day +14 and +28, following 7 days of label administration for each time point. Data for five independent experiments were pooled for the day +7 to +14 analysis (each independent experiment represents a pooled sample from n=2 to 7 mice), and three independent experiments were pooled for day +21 to +28 analysis. (b) Percentage of new cells within the liver-derived $T_{Reg}$ subset for each experimental cohort measured at day +14 and +28, following 7 days of label administration for each time point. Data for three independent experiments were pooled for the day +7 to +14 analysis (each independent experiment represents a pooled sample from n=5 to 8 mice), and two independent experiments for day +21 to +28 analysis. (c) Percentage of new cells within the spleen-derived allogeneic CD4+ subsets ($T_{Reg}$, $T_{EM}$, and $T_N$) measured at day +14 and +28, following 7 days of label administration for each time point. Data for five independent experiments were pooled for the day +7 to +14 analysis, and three independent experiments were pooled for day +21 to +28 analysis. (d) Percentage of new cells within the liver-derived allogeneic CD4+ subsets ($T_{Reg}$, $T_{EM}$ and $T_N$) measured at day +14 and +28, following 7 days of label administration for each time point. Data for three independent experiments were pooled for the day +7 to +14 analysis, and two independent experiments for day +21 to +28 analysis. Data shown represent the mean, with SEM error bars. *, $P<0.05$; **, $P<0.01$.

The following caption applies to FIG. 25: "Label loss kinetics for $T_{Reg}$ cells in the liver appear to be driven by increased propensity for apoptosis rather than trafficking." (a) Label loss kinetics for allogeneic liver-derived $T_{Reg}$ and $T_{EM}$ cells. Data are representative of three independent experiments for day +14 (n=5 to 8 mice per experiment per cohort), day +28 represents n=5 to 8 mice. (b) Caspase 3 staining for CD4+ $T_{Reg}$, $T_{EM}$, and $T_N$ subsets extracted from the spleen and liver at day +14 (n=5 mice per cohort). (c) The mean total $T_{Reg}$ cell number measured in the peripheral blood of each experimental cohort at day +14 and +28, with SEM error bars. (d) The mean total $T_{EM}$ cell number measured in the peripheral blood of each experimental cohort at day +14 and +28, with SEM error bars. Data are representative of four independent experiments (n=2 to 6 mice per experiment per cohort). **, $P<0.01$.

In Vivo $T_{EM}$ Kinetics Indicate Marked Expansion in Lymphoid and Target Organs and Suggest Trafficking to Target Organs In allogeneic recipients, the total number of $T_{EM}$ cells in all evaluated tissues combined, i.e. spleen, liver, small intestine, skin, peripheral blood, and lymph nodes approached 4 million by day +14, while only 0.06 million were contained in the graft (FIG. 23C). This represents more than a 60-fold expansion of this compartment. In comparison, in the syngeneic recipients, the $T_{EM}$ compartment expanded roughly 10-fold (FIG. 23C). In allogeneic recipients, label gain for the $T_{EM}$ subset in spleen and liver was robust through day +14 (FIGS. 26A-B), and paralleled the overall concurrent increase in the $T_{EM}$ cell number during this period in both organs (FIGS. 18A, C and FIGS. 20A, B)). Additionally, the $T_{EM}$ subset in both organs did not show significant Caspase 3 staining (FIG. 25B). Label loss in the $T_{EM}$ liver subset was slower than that of $T_{Reg}$ cells (FIG. 25(a)); while, in the spleen, $T_{EM}$ cells appeared to undergo rapid label loss (FIG. 26C). A possible mechanism for $T_{EM}$ subset label and absolute number loss from the spleen may be trafficking. This was supported by the measurement of high $T_{EM}$ number in circulation of allogeneic recipients at day +14 (FIG. 25(d)). $T_{EM}$ in vivo cell kinetics showed high label gain in lymphoid and target organs, rapid loss from the lymphoid organ concurrent with a high circulating number and target organ infiltration, without increased propensity for apoptosis. Robust expansion of the $T_{EM}$ subset in the allogeneic setting, both in absolute number and with regard to prominent label gain, was further investigated.

Figure 26:
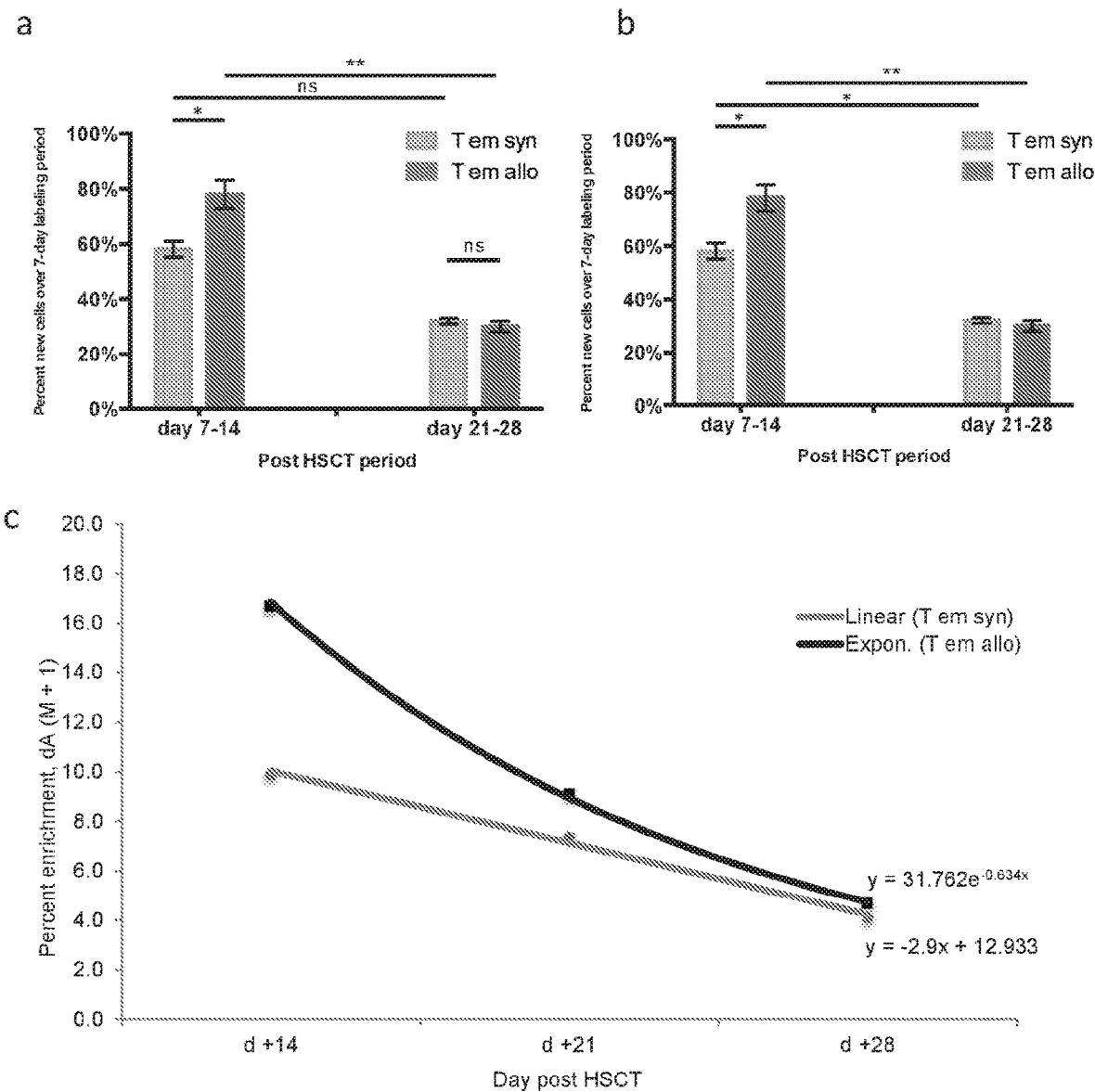
FIGS. 26A-26C include graphs presenting CD4$^+$ $T_{EM}$ in vivo cell kinetics, according to one embodiment.

The following caption applies to FIG. 26: "CD4+ $T_{EM}$ in vivo cell kinetics show robust cell gain in the spleen and liver, with rapid concurrent label loss kinetics in the spleen and increased number in circulation." (a) Percentage of new cells within the spleen-derived $T_{EM}$ subset for each experimental cohort measured at day +14 and +28, following 7 days of label administration for each time point. Data for five independent experiments were pooled for the day +7 to +14 analysis (each independent experiment represents a pooled sample from n=2 to 7 mice), and three independent experiments for day +21 to +28 analysis. (b) Percentage of new cells within the liver-derived $T_{EM}$ subset for each experimental cohort measured at day +14 and +28, following 7 days of label administration for each time point. Data for three independent experiments were pooled for the day +7 to +14 analysis (each independent experiment represents a pooled sample from n=5 to 8 mice), and two independent experiments for day +21 to +28 analysis. (c) Label loss kinetics for spleen-derived $T_{EM}$ cells of allogeneic versus syngeneic recipients. Data are representative of two independent experiments (each independent experiment represents a pooled sample from n=2 to 7 mice). Data are representative of four independent experiments (n=2 to 6 mice per experiment per cohort). *, P<0.05; **, P<0.01.

Figure 27:
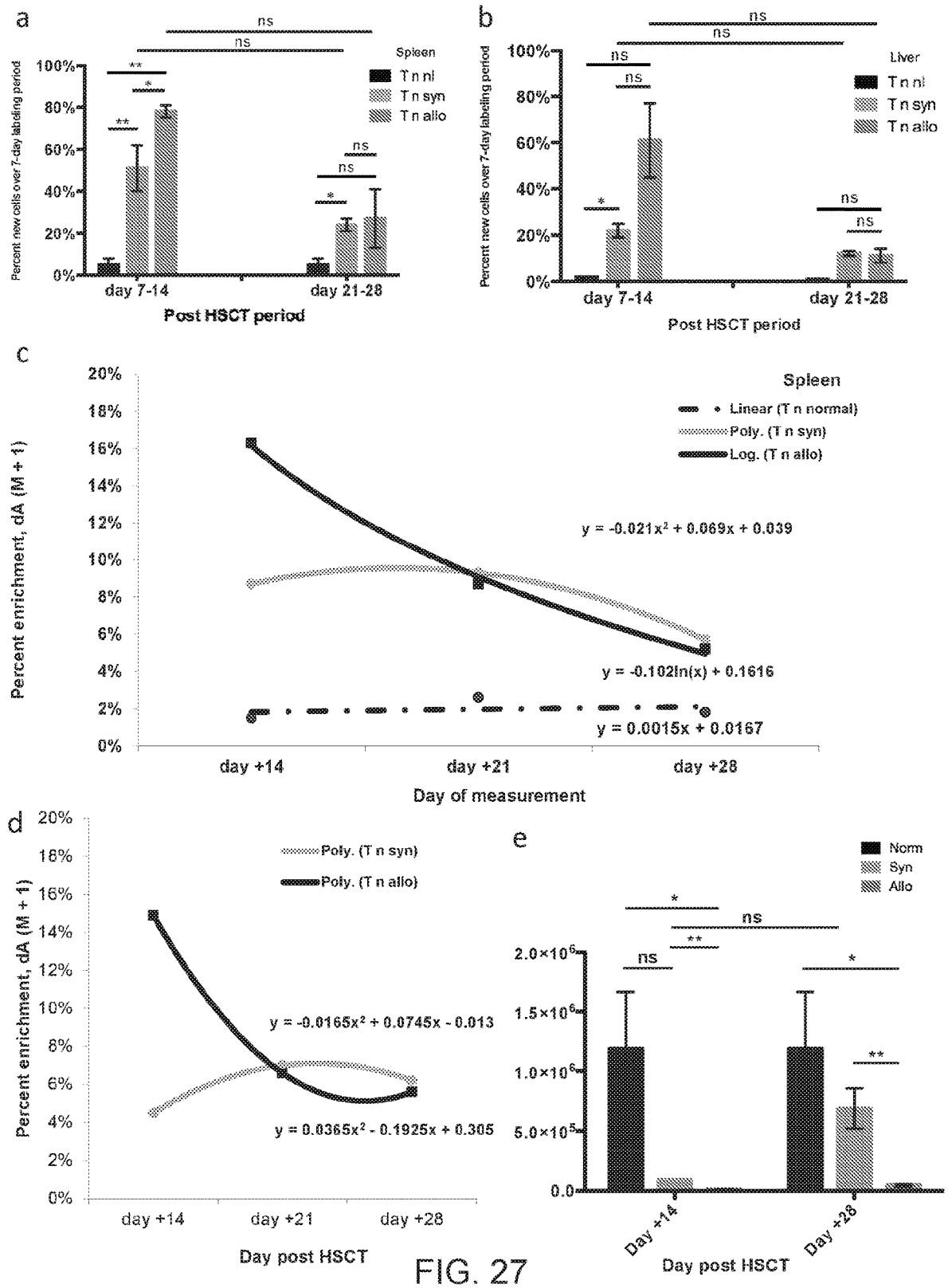
FIGS. 27A-27E includes charts and graphs presenting cell gain kinetics with concurrent rapid label loss in spleen and liver in allogeneic recipients, according to one embodiment.

$T_N$ Expansion and Conversion to $T_{EM}$ Contributes to $T_{EM}$ Predominance in Lymphoid and Target Tissues CD4+ $T_N$ subset displayed high rates of label gain early post transplantation in both syngeneic and allogeneic setting, with the latter demonstrating higher rates in both lymphoid and target tissues (FIGS. 27A-B). However, in contrast to the syngeneic graft that reconstituted the host with a growing number of $T_N$ cells, the allogeneic recipients had fewer $T_N$ cells than contained in the graft at all points following transplantation (FIG. 23B). Label loss for $T_N$ cells was appreciably faster in the spleen and liver of allogeneic versus syngeneic recipients (FIGS. 27(C-D)). Meanwhile, Caspase 3 expression in $T_N$ cells was not increased in either organ (FIG. 25B). The $T_N$ cells were decreased in circulation of allogeneic recipients compared to the syngeneic cohort and those of normal mice (FIG. 27E). Thus, rapid expansion coupled with rapid loss potentially represents $T_N$ conversion to the $T_{EM}$ phenotype. Incorporation of deuterium label into DNA of a particular cellular subset occurs through cell division, because deuterium label incorporates into DNA base pairs only during transcription of new strands. Phenotypic conversion, i.e. from $T_N$ to $T_Em$, involves cell proliferation and differentiation. Our label gain kinetics and flow cytometry data suggest that most of the conversion to the $T_{EM}$ phenotype occurs before day +14 in allogeneic recipients.

$T_N$ cells were not found in circulation of allogeneic cohort at the evaluated time points following transplantation, while $T_{EM}$ cells were found in circulation at day +14 (FIG. 27E and FIG. 25D, respectively). This indicates that a likely site of $T_N$ to $T_{EM}$ conversion is the spleen, with subsequent egress of $T_{EM}$ cells from the spleen. In the syngeneic setting, $T_N$ cells appeared to undergo high rates of label gain and minimal label loss in both spleen and liver (FIGS. 27A-D). This paralleled a growing absolute number of $T_N$ cells observed over the course of syngeneic engraftment (FIG. 23B). $T_N$ expansion was observed even in thymectomized syngeneic HSCT recipients, suggesting lack of $T_N$ conversion to $T_{EM}$ is a key difference between allogeneic and syngeneic immune reconstitution. As expected, in normal mice little label gain or loss was measured in the $T_N$ subset (FIGS. 27A-D), likely due to immune homeostasis. To summarize, our data indicate that in the syngeneic setting $T_N$ cells proliferate to expand the $T_N$ subset, while in the allogeneic setting they proliferate and convert to $T_{EM}$.

The following caption applies to FIG. 27: "In allogeneic recipients CD4+ $T_N$ cells display robust cell gain kinetics with concurrent rapid label loss in spleen and liver, but low circulating number." (a) Percentage of new cells within the spleen-derived $T_N$ subset for each experimental cohort measured at day +14 and +28, following 7 days of label administration for each time point. Data for five independent experiments were pooled for day +7 to +14 (each independent experiment represents a pooled sample from n=2 to 7 mice), and three independent experiments for day +21 to +28 analyses. (b) Percentage of new cells within the liver-derived $T_N$ subset for each experimental cohort measured at day +14 and +28, following 7 days of label administration for each time point. Data for three independent experiments were pooled for day +7 to +14 (each independent experiment represents a pooled sample from n=5 to 8 mice), and two independent experiments for day +21 to +28 analyses. (c) Label loss kinetics for spleen-derived $T_N$ cells of allogeneic versus syngeneic recipients. Data are representative of two independent experiments (each independent experiment represents a pooled sample from n=2 to 7 mice). (d) Label loss kinetics for liver-derived $T_N$ cells of allogeneic versus syngeneic recipients. Data are representative of three independent experiments for day +14 (n=5 to 8 mice per experiment per cohort), day +28 represents n=5 to 8 mice. (e) The mean total $T_N$ cell number measure in the peripheral blood for each experimental cohort at day +14 and +28, with SEM error bars. Data are representative of four independent experiments (n=2 to 6 mice per experiment per cohort). *, P<0.05; **, P<0.01.

Figure 28A:
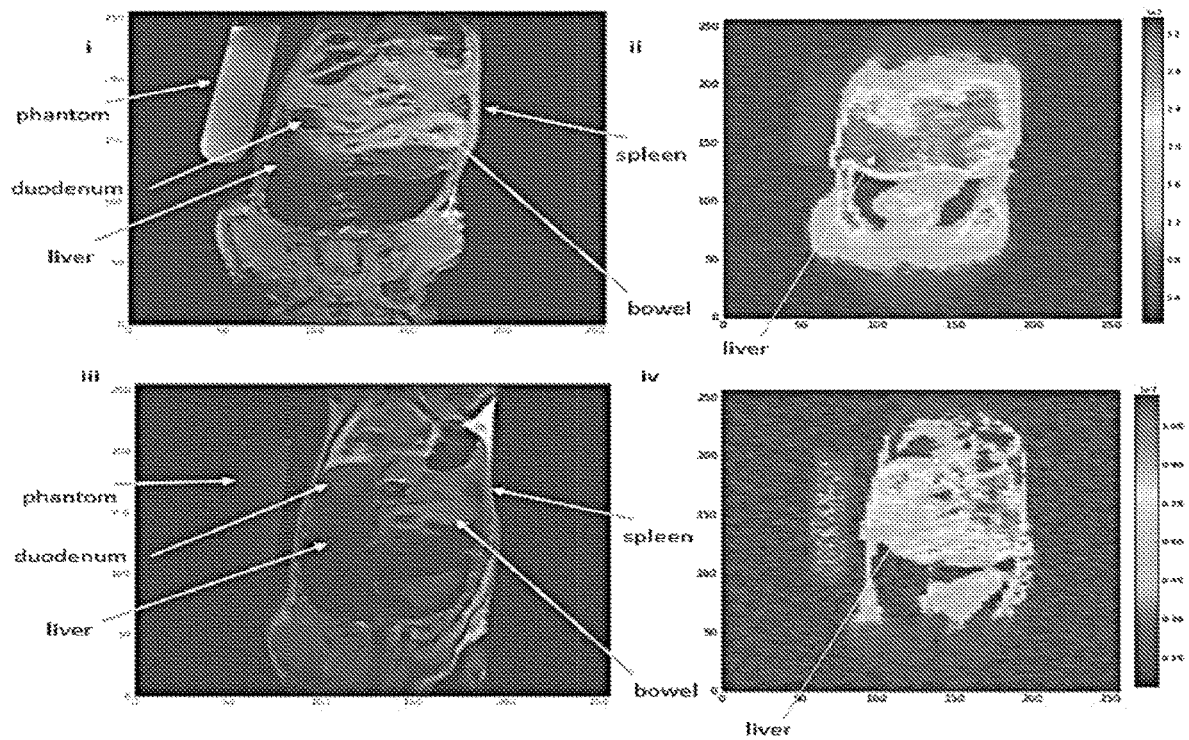
FIGS. 28A-28D include images and charts related to the in vivo deuterium labeling followed by dMRI diagnosis of cGVHD in the target organ, according to one embodiment.
Figure 28B:
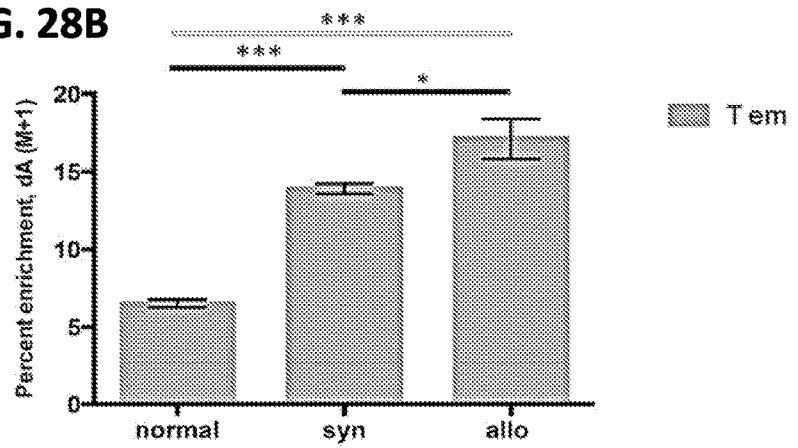
Figure 28C:
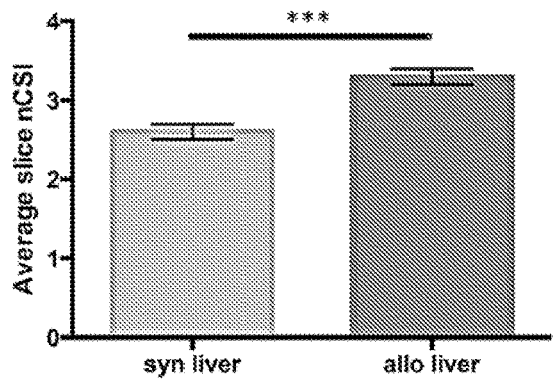
Figure 28D:
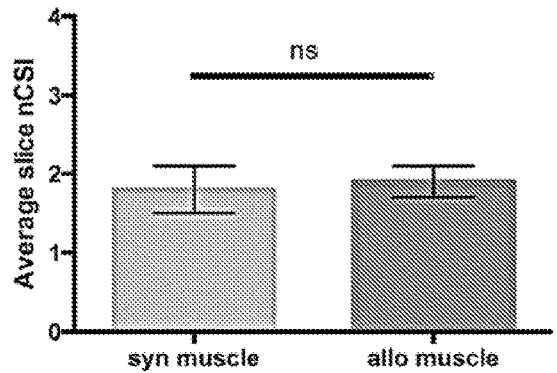

Deuterated Water Labeling Followed by In Vivo Deuterium Magnetic Resonance Imaging (dMRI) Distinguishes Mice with from Those without cGVHD Our measurements of high deuterium ($^2$H) enrichment in deoxyadenosine (dA) of liver-infiltrating $T_{EM}$ cells (FIG. 28A) and the high number of this cell type within target organs of cGVHD-affected mice (FIGS. 20A and 23A, 23C), prompted us to measure in vivo $^2$H signal within organs of mice in both cohorts. Based on the difference in $^2$H levels between background total body water enrichment (TBW) of ~5% achieved for kinetics studies and the resultant higher enrichment (~15-20%) in the liver-infiltrating $T_{EM}$ subset, we initiated deuterium ($^1$H) chemical shift imaging (CSI), a type of magnetic resonance imaging (MRI), in our mouse model. A custom manufactured $^1$H-$^2$H coil for 9.4 Tesla magnet was used to conduct mouse imaging (FIGS. 29A-29B). The detected $^2$H signal within livers of cGVHD-affected mice was significantly greater than that measured in syngeneic controls at day +28, following 21-days of $^2$H$_2$O labeling to TBW of ~5% (FIG. 28(a-b)). Furthermore, no difference in $^2$H signal was observed within a tissue not targeted by cGVHD in our mouse model, such as the quadriceps muscle group (FIG. 28D)

The following caption applies to FIG. 28: "In vivo deuterium labeling followed by dMRI facilitates diagnosis of cGVHD in the target organ." (a) Deuterium chemical shift imaging (CSI) overlaid on proton (anatomical) magnetic resonance imaging (MRI) obtained with Bruker 9.7 T magnet on day +28 following AHSCT, after 21 days (day +7 to +28) of $^2$H$_2$O labeling to total body water of 5%. For each mouse, 3 coronal slices 3-mm in thickness were obtained through the mid-abdomen (region covering liver and spleen); 5% $^2$H$_2$O phantom was imaged with each mouse to provide a reference CSI signal. The MRI image obtained was rotated 180° for the sake of convention. (b) DNA enrichment with deuterium, measured in deoxyadenosine (dA) via GC-MS/MS for the liver CD4+ $T_{EM}$ subset in the three cohorts at day +14. The mean and SEM are displayed. *, P<0.5, *, P<0.001. (c) Average slice normalized deuterium CSI (nCSI) in the liver was significantly higher in cGVHD-affected mice compared to syngeneic recipients, while the unaffected tissue (muscle) deuterium nCSI did not differ between cohorts, shown in (d). For (c) and (d), mean nCSI is presented with SEM error bars, Data are representative of two independent experiments (for the experiment shown, n=4 and 3 for allo and syn, respectively). *, P<0.001.

The following caption applies to FIGS. 29A-B: "Components of the ($^1$H-$^2$H) proton-deuterium coil." (a) Schematic of the "quasi Helmholtz" $^1$H transmit/receive coil for scout (anatomical) imaging. The blue double arrow indicates the B$_1$ direction in regard to the magnet Cartesian coordinates (B$_0$=Z=horizontal). (b) Schematic of the (q)-channel of the "quasi Helmholtz" saddle-type $^2$H transmit/receive coil for chemical shift imaging (CSI). The red double arrow indicates the B$_1$ direction in regard to the magnet Cartesian coordinates (B$_0$=Z=horizontal). (c) Schematic of the (i)-channel of the "quasi Helmholtz" saddle-type $^2$H transmit/receive coil for CSI. The green double arrow indicates the B$_1$ direction in regard to the magnet Cartesian coordinates (B$_0$=Z=horizontal). (d) Schematic of the setup for $^1$H and $^2$H imaging at 9.4 Tesla magnetic flux density. All coils are mounted on a cylindrical former. The coil described in (a), shown here as a blue circle, is connected in a standard way to the MRI system, including the transmit/receive switch. The deuterium coil consists of two identical dual saddle-shaped "quasi Helmholtz" pairs at a 90° angle, described in (b) and (c) and shown here as red and green circles, respectively. The orthogonal arrangement and 90° phase delayed feeding of the RF current reduces the power requirement for a well-defined flip angle to ½, compared to that needed for a single-saddle coil. In addition, the signal-to-noise ratio is increased by a factor of √2. A power transmitter at $^2$H frequency is connected at port #1 of the hybrid via a band pass filter to a quadrature hybrid for power splitting and phase creating. Ports #2 and #3 of the hybrid are connected to the two $^2$H coil ports using identical length cables. The combined signal is received at port #4 of the hybrid that acts as a transmit/receive switch. The signal is passed to another band pass filter to the x-receive port.

Discussion:

Our work elucidates differential in vivo kinetics of CD4+ T cell subsets, which lead to skewed immune reconstitution following allogeneic hematopoietic stem cell transplantation (HSCT). This pre-clinical model mirrors matched unrelated donor HSCT in patients because minor antigen mismatch between donor and host induces clinical GVHD. This model rapidly evolves into chronic GVHD with short latency, which differs from patients in whom manifestations are temporally separate from graft infusion and acute GVHD, however the spectrum of clinical manifestations in patients is recapitulated, for instance sclerotic dermal involvement, which is pathognomonic for cGVHD is prominent. We show that subsets of non-$T_{Reg}$ CD4+ T cells, which are often treated as a single cell population and referred to as CD4+ T conventional ($T_{CON}$), have differential in vivo behavior. Quantitative dynamic in vivo cell kinetics measurements have not been previously obtained for subsets of non-$T_{Reg}$ CD4+ T cells. Additionally, we measured these processes in multiple anatomic compartments. Previous studies employed mathematical modeling to hypothesize in vivo cell kinetics outside of the circulation while measuring deuterium label gain and loss in circulating cells. In contrast, we obtained quantitative measurements of deuterium gain and loss in T cell subsets from lymphoid and target organs, and found the same subset (i.e. $T_{Reg}$) to behave differently depending on site. Bioluminescent studies in mice have demonstrated differential trafficking of T cell subsets in acute GVHD, however this methodology is based on enumeration of cells in organs, which we also accomplished by direct extraction from tissues and subset phenotyping by flow cytometry. Enumeration would be unable to address cell kinetics, i.e. whether minimal T cell subset accumulation in a particular compartment (e.g. $T_{Reg}$ in liver) is due to diminished proliferation or results from robust proliferation followed by apoptosis; furthermore, $T_{Reg}$ as a subset were not compared to $T_{EM}$. Other studies evaluated lymphoid organs, but lymphoid manifestations of GVHD do not provide a full view of in vivo biology. For instance, in our cGVHD model, we show that lymphoid and target organs are different with respect to T cell number, subset proportions, and cell kinetics.

By direct lymphocyte extraction from tissue parenchyma, we were able to map CD4+ T cell subset distribution to the relevant targets of cGVHD, including liver, skin, and gastrointestinal tract, the latter two have not been examined in the cGVHD setting with regard to CD4+ T cell subsets. Similar to patients with cGVHD, the allogeneic recipients in our model were lymphopenic when peripheral blood was evaluated. Low CD4+ T cell numbers were also found in the thymus, lymph nodes, and spleen; however, these animals had a greatly increased number of CD4+ T cells in the target organs, particularly of the $T_{EM}$ phenotype. A system-wide imbalance between immune regulation and activation was highlighted by the reduced ratio of $T_{Reg}$ to CD4+ $T_{EM}$ cells in the setting of cGVHD compared to immune reconstitution without antigenic mismatch. These findings indicate that measurement of this ratio prospectively on patients undergoing HSCT may represent an early biomarker of cGVHD. We show that the $T_{Reg}$ to CD4+ $T_{EM}$ ratio<<1 (in any of the compartments we evaluated, including blood) is the key parameter that predicts which animals go on to develop cGVHD and consistently identifies animals with clinically apparent cGVHD. This ratio is superior to the $T_{Reg}$ to $T_{CON}$ ratio and the $T_{Reg}$ to CD4+ $T_{CON}$ ratio, which are in wide use in HSCT and other fields, as they are not altered across all relevant tissues (lymphoid, target, and circulation) nor are they currently being used in clinical assessments or scoring of GVHD in patients. This highlights that evaluation of subsets of CD4+ $T_{CON}$ (i.e. $T_{EM}$) is biologically relevant, especially because CD4+ $T_{CON}$ subsets do not uniformly have similar in vivo behavior or function.

Previous investigations indicated that differential T cell proliferation was responsible for the imbalance between immunoregulatory and pro-inflammatory elements observed in cGVHD. However, we show that CD4+ $T_{EM}$ cells and $T_{Reg}$ cells undergo robust expansion in lymphoid and target tissues. $T_{Reg}$ number remains low, however, secondary to diminished survival in the target organ of cGVHD. $T_{EM}$ in vivo kinetics pattern is one of high label gain coupled with minimal concurrent label loss. Therapy for GVHD has aimed to reduce general T cell proliferation, while our findings indicate that both, immunoregulatory and pathogenic, CD4+ T cell subsets expand robustly following allogeneic HSCT. The $T_{Reg}$ subset is likely compromised by increased propensity for apoptosis, rather than failure to proliferate. This indicates that therapeutic interventions should aim to reduce $T_{EM}$ expansion, avoid harming $T_{Reg}$ proliferation, and promote $T_{Reg}$ survival. There have been several promising examples of the latter approach for acute and chronic GVHD, where $T_{Reg}$ survival was improved either through manipulation of the cytokine milieu, for example low dose IL-2 therapy, or through affecting inherent changes in the $T_{Reg}$ cells.

To target $T_{EM}$ subset expansion, it is important to understand the dynamic cell kinetics of this subset over the course of cGVHD. Our selective congenic graft experiments show that high label gain in this subset within lymphoid and target organs is in part driven by conversion of non-$T_{Reg}$ CD4+ T naïve ($T_N$) cells to $T_{EM}$ phenotype. Conversion of $T_N$ to $T_{EM}$ occurs early post-HSCT and is likely triggered by recognition of allo-antigens, which does not occur in syngeneic recipients. The conversion heralds impending cGVHD and is further perpetuated over the course of cGVHD. As such, our data concur with others in that $T_N$ cells contained in the graft are critical to acute and chronic GVHD induction. In our study, donor CD4+ $T_N$ cells undergo conversion shortly after graft infusion, and the effector subset they convert to then mediates cGVHD in host organs. A key point that reconciles previously published studies and ours is that for cGVHD initiation the priming for conversion of $T_N$ to $T_{EM}$ has to occur in the host, as $T_{EM}$ (FoxP3−) selected grafts do not result in cGVHD in our studies, which concur with previous work. We did not find $T_N$ cells in circulation, target, or lymphoid organs in allogeneic recipients after day +7. In contrast, we found $T_{EM}$ cells in circulation at day +14, presumably en route from spleen to target organs. In our syngeneic cohort, the number of $T_N$ cells increased over the course of immune reconstitution, and was consistently higher than that of the allogeneic cohort, even in thymectomized animals. This is another feature of cGVHD that may have diagnostic importance. Given the above points, we are developing a treatment strategy to selectively inhibit in vivo CD4+ $T_{EM}$ subset expansion, including that which occurs via $T_N$ conversion to $T_{EM}$. As such, our current work is focused on identifying metabolic differences between $T_{Reg}$, $T_N$, and $T_{EM}$ cells early in the course of allogeneic HSCT. Cell kinetics studies described herein have formed the framework for this research, as they identified which cell subsets should be pursued, their anatomic location, and post-transplantation timing for further investigation.

When in vivo deuterated water labeling is conducted post-HSCT, the DNA of rapidly proliferating cells, such as CD4+ $T_{EM}$ cells, becomes highly enriched with deuterium. As illustrated by our kinetics studies, CD4+ $T_{EM}$ cells in cGVHD-affected mice are preferentially enriched with deuterium to 31 15-20%, well above background total body water (TBW) enrichment of ~5%, which was implemented for kinetics studies. Combining this deuterium enrichment difference and the contrasting distribution of T cell subsets in cGVHD versus syngeneic recipients, we hypothesized that target organs affected by cGVHD could be visualized in vivo with deuterium chemical shift imaging (CSI), also referred to as deuterium MRI (dMRI). We show that high enrichment of deuterium within target organs does indeed allow visualization of these organs by dMRI. As hypothesized, dMRI provided a means by which cGVHD animals could be distinguished from syngeneic counterparts. Thus, dMRI allows non-radioactive and non-invasive diagnosis of cGVHD in our mouse model. Currently, no imaging modalities for cGVHD are in use for cGVHD diagnosis in patients. In clinical practice, biopsies are performed when feasible, often limited by accessibility and morbidity concerns. Hence, in vivo deuterium labeling followed by dMRI could serve as a diagnostic clinical imaging modality for cGVHD, providing a body-wide assessment of disease involvement.

Given that deuterium enrichment is tied to cell proliferation, we demonstrate a first of many potential translational applications for this non-invasive and non-radioactive in vivo labeling-imaging approach. Deuterated water labeling-imaging could facilitate non-invasive in vivo imaging of many cell types, including neoplastic cells. As such, we have been able to image mouse tumor cells labeled with deuterium in vitro, and in vivo studies are planned. dMRI could provide an alternative to current imaging modalities for cancer diagnosis and relapse surveillance, such as computerized tomography (CT) and/or positron emission tomography (PET), both of which involve radioactivity. In addition, it is possible that dMRI could be used for in vivo visualization of immunotherapeutic products post infusion, for example, chimeric antigen receptor T cells (CAR T cells), tumor infiltrating lymphocytes (TILs), and other adoptive immunotherapies, if such products undergo labeling during manufacture or expansion in culture prior to administration to a patient.

In summary, the use of deuterated water labeling for dynamic measurement of in vivo cell gain and cell loss kinetics and the imaging of such cells in vivo via dMRI should illuminate disease-specific pathophysiology, identify targets for therapeutic interventions, and facilitate diagnosis of conditions characterized by rapidly dividing cells.

Materials and Methods

Mice.

Three experimental cohorts were used: normal un-manipulated mice, recipients of syngeneic HSCT, and recipients of allogeneic HSCT. Female BALB/cAnNCr (H-2d) at 12-13 weeks of age served as recipients/hosts. For syngeneic transplantation age-matched female BALB/c mice served as donors. In a subset of experiments thymectomized BALB/c mice served as recipients, and these thymectomized animals were purchased. For allogeneic transplantation age-matched female B10.D2-Hc1 H2-T18C/nSnJ (H-2d) mice served as donors. Congenic experiments were conducted using Thy1.1 B10.D2 and Thy1.1 Cg-FoxP3-GFP B10.D2 mice. BALB/c mice were purchased from Charles River, Wilmington, Mass. B10.D2 mice were purchased from Jackson Laboratories, Bar Harbor, Me. Congenic mice were bred at the NCI Frederick, Md. breeding and holding facility. All animal protocols were approved by the NCI Animal Care and Use Committee.

Bone Marrow and Splenocyte Transplantation.

Recipient female mice were reconstituted with 8 million un-fractionated splenocytes and 15 million bone marrow cells injected via tail-vein on day 0, after 850 cGy TBI conditioning on day −1, delivered in two divided doses 3 hours apart. Gentamicin was added to injection buffer (100 µg/ml). No additional antibiotics were administered following transplantation. Congeneic experiments were conducted using an allogeneic graft comprised of Thy1.1 Ly 9.2 spleen cells and Thy 1.2 Ly 9.2 T cell-depleted marrow transplanted into Thy1.2, Ly 9.1 hosts. Mice received regular drinking water and food until $^2H_2O$ water labeling commenced. cGVHD scoring was performed twice weekly using previously described clinical scoring system. Animals were weighed weekly and on the day of euthanasia for experiments involving dermal and peripheral blood flow cytometry.

$^2H_2O$ (Deuterated Water) Labeling.

Deuterated water labeling was performed according to previously published protocol. Briefly, deuterated water was provided in drinking water after an initial intravenous bolus for specified labeling periods, during which newly synthesized cells incorporate deuterium into DNA base pairs. Incorporation of the label occurs through the de novo synthesis of nucleosides. Sequential labeling and pulse-chase experiments, allow quantitative measurements of cell gain and cell loss, respectively, in an organ or tissue from which the cells are extracted. For cell gain kinetics, the fraction of newly synthesized cells during each 7-day labeling period was calculated by dividing dA M+1 for the population of interest by dA M+1 for a reference fully turned over population (unfractionated bone marrow). Unfractionated bone marrow was collected for each experimental cohort as a pooled sample at each time point. De-labeling kinetics were obtained by measuring day +14 dA M+1 with a preceding 7-day labeling period. Thereafter, label administration ceased and mice received regular drinking water. Measurements for dA+M1 were obtained at day +21, +28 and +35 for spleen de-labeling experiments and day +21 and +28 for liver de-labeling experiments. The enrichment values were then plotted over time. Formulas for de-labeling curves were obtained in Microsoft Excel for Mac 2011 with linear, logarithmic or polynomial fitting.

Urine Sample Collection.

For each mouse that underwent dMRI, ~50 ul of urine was collected prior to imaging. Urine collection was facilitated by placing the mouse on a strip of parafilm, then gently massaging the bilateral flanks. Upon spontaneous passage of urine onto parafilm, the urine was transferred into 1.5-ml Eppendorf with a transfer pipette. The urine samples were stored at −20° C. until total body water (TBW) deuterium enrichment analysis on GC-MS/MS was performed.

Organ Collection and Preparation.

Integument.

The harvesting of lymphocytes from flank sections was performed according to previously published methodology. Briefly, dorsal skin was harvested and subcutaneous adipose tissue was removed. One $cm^2$ sections underwent enzymatic digest in Liberase TL (Roche) for 2 hours at 37° C. and 5% $CO_2$. Digested skin sections were then loaded into medicon cartridges and mechanically ground on the Medimachine System (Becton Dickinson). While lymphocytes were extracted from one $cm^2$ sections from each mouse, total body surface area was calculated for each mouse based on weight (BSA=k $mass^{0.667}$, where k is the Meeh constant empirically determined for each species) allowing whole skin lymphocyte content to be estimated.

Liver.

Circulating non-parenchymal blood was flushed out of the liver prior to organ harvest by intra-cardiac injection of 20 ml PBS with outflow through the cut portal vein. Gallbladder was removed prior to processing. Tissue was mechanically disrupted and sequentially filtered through 100 µm, 70 µm, and finally 40 µm filters. ACK lysis was used prior to re-suspending cells for counting.

Small Intestine.

The small intestines were harvested and processed per previously described protocol. Briefly, the small intestine was cut proximally at the pyloric junction, then drawn out of the peritoneal cavity. Adipose tissue was manually removed. Another cut was made at the cecal junction and the small intestine was then removed from the carcass. Intestinal tissue was placed into medium containing 3% fetal calf serum (FCS) in RPMI (3% media) on ice. Peyer's patches were then removed and processed separately (per Lymphoid organs preparative procedure). The small intestine was cut longitudinally and fecal matter was manually removed. Residual fecal material was rinsed off with 3% media, followed by a rinse in Hank's Balanced Salt Solution (HBSS). The tissue was then cut into 1-cm sections and placed into solution containing 0.145 mg/ml DTT (dichlorodiphenyltrichloroethane) in 3% media and incubated for 20 minutes at 37° C. with continuous mixing (magnetic stirrer mixing at ~800 RPM). Following incubation, the contents were filtered through a stainless steel strainer. The suspension containing the intraepithelial lymphocytes (IEL) was placed on ice. The remaining tissue (on the strainer) was transferred into 0.5M EDTA solution, then vigorously shaken. Following this step, the solution was passed over the strainer and the liquid portion was combined with the rest of IEL (subsequent preparation steps are described under Isolation of IEL section).

Isolation of Lamina Propria (LP) Lymphocytes.

The remaining intestinal sections were placed into solution containing 0.1 mg/ml Liberase TL (Roche) and 0.1 mg/mL DNase I (Sigma-Aldrich) and were finely minced. The mixture was then incubated for 30 min @ 37° C. with continuous stirring at ~800 RPM. The solution was placed on ice and 0.1 mg/mL DNase was added. The contents were then passed over a 70 µm filter. The remnant intestinal pieces were crushed on the filter and rinsed with 0.1 mg/ml DNase solution. The solution was then spun for 5 minutes at 4° C. and 1,300 RPM. The cell pellet was re-suspended in 3% media and filtered over 40 µm filter. Spin step was repeated and the cells were re-suspended in 10% FCS in RPMI media for cell counting.

Isolation of Intra-Epithelial Lymphocytes (IEL).

The solution containing IEL was spun for 7 minutes at 4° C. and 1,400 RPM. The pellet was re-suspended in 3% media, then filtered over 40 µm filter, followed by another spin step. The pellet was then re-suspended in 30% Percoll solution (GE Healthcare) and spun for 20 minutes at room temperature and 1,600 RPM. The cell pellet was re-suspended in 0% FCS media and spun for 7 minutes at 4° C. and 1,400 RPM. The remaining cell pellet was re-suspended in 10% FCS RPMI media for cell counting.

Lymphoid Organs.

Single cell suspensions were obtained by mechanically disrupting lymphoid organs (thymus, spleen, and lymph nodes, including submandibular, axillary, inguinal, mesenteric, and Peyer's patches), then filtering through 70 µm filters. ACK lysis was performed on spleen samples to remove red blood cells prior to cell counting.

Peripheral Blood.

Blood was collected by orbital sinus canulation with heparinized glass tubes and placed on ice. Total volume of sample was recorded. Samples were then spun for 5 minutes at 4° C. and 5,000 RPM. Serum was removed and the samples underwent two ACK lysis steps. Cells were then re-suspended in media for counting. Total blood volume for each mouse based on 7% body weight was used to estimate total lymphocytes present in entire blood volume for each mouse by extrapolating lymphocyte numbers obtained from experimental samples of known collection volume.

Staining for Flow Cytometry and Fluorescence-Activated Cell Sorting.

Cells were counted using Nexcelom Cellometer Auto T4 (Life Technologies, Grand Island, N.Y.) and Trypan Blue 0.4% (Lonza). One to two million cells was aliquoted for flow cytometry staining. For sorting, samples from multiple mice were pooled for each cohort (normal mice, syngeneic recipients and allogeneic recipients). Surface antibody staining was performed on single-cell suspensions. The following antibodies were purchased from eBioscience, BD Biosciences, BioLegend, or Invitrogen: anti-Active Caspase-3 (559341), anti-mouse CD4 (GK1.5), anti-mouse CD8a (5H10, 53-6.7), anti-mouse CD8β, anti-mouse CD16/CD32 Fc block (2.4G2), anti-mouse CD25 (PC61.5), anti-mouse CD69 (H1.2F3), anti-mouse/human CD44 (IM7), anti-CD90.2 (Thy1.2) (53-2.1), anti-mouse CD197/CCR7 (4B12), anti-mouse/rat Foxp3 (FJK-165), anti-mouse CD229.1 (Ly9.1) (3007), Streptavidin Pacific Blue (S-11222), anti-mouse γδ TCR (eBioGL3), anti-TCR β (H57-597). LIVE/DEAD Fixable Aqua Dead Cell Stain Kit (Invitrogen) was used to exclude dead cells. mCD1d (PBS-57) Tetramer was obtained from NIH Tetramer Core Facility (Atlanta, Ga.) for staining liver parenchyma, to allow exclusion of NKT cells from T cells for FACS and flow cytometry phenotyping. The cells were fixed with eBioscience Fixation/Permeabilization reagents, and then intra-cellular staining for Foxp3 was performed overnight at 4° C. Pooled samples for each cohort underwent fluoresce-activated cell sorting (FACS) using Becton-Dickinson (BD) Influx (San Jose, Calif.), with 95% purity. Individual mouse sample flow cytometry measurements were obtained on BD LSR II and collected data were analyzed using FlowJo 9.7.6 Software (Ashland, Oreg.). FACS-purified samples were collected into PBS buffer containing 2% bovine serum albumin. The samples were spun for 10 minutes at 4° C. and 10,000 RPM. Supernatant was removed and remaining cell pellets were stored at −80° C. until DNA extraction.

DNA Extraction.

DNA extraction from non-fixed cells was performed on the Promega Maxwell 16 system (Madison, Wis.) as previously described. For DNA extraction from sorted fixed cells, an EpiSonic™1100 Sonication System (Epigentek, Farmingdale, N.Y.) was used.

GC-MS/MS Analysis dA Enrichment Measurements.

Quantitative determination of deoxyadenosine (dA), its isotopologue (dA M+1) and the internal standard (dA M+5) was measured using validated GC-MS/MS methodology. Briefly, DNA extracted from FACS purified T cell subsets was hydrolyzed to its base pairs using EpiQuick DNA Hydrolysis Kit (Epigentek). The base pairs were then purified and concentrated using solid phase extraction (SPE). The SPE extracts were dried under vacuum, and MethElute™ (methylation reagent) was added to the residue and mixed thoroughly. The Agilent 7890A GC, LTM series II fast GC module, 7000A GC-MS triple quadrupole, and 7693 auto sampler (Santa Clara, Calif.) were then used. Upon injection into the GC, the derivatized base pairs were separated using low thermal mass fast gas chromatography. Calibration standards of dA, dA M+1 and the internal standard (dA M+5) were used for quantitative mass spectrometry, utilizing positive chemical ionization and the MRM mode of MS detection.

Total Body Water (TBW) Enrichment Measurements.

For measuring $^2H_2O$ water levels in TBW (e.g. urine), we developed a simple and quantitative headspace-GC-NCI-MS method (publication pending). Briefly, the method utilizes a rapid gas phase isotopic exchange of the $^1H:^2H$ moiety between $^2H_2O$ water in TBW and the acetone solvent used for isotopic exchange. The method requires 25 μL of TBW sample, i.e. urine, demonstrates a linear relationship from 2-40% $(v/v)^2H_2O$ in TBW, and has a total analysis time of less than 10 min Histopathology.

Thymus, lymph nodes, spleen, liver, stomach, small intestine, colon, skin, lung, and bone marrow (sternum) were extracted from mice immediately following euthanasia and placed into 4% w/v formaldehyde. Tissue cassettes were then sent to Histoserv, Inc. (Germantown, Md.) for sectioning and H & E staining. H & E slides were evaluated for cGVHD histological grading by Dr. ME. Adobe Photoshop Elements 8.0 was used to acquire images of the H & E figures obtained via Olympus DP12 camera visualized through an Olympus BX41 microscope, magnification as noted on each figure.

Proton and Deuterium MRI.

All magnetic resonance imaging (MRI) experiments were performed on a 9.4 Tesla magnet equipped with a Bruker Advance III MRI console (Bruker-Biospin, Billerica, Mass.) Immediately following euthanasia, each mouse was wrapped in plastic and taped onto a plastic cradle in a flat, level position. A 5-mm diameter tube (phantom) containing 5% $^2H_2O$ in $ddH_2O$ with 0.1% sodium azide (preservative) was placed adjacent to the mouse as a reference and calibration standard. The cradle was centered in the MRI probe described above, and then placed in the magnet. Following acquisition of a set of standard locator images, a set of three coronal planes were prescribed covering the spleen and liver. Reference images of these regions were acquired using the MSME sequence and the following parameters: Field of View=40×40 mm, slice thickness=1 mm, TR/TE=1000/14 ms, and the matrix of 256×256. Subsequently, the same planes were imaged using the deuterium chemical shift imaging (CSI) sequence with the following parameters: Field of View=40×40 mm, slice thickness=3 mm, TR/TE=398/1.6 ms, spatial matrix=128×64, and spectral matrix=512. The excitation flip angle was adjusted to meet an Ernst angle condition. All imaging data were analyzed using custom code written in Python. Following CSI reconstruction, regions of interest were placed onto the reference sample, the spleen (when visible), the liver, and muscle. The average intensity and the standard deviation of the intensity was measured and tabulated for each region on the CSI and reference images. Anatomical regions were normalized using the reference (5% $^2H_2O$ phantom) intensity to compensate for experimental variation.

$^1H-^2H$, Proton-Deuterium, Coil for MRI.

The schematic for the components of the proton-deuterium coil is provided in FIGS. 29A-B.

Statistical Analysis.

Data for experimental cohorts were graphed with Prism 6.0 (GraphPad Software, Inc.) or Microsoft Excel for Mac 2011. Error bars on bar graphs represented standard error of the mean (SEM). Data for experimental cohorts were compared with Microsoft Excel for Mac 2011 or Minitab 16.2.4 (State College, Pa.) using two-sample, two-tailed, unequal variance t-test. P values were assigned a single asterisk (*) when they were <0.05, and those marked with ** were <0.01.

It should be understood from the aforementioned descriptions that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for magnetic resonance imaging (MM) to predict or detect an occurrence of rapidly dividing cells in a subject, the method comprising the steps of:
    administering a stable water isotope to the subject;
    allowing the stable water isotope to incorporate into cells of the subject over a period of time while continuing to administer the stable water isotope to the subject during the period of time;
    after the period of time, determining the enrichment level of the stable isotope in the subject by
        positioning the subject within a magnetic field of an MRI system, wherein the MRI system comprises a coil tuned to measure a resonance frequency of the stable isotope and a resonance frequency of proton ($^1$H), performing MRI by measuring signals from the stable isotope and proton in the subject, and
        overlaying the MRI signals from the stable isotope over the MRI signals from the proton to generate an image to detect and map enrichment levels of the stable isotope in the subject; and
    diagnosing the occurrence or a likelihood of occurrence of the rapidly dividing cells in areas of the subject where the enrichment levels of the stable water isotope in the cells of the subject is greater than a background enrichment of the stable water isotope in a total body of the subject, wherein the enrichment levels in the cells and in the background are determined at the same time.

2. The method of claim 1, where the isotope is deuterium ($^2$H), $^{17}$O, or both.

3. The method of claim 1, wherein the total body water enrichment of the stable water isotope is approximately 5% or greater.

4. The method of claim 1, wherein the rapidly dividing cells comprise one or more types of immune cells or cancer cells.

5. The method of claim 1, wherein the coil comprises a first coil tuned to measure a resonance frequency of the stable isotope and a second coil tuned to measure a resonance frequency of proton.

6. The method of claim 1, wherein the MRI further comprises chemical shift imaging (CSI).

7. The method of claim 6, wherein the chemical shift imaging comprises gathering images of an organ or a tissue.

8. The method of claim 1, wherein the MRI provides a chemical shift image of an organ or tissue, which is correlated with anatomical (proton) imaging.

9. The method of claim 1, wherein administering the stable water isotope labeled enriched fluid comprises injecting the enriched fluid into the subject, providing the enriched fluid for ingestion, or both.

10. The method of claim 1, wherein the stable isotope enriched fluid is included in culture media or in a manufacturing process for an immunotherapeutic product.

11. The method of claim 10, wherein the immunotherapeutic product is labeled ex vivo prior to the administering step, and the determining step is used to visualize or monitor localization of the immunotherapeutic product within the subject.

12. The method of claim 1, wherein the diagnosing step further comprises comparing the enrichment level of the stable isotope in the tissue or organ subject with enrichment levels for those without cancer, graft- versus-host disease, immunological disorder, or infection.

13. The method of claim 12, wherein the medical condition is cancer, graft- versus-host disease, an immunological disorder, or an infection.

14. The method of claim 1, wherein the occurrence or a likelihood of occurrence of the rapidly dividing cells indicates a clinical presentation of a medical condition.

* * * * *